(12) United States Patent
Tai et al.

(10) Patent No.: US 8,824,156 B2
(45) Date of Patent: Sep. 2, 2014

(54) POCKET-ENABLED CHIP ASSEMBLY FOR IMPLANTABLE DEVICES

(75) Inventors: Yu-Chong Tai, Pasadena, CA (US); Ray Kui-Jui Huang, Fremont, CA (US)

(73) Assignee: California Institute of Technology, Pasadena, CA (US)

(*) Notice: Subject to any disclaimer, the term of this patent is extended or adjusted under 35 U.S.C. 154(b) by 657 days.

(21) Appl. No.: 12/657,539

(22) Filed: Jan. 21, 2010

(65) Prior Publication Data

US 2010/0265680 A1    Oct. 21, 2010

Related U.S. Application Data

(60) Provisional application No. 61/205,490, filed on Jan. 21, 2009.

(51) Int. Cl.
*H05K 5/00*    (2006.01)
(52) U.S. Cl.
USPC ........... 361/757; 361/761; 361/752; 361/765; 361/762; 607/116
(58) Field of Classification Search
None
See application file for complete search history.

(56) References Cited

U.S. PATENT DOCUMENTS

| | | | | |
|---|---|---|---|---|
| 5,456,698 A | * | 10/1995 | Byland et al. | 607/36 |
| 5,741,313 A | * | 4/1998 | Davis et al. | 607/36 |
| 2004/0199235 A1 | * | 10/2004 | Younis | 607/116 |
| 2006/0265039 A1 | * | 11/2006 | Bartic et al. | 607/116 |
| 2008/0086173 A1 | * | 4/2008 | Ok et al. | 607/2 |
| 2008/0154365 A1 | * | 6/2008 | Tai et al. | 623/6.63 |
| 2008/0176271 A1 | * | 7/2008 | Silver et al. | 435/29 |
| 2009/0198293 A1 | * | 8/2009 | Cauller et al. | 607/2 |
| 2010/0262208 A1 | * | 10/2010 | Parker | 607/62 |

* cited by examiner

*Primary Examiner* — Tuan T Dinh
*Assistant Examiner* — Steven T Sawyer
(74) *Attorney, Agent, or Firm* — Milstein Zhang & Wu LLC; Joseph B. Millstein

(57) ABSTRACT

Systems and methods for providing biologically compatible pockets or envelopes that can contain chips and other circuit elements and can make electrical connection between those elements and living organisms. The assembled biologically compatible pockets and circuit components can have biomedical applications, such as bioimplantable devices such as retinal, cochlear and cortical prosthesis implants, muscular stimulators, and other uses. In various embodiments, the described technology explains how to make and use pocket systems for dealing with chips having connectors on one or two surfaces, and with other circuit components such as resistors, capacitors, inductors and transistors. Operation of chips encapsulated according to the described technology is demonstrated. Accelerated life testing suggests that the pocket systems described will survive for years at 37 degrees C.

19 Claims, 52 Drawing Sheets

FRESH WAFER

BOTTOM PARYLENE DEPOPSITION

METAL DEPOPSITION

2nd LAYER PARYLENE DEPOSITION -
COMPLETE BOTTOM SANDWICH

Si   PR   METAL 1   METAL 2
PARYLENE 1   PARYLENE 2

ETCH BOTTOM CONTACT

PHOTORESIST DEPOSITION

3rd LAYER PARYLENE DEPOSITION - FOR TOP SANDWICH

TOP METAL DEPOSITION

4th LAYER PARYLENE DEPOSITION -COMPLETE TOP SANDWICH

RIE ETCH OPEN TOP CONTACT PADS

ETCH THROUGH PARYLENE TO OPEN ALL CONTACT PADS

RELEASE DEVICE

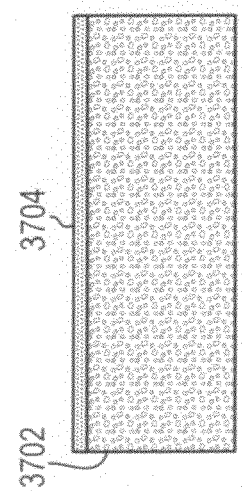
FIG. 37A
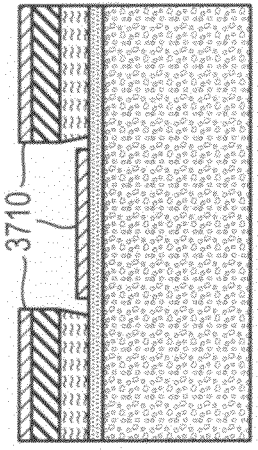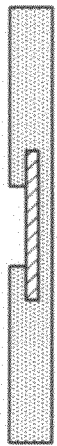
FIG. 37B
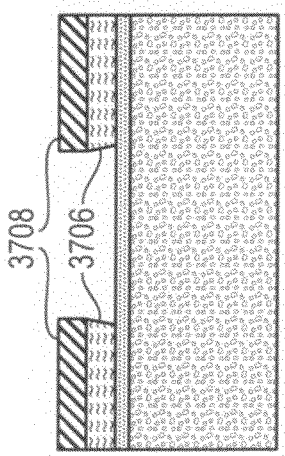
FIG. 37C
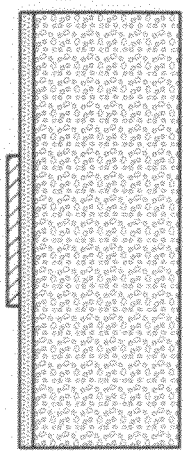
FIG. 37D
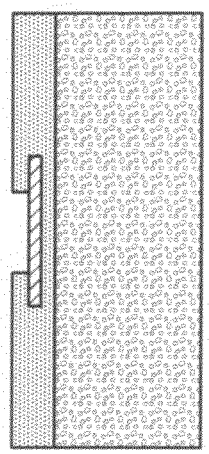
FIG. 37E
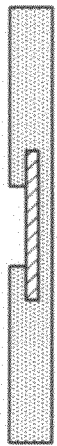
FIG. 37F

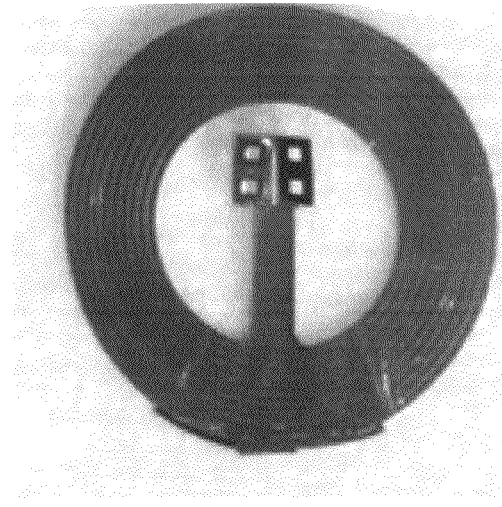
FIG. 39A Before bonding
FIG. 39B After bonding
— 1 mm
| Inductance | DC resistance | Q at 500kHz |
|---|---|---|
| 2.24 μH | 15.82 Ω | 0.45 |
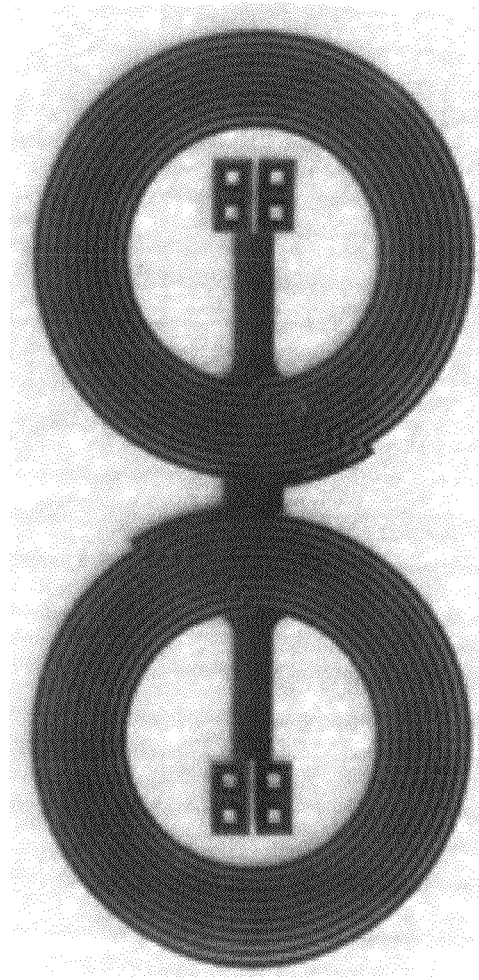

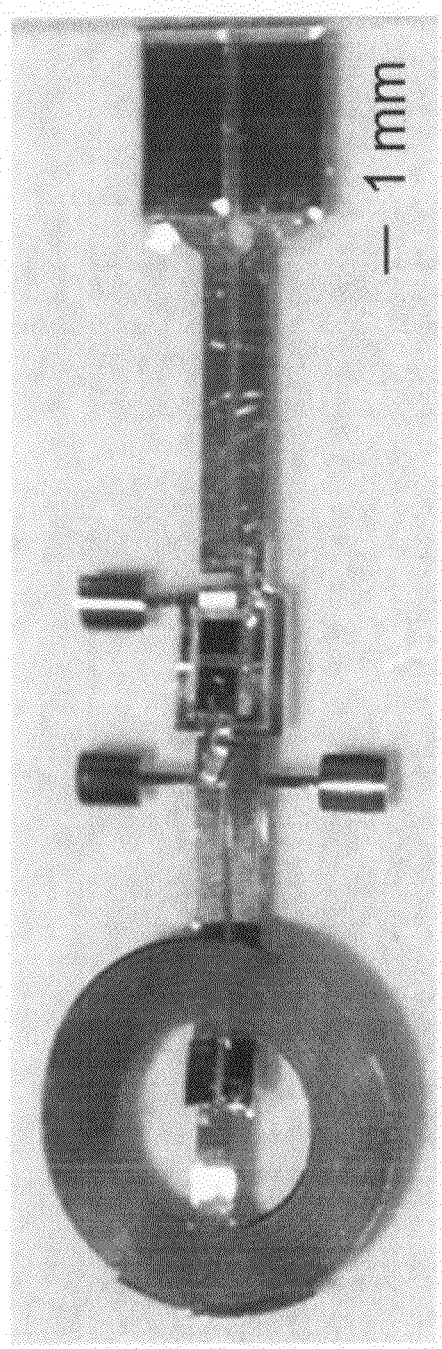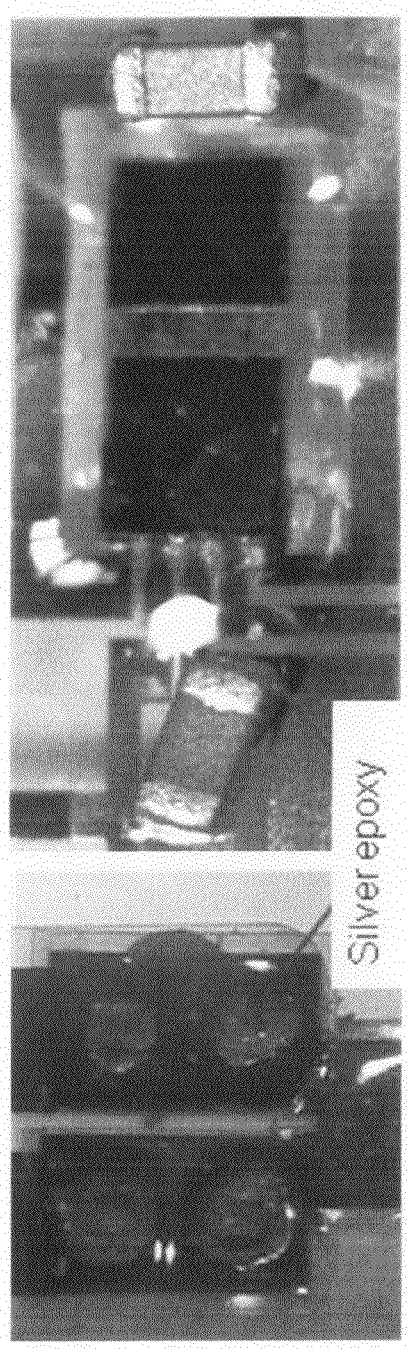

POCKET-ENABLED CHIP ASSEMBLY FOR IMPLANTABLE DEVICES

CROSS-REFERENCE TO RELATED APPLICATIONS

This application claims priority to and the benefit of co-pending U.S. provisional patent application Ser. No. 61/205,490, filed Jan. 21, 2009, which application is incorporated herein by reference in its entirety.

STATEMENT REGARDING FEDERALLY FUNDED RESEARCH OR DEVELOPMENT

The U.S. Government has certain rights in this invention pursuant to Grant No. H0031068 awarded by the National Science Foundation.

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

FIELD OF THE INVENTION

The invention relates to a technology generic for any electronic system assembly involving multiple chips and components, but especially useful for biomedical implants in general and particularly to biomedical implants that employ a chip-in-pocket assembly that allows the total connection and fabrication of a biomedical implant comprising semiconductor chips or other pre-manufactured electrical components such as transistors, resistors, capacitors or inductors.

BACKGROUND OF THE INVENTION

Implantable microelectronic systems can provide improvements in a person's health status, by monitoring and correcting existing medical conditions, or by providing substitute capabilities for normal bodily functions that are damaged or cease to operate. A number of implantable microelectronic systems are currently in use, including cardiac pacemakers and implantable cardioverter defibrillators that monitor heart rhythms and deliver a corrective electrical signal if a dangerous cardiac rhythm is detected (see http://www.nlm.nih.gov/medlineplus/pacemakersandimplantable-defibrillators.html), cochlear prostheses that provide hearing function to some who have lost normal hearing (see http://www.nidcd.nih.gov/health/hearing/coch.asp), and vagus nerve stimulators that can be used to correct or to treat certain conditions (see http://www.mayoclinic.com/health/vagus-nerve-stimulation/MY00183 that describes treatment of depression and http://www.epilepsy.com/epilepsy/vns that describes prevention of epileptic seizures).

Recent advances in the field of neural prosthetics have demonstrated the thought control of a computer cursor. This capability relies primarily on an electrode array surgically implanted into the brain as an acquisition source of neural activity. Various technologies have been developed for signal extraction. However most suffer from either fragile electrode shanks and bulky cables or inefficient use of surgical site areas.

Among current neural prosthesis technologies, some have well controlled metal electrode fabrication and circuitry integration techniques but have designs that are brittle and difficult to handle. Some have reliable interconnect cables but are weak on IC expansion capability.

An important goal in neural prosthesis is to be able to decode the movement intention in the parietal cortex from neurons by implanting neuroprobes. While 3-D integrated silicon probes have been successfully manufactured, the degradation of the signal to noise ratio (SNR) is still a major challenge because electronics are too far away from the recording site. Additionally, recent development in bioimplantable devices such as retinal, cochlear and cortical prosthesis implants also increases the demand for totally implanted technologies.

Recent achievements in silicon probes implantation in the parietal cortex have enabled technological advances in neural prosthesis research. However, current state of the art technologies still suffer from high signal-to-noise ratio and complicated IC integration schemes.

In recent decades, integrated wireless microsystems have provided tremendous opportunities in neural prostheses by establishing an artificial interface to the central or peripheral neural system. For example, retinal implants have been studied for the treatment of outer retinal degenerative diseases, such as age related macular degeneration (AMD) and retinitis pigmentosa (RP). However, many technologies are still in development and few have actually been transferred to the clinical practice due to constraints in material biocompatibility, device miniaturization, and flexibility.

There is a need for a totally biocompatible packaging/integration technology. There is a need for an easy and precise way to electrically connect and assemble various semiconductor chips and pre-manufactured discrete components to provide a functional biomedical system. There is a need for a simple way to electrically connect a large number of connections (e.g., more than 100 interconnections) between chips.

SUMMARY OF THE INVENTION

According to one aspect, the invention relates to a biocompatible sealable pocket. The biocompatible sealable pocket comprises a substrate having a first surface; and a layer of a biocompatible material connected to the first surface of the substrate, the layer of the biocompatible material defining an open pocket between the biocompatible substrate and the layer of the biocompatible material, the open pocket having at least one electrical contact configured to be accessible on an internal surface thereof, the open pocket configured to accept at least one electrical circuit component and to provide electrical communication between the at least one electrical contact and the at least one electrical circuit component. The biocompatible sealable pocket is configured to be sealed and to be implanted within a living organism after accepting the at least one electrical circuit component, the biocompatible sealable pocket configured to provide a biocompatible object capable of biologically significant electrical communication with the living organism within which the biocompatible sealable pocket is implanted.

In one embodiment, the substrate having a first surface comprises parylene. In one embodiment, the substrate having a first surface comprises silicon. In one embodiment, the layer of biocompatible material comprises parylene.

In one embodiment, the open pocket having at least one electrical contact configured to be accessible on an internal surface thereof has electrical contacts on at least two internal surfaces thereof.

In one embodiment, the biocompatible sealable pocket further comprises an electrical cable having electrical conductors therein configured to make electrical connection between at least one probe element and at least one electrical circuit component situated with the pocket, the probe element configured to make electrical connection to the living organism within which the biocompatible sealable pocket is implanted.

In one embodiment, the biocompatible sealable pocket further comprises an electrical signal communication device configured to communicate an electrical signal between the at least one electrical circuit component and an electrical circuit external to the living organism.

In one embodiment, the electrical signal communication device comprises a coil configured to make electromagnetic connection between the at least one electrical circuit component and an electrical circuit external to the living organism. In one embodiment, the biocompatible sealable pocket further comprises a tuning circuit configured to allow operation with an electromagnetic communication signal having predefined electrical parameters.

In one embodiment, the electrical signal communication device comprises a cable configured to make electromagnetic connection between the at least one electrical circuit component and an electrical circuit external to the living organism.

In one embodiment, the biocompatible sealable pocket is combined with at least one electrical circuit component situated with the pocket and electrically connected to the at least one electrical connector; at least one probe configured to make electrical connection to a living organism and connected to the at least one electrical circuit component; and an electrical communication device configured to communicate an electrical signal between the at least one electrical circuit component and an electrical circuit external to the living organism. In some embodiments, the layer of biocompatible material comprises a material selected from the group consisting of PMMA, teflon, silicone and polyimide.

According to another aspect, the invention features a method of making a biocompatible sealable pocket. The method comprises the steps of a. providing a substrate having a first surface; b. depositing a layer of a sacrificial material having a predefined length, a predefined width, and a predefined thickness on a portion of the surface of the substrate; c. depositing a layer of a biocompatible material over the layer of the sacrificial material, the layer of the biocompatible material extending beyond the sacrificial material; d. depositing a layer of a conductive material over at least a portion of the layer of the biocompatible material; e. depositing a second layer of a biocompatible material over the layer of the conductive material, the layer of the biocompatible material extending beyond the conductive material; f. providing openings in the second layer of the biocompatible material to provide electrical access to the conductive material through the second layer of the biocompatible material; and g. removing the sacrificial material to define a free volume having the predefined length, the predefined width, and the predefined thickness, the free volume configured to accept at least one electrical circuit component. The free volume represents an open pocket having at least one electrical contact configured to be accessible on an internal surface thereof, the open pocket configured to accept at least one electrical circuit component and to provide electrical communication between the at least one electrical contact and the at least one electrical circuit component, the biocompatible sealable pocket configured to be sealed and to be implanted within a living organism after accepting the at least one electrical circuit component, the biocompatible sealable pocket configured to provide a biocompatible object capable of biologically significant electrical communication with the living organism within which the biocompatible sealable pocket is implanted.

In one embodiment, the method further comprises the steps of: after the step a. of providing substrate, and before the step b. of depositing a layer of a sacrificial material: (i) depositing on the surface of the substrate a layer of a biocompatible material, the layer of the biocompatible material having a length greater than the predefined length of the sacrificial material, the layer of the biocompatible material having a width greater than the predefined width of the sacrificial material. In this embodiment, the free volume represents an open pocket having a biocompatible material as each of its defining surfaces. In one embodiment, the method further comprises the step of releasing the biocompatible sealable pocket from the substrate, to provide a self-supporting free standing biocompatible sealable pocket.

In another embodiment, the method further comprises the steps of after the step (i) of depositing on the surface of the substrate a layer of a biocompatible material, and before the step b. of depositing a layer of a sacrificial material, (ii) depositing a layer of a conductive material over at least a portion of the layer of the biocompatible material; (iii) depositing a layer of a biocompatible material over the layer of the conductive material, the layer of the biocompatible material extending beyond the conductive material; and (iv) providing openings in the layer of the biocompatible material deposited in step (iii) to provide electrical access to the conductive material through the layer of the biocompatible material deposited in step (iii); and after the step f. of providing openings, and before the step g. of removing the sacrificial material, (v) providing openings in the layers deposited in steps (ii), and b, c, d and e, to provide electrical access to the conductive material deposited in step (ii) through the layer of the biocompatible material deposited in step (iii). There is provided a biocompatible sealable pocket having electrical contacts on two interior surfaces thereof.

In one embodiment, the method further comprises the step of releasing the biocompatible sealable pocket from the substrate, to provide a self-supporting free standing biocompatible sealable pocket.

In some embodiments, the layer of biocompatible material comprises parylene. In some embodiments, the layer of biocompatible material comprises a material selected from the group consisting of PMMA, teflon, silicone and polyimide.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 37 illustrates in cross-section the fabrication process of a parylene-based carrier substrate.

FIG. 39A illustrates a fabricated fold-and-bond coil with two layers of metal, and FIG. 39B illustrates the assembled coil. The electrical characteristics are measured and given in the table.

FIG. 40 illustrates an assembled BION system.

FIG. 41 illustrates interconnects formed with biocompatible conductive silver epoxy: (left) coil contacts, (right) chip and capacitor contacts.

DETAILED DESCRIPTION

Figure 1:
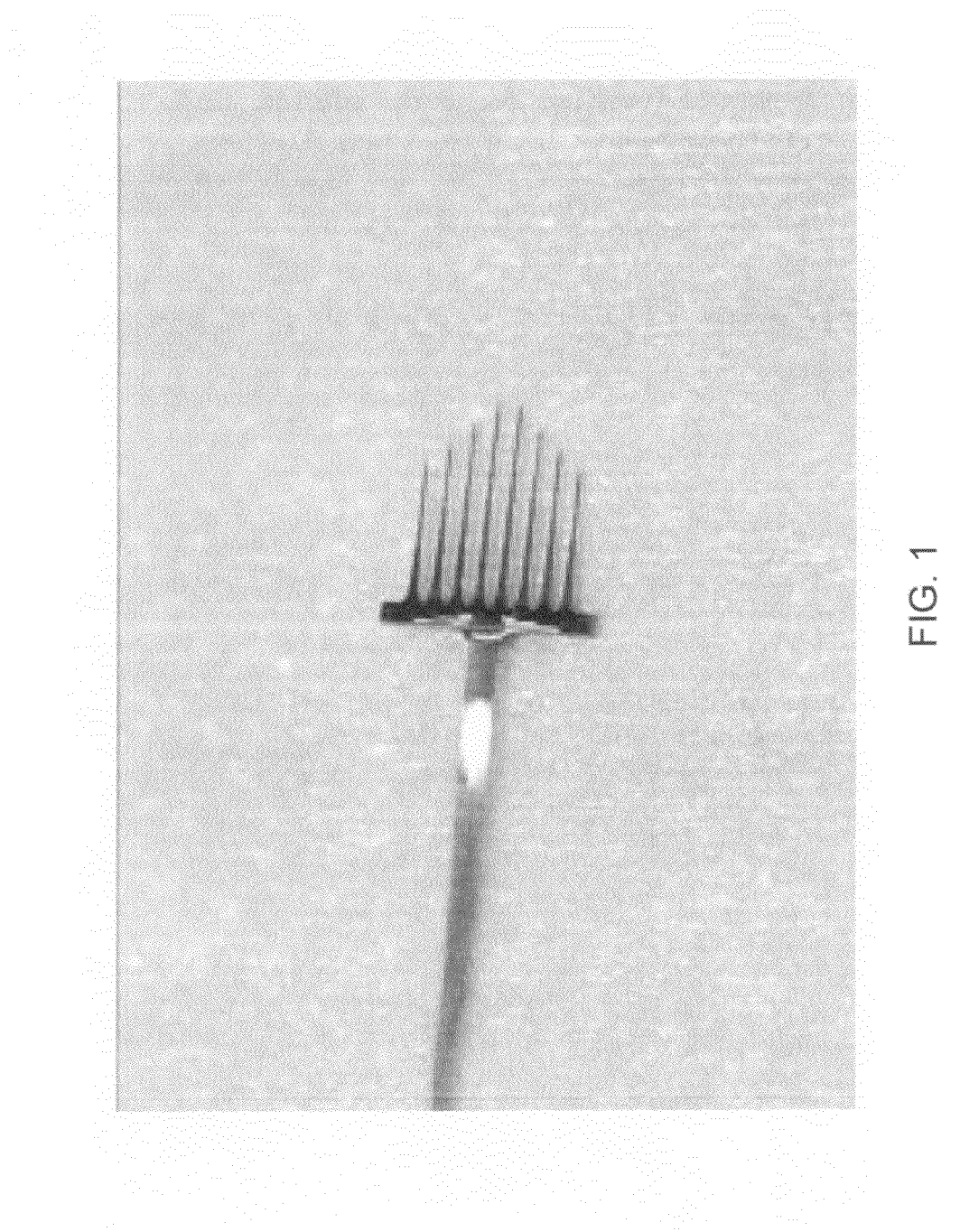
FIG. 1 illustrates a tapered 5 mm length silicon array after releasing from the wafer from which the probe is fabricated.

In this invention, it is believed that the innovation is to use a new "pocket" technology to facilitate the connection and packaging of various different components for use as biomedical implants. To use the technology, pockets (or envelopes) having predesigned sizes to accommodate chips/components, and having pre-metalized electrical connections are made. The chips and correspondent chips/components are then inserted into the pockets with alignment so the metal pads on the pockets and the metal pads on the chips are aligned. Electrical connections between the pockets and the chips/components can be made by applying conductive epoxy or other conductive polymers. These conductive epoxy/polymers can be biocompatible or not, depending on the applications. The end product, however, of this exercise is one or more well connected chips/components on a pocketed substrate or even a completely free-standing flexible substrate, e.g., made of parylene or other polymers. In other terms, after circuitry is inserted into and connected to traces present in the pocket or envelope, the pocket or envelope is sealed closed other than at possible locations where electrical contact with a living organism or biological object needs to be made, such as a the electrically active locations on probes. In some embodiments, communication with the contents of the sealed pocket or envelope from devices external to the living organism or biological object is accomplished using electromagnetic waves using coils.

Communication with an implanted device can be performed using either percutaneous connectors or wireless communication methods. An advantage of a wireless communication method over a percutaneous connector is the elimination of issues relating to possible infection or irritation related to devices that perforate the skin. However, wireless communication in the vicinity of living organisms also poses problems that need to be solved, such as avoidance of local heating, potential concerns relating to subjecting a living organism to long term electromagnetic radiation, and transmission of electromagnetic signals in living media.

Some of the kinds of signals that are communicated between an implanted device and an external device include power signals and data signals. Power signals can include signals that provide power from an external power supply to an implanted device, so that a battery present in the implanted device can be maintained in a suitable state of charge, or so that a battery can be eliminated from the implanted device. For some conventional devices having batteries, surgery may become necessary to replace the device because its battery is expected to reach the end of its useful life. Any surgery poses a health risk and unnecessary surgery is best avoided if possible, especially in persons who already have health issues. Accordingly, implantable devices that do not have to be replaced because of a battery are advantageous.

Data signals can include data signals from an external detector to an implanted device (such as providing an electrical signal corresponding to an audible signal received by a microphone to a cochlear implant for communication by way of a person's nervous system to the person's brain), control signals from an external detector to an implanted device that provide the ability to control the implanted device by using such signals (e.g., controlling the state of operation of the implanted device to meet the needs of the person), and data signals from the implanted device to an external device to monitor the condition and operation of the implanted device itself, to monitor the condition of the person (such as pulse rate, cardiac signals, or other signals relating to the condition being treated) and conditions in the vicinity of the implanted device (such as physiological signals, e.g., temperature, pressure, pH), or to monitor the signals the implanted device is applying to the person. In some embodiments, data signals can be used to "tune" or "reprogram" the implanted device to take advantage of improvements in understanding of the person's condition and the intervention, assistance, or treatment that the person should have, or provide improvements in the implantable device operation and control procedures or operational software that are developed after the device is implanted.

Integrated Parylene-Cabled Silicon Probes for Neural Prosthetics

Here we present a design and initial testing results from high electrode density, silicon based arrays system with an integrated parylene cable. The greatly reduced flexible rigidity of the parylene cable is believed to relief possible mechanical damages due to relative motion between a brain and its skull.

Regardless of the particular technology used to accomplish neural prosthesis, an ideal wired multi-electrode array would comprise (1) biocompatible materials; (2) high density electrodes with high signal-to-noise ratio; (3) reliable, high density cables and a percutaneous interconnect to communicate with peripherals; and (4) ability to accommodate integrated circuitries for on-probe signal amplification.

We describe a parylene coated silicon probe that has the potential to overcome the difficulties presented by the current technology. A major improvement of the current device over prior devices is the complete encapsulation of the array with parylene. The previous generation of bioimplantible prostheses consisted of a silicon substrate that was exposed on all sides except the front side, significantly reducing the biocompatibility of the device. We have chosen to use parylene C (poly-para-xylylene C, also referred to hereinafter as "parylene") due to its insulational capability, flexibility, biocompatibility, and its prior use in medical applications.

Furthermore, our flexible parylene-based cable has a cross section that is 500 μm wide and 15 μm thick and is designed to route the signals acquired with a 32 channel array. An important feature of our device that the cabling is not a component that is later attached to the array. Rather, it is an integrated extension of the parylene structure of the array itself. The resulting manufacturing simplification is expected to significantly improve the reliability of our device. Finally, this monolithically micromachined cable—probe system is able to accommodate future chip integrations through the addition or modification of the silicon pieces on the silicon probe. As a result, we are able to fabricate silicon probe devices that are highly customizable, fully biocompatible, and easy to mass fabricate. It is expected that this technology will facilitate manufacture and use of neural prosthetic systems.

Design

A flexible parylene lift-off technology allows us to fabricate 2-D 32 channel flexible cabled electrode array devices, as illustrated in FIG. 1. FIG. 3, FIG. 4, FIG. 5, and FIG. 6 are images that illustrate features of the silicon bioimplantible array of FIG. 1.

Figure 2:
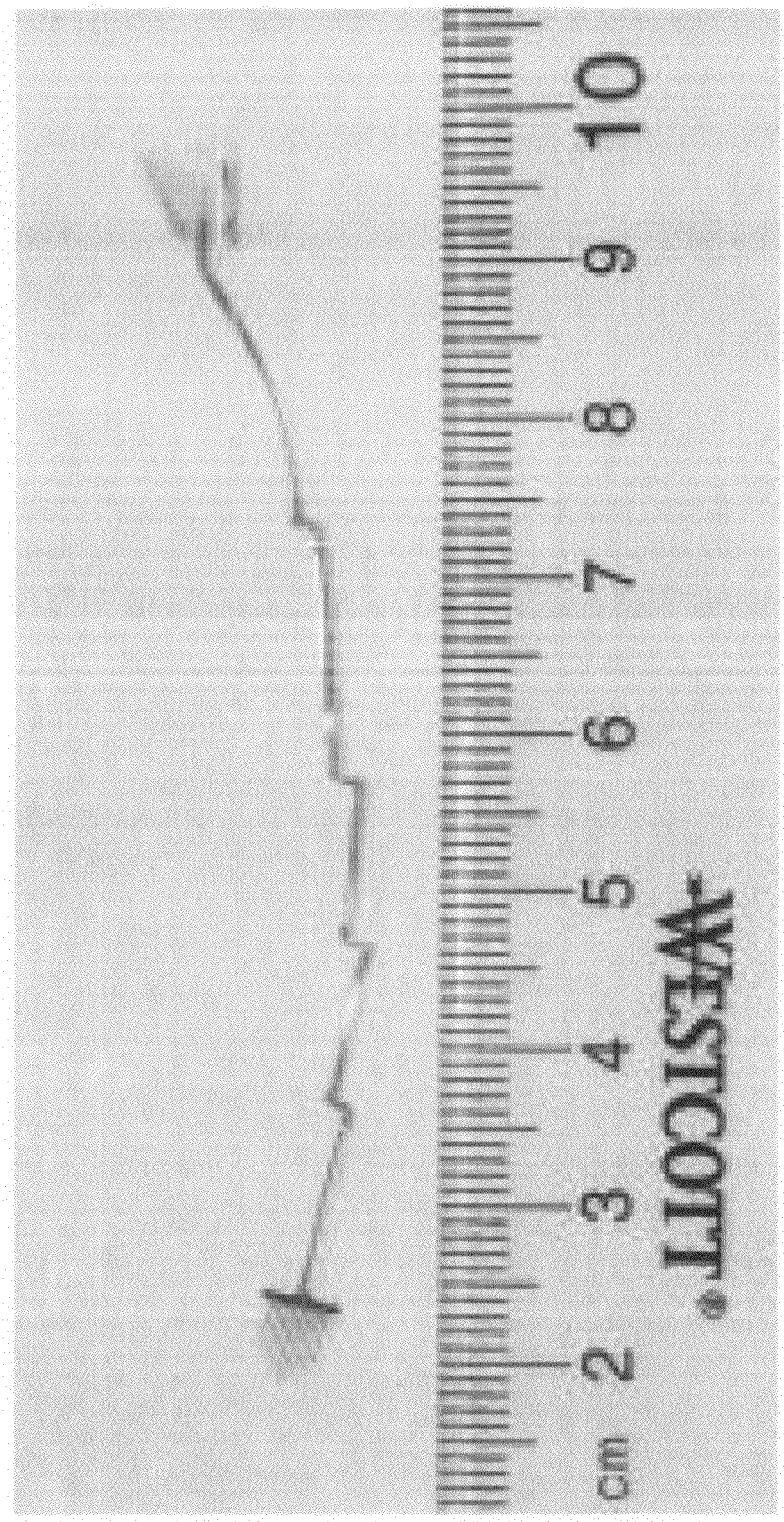
FIG. 2 illustrates a silicon probe with parylene flexible cable.
Figure 3:
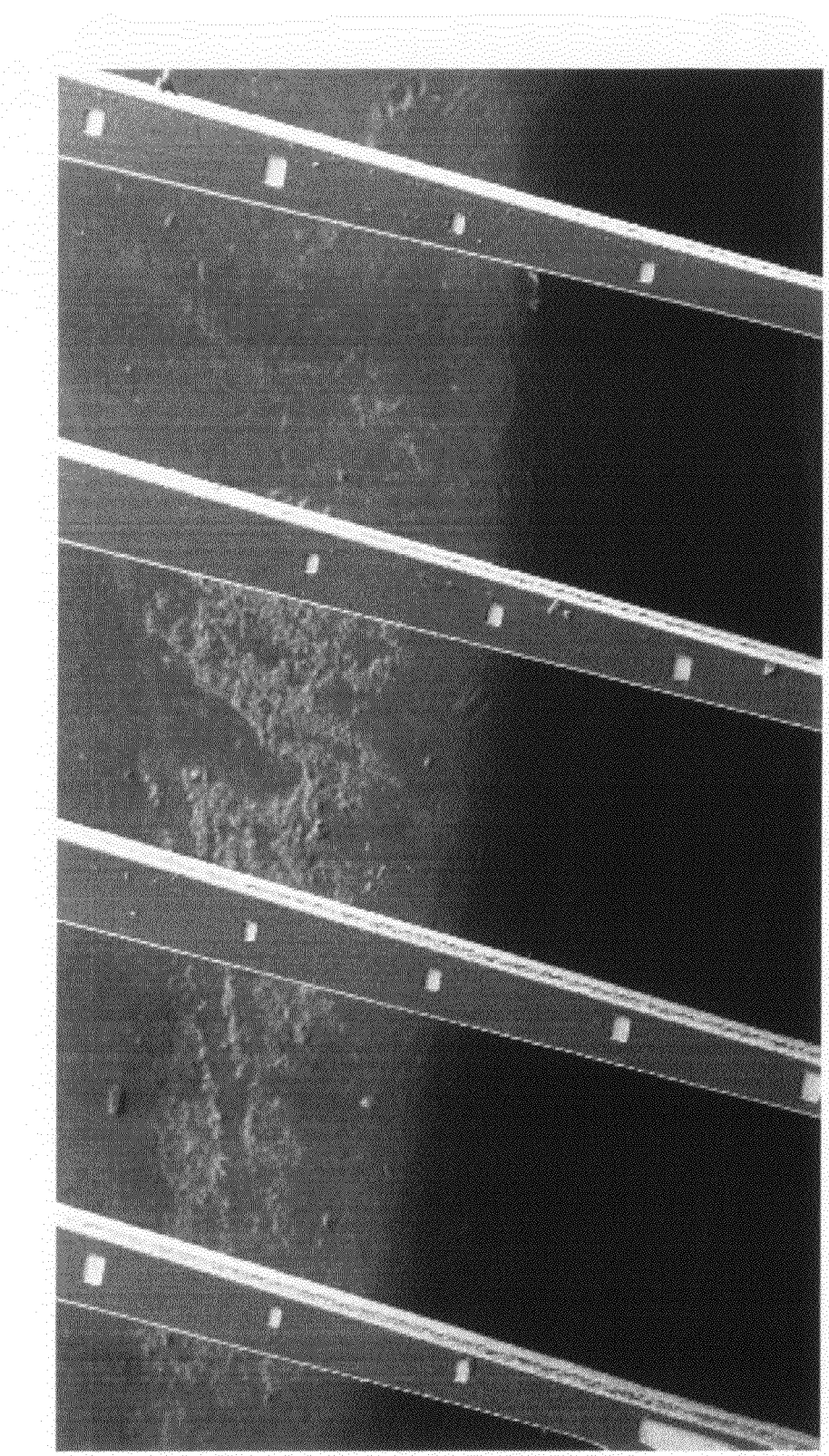
FIG. 3 is an illustrative SEM of the electrodes on silicon shanks of a bioimplantable silicon probe.
Figure 4:
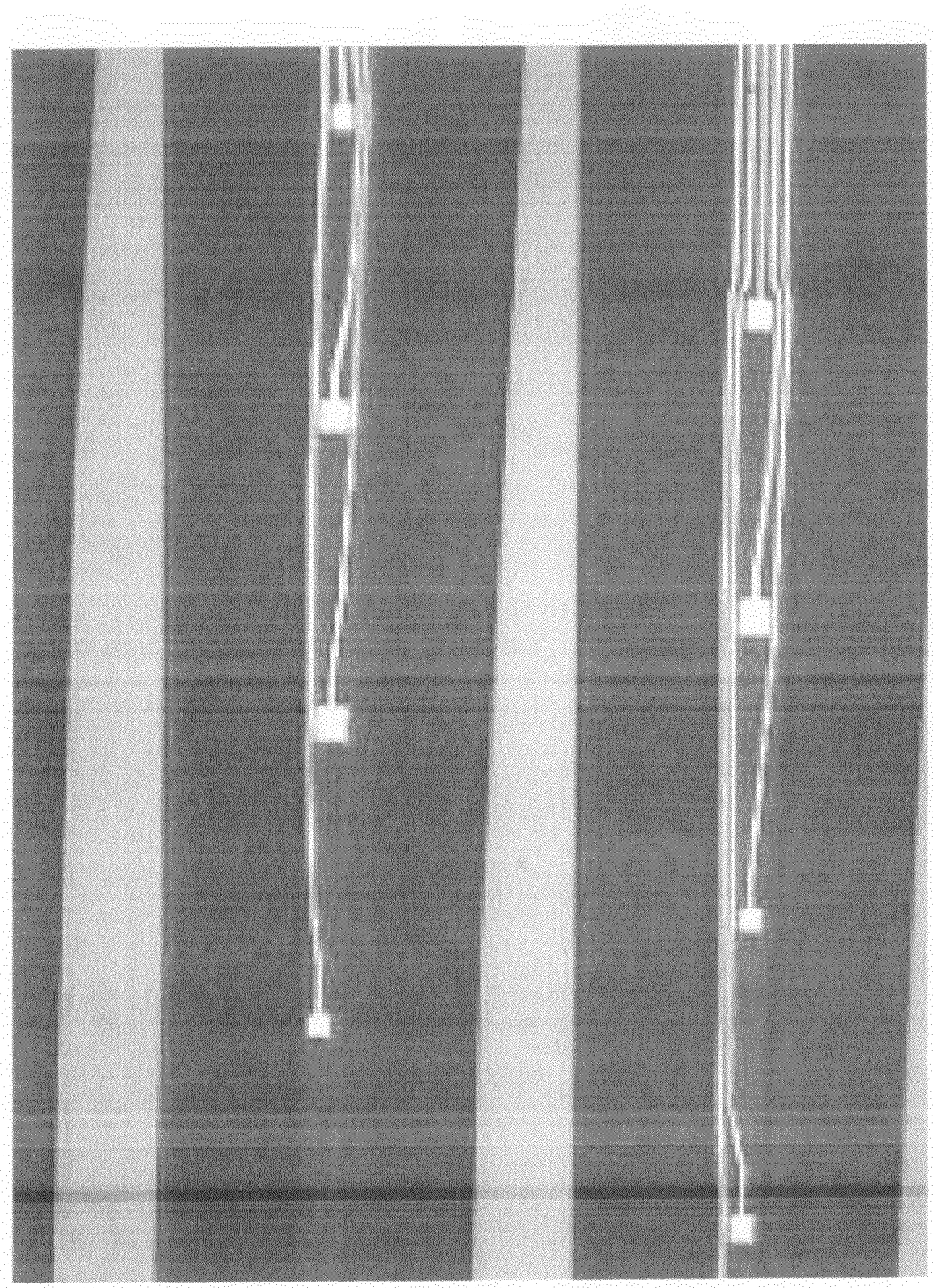
FIG. 4 illustrates platinum electrode pads as seen using a microscope.
Figure 7:
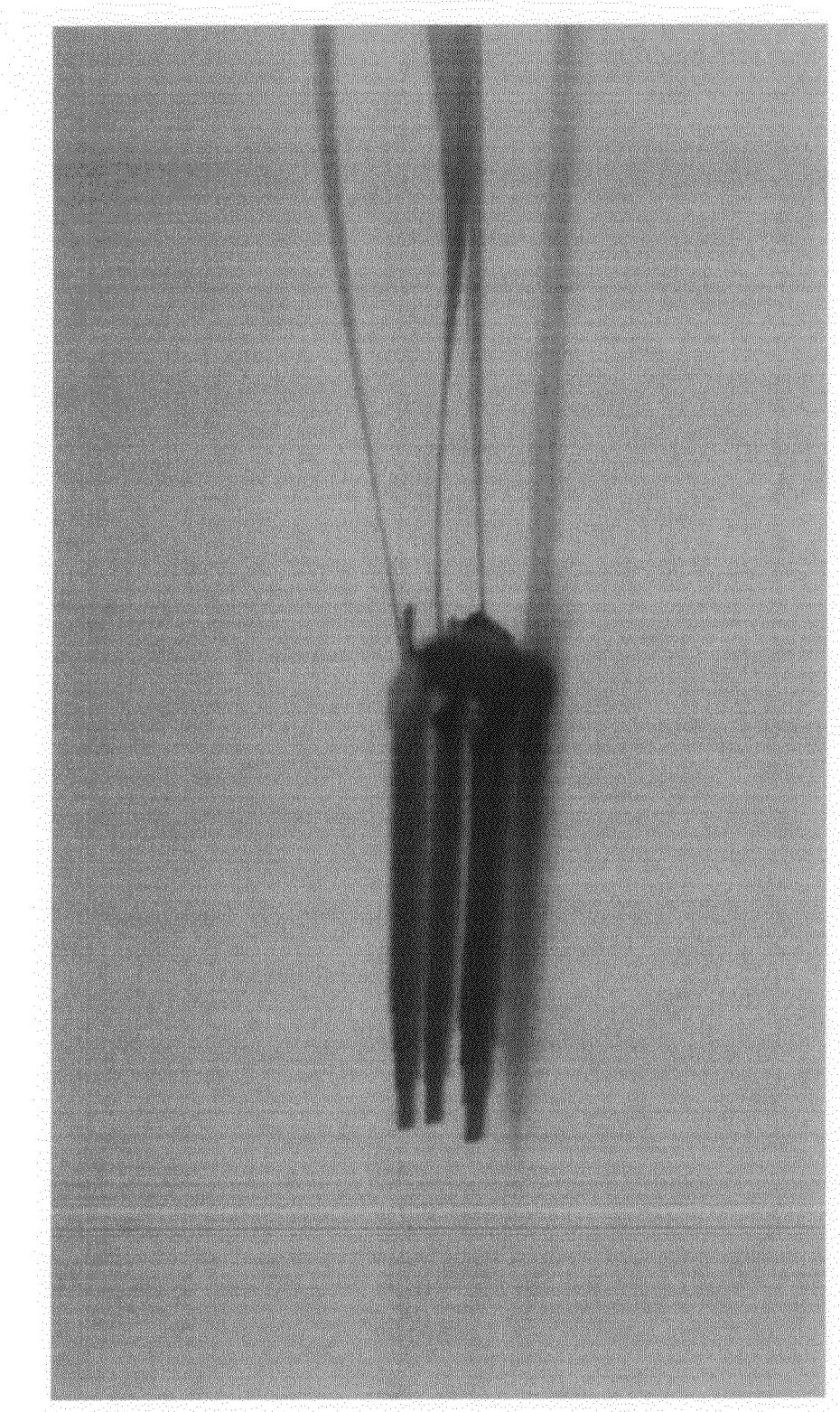
FIG. 7 illustrates the probe stacking capability of the silicon probe structure, which in the embodiment shown comprises three 32 channel probes stacked together to form a 96 channel 3-D structure. The spacing between the probes can be modified.

FIG. 2 shows illustrative an unpackaged cabled silicon probe and its bonding interface. These devices can be expanded to 3-D 32N channel structures by probe stacking of N number of 2D probes, as shown in FIG. 7. Platinum electrodes on each of the eight silicon shanks can be spaced at configurable intervals and two reference electrodes are located on two of the longer shanks. The shank lengths range from 3 mm to 12 mm and are 150 μm thick and 60 μm wide towards the tip of the shank. The tip of the shank forms a 10 degree angle to facilitate the insertion into the brain.

Figure 8:
FIG. 8 illustrates the proximal bonding of a commercial connector with parylene cable connector pads. The left panel illustrates the connection before bonding, and the right panel, after bonding with conduction epoxy.
Figure 9:
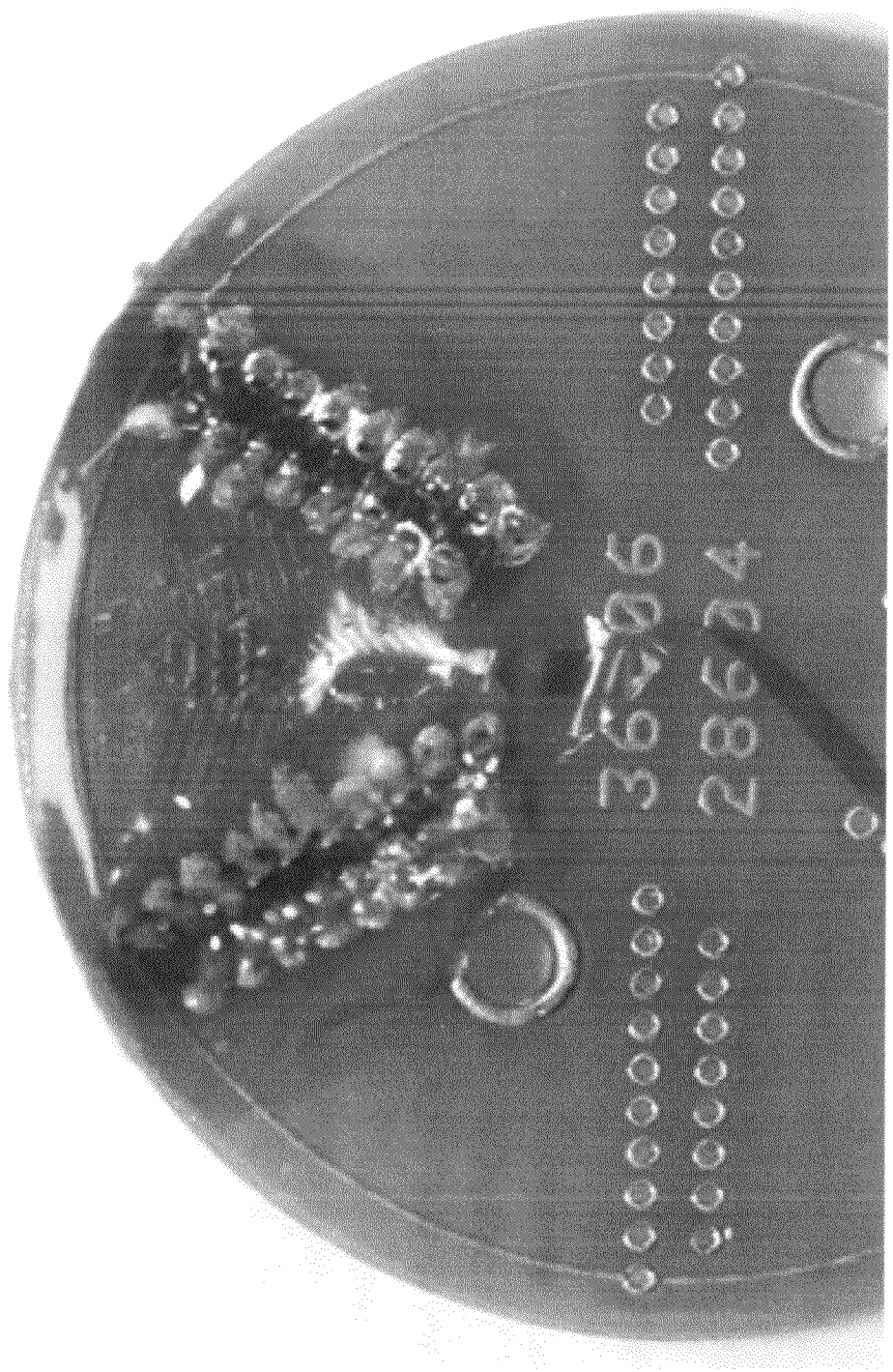
FIG. 9 illustrates a bonding interface of the connector pads on the silicon probe device and the commercial connector through a custom PC board.
Figure 10:
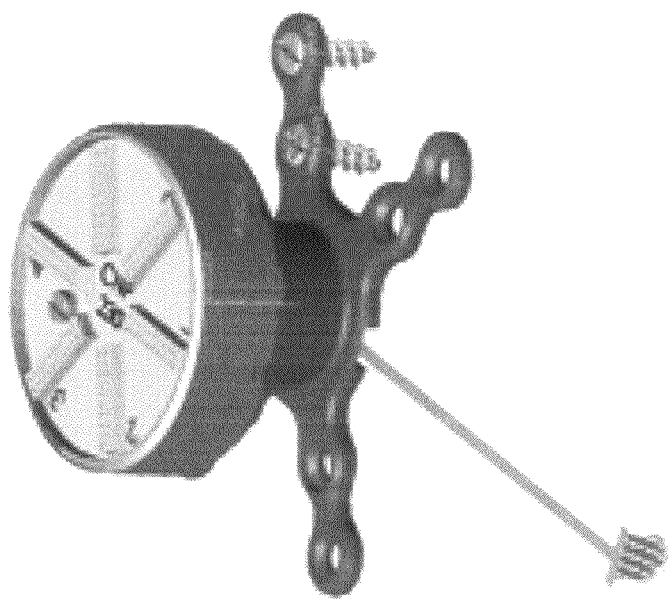
FIG. 10 is a schematic diagram of the packaged silicon probes. The design shows a 96 channel device having three 32 channel devices. The legs of the titanium pedestal are secured to the skull with bone screws.

FIG. 2, FIG. 8 and FIG. 9 show the bonding interface for connecting a cable to external connection points. In one embodiment, the circular platinum rings arranged in a 60 degree Y shape pattern on the end of device are used to electrically bond to commercial available connectors with conductive epoxy on a circular PC board. The 7 cm long parylene cables are 15 μm thick and have 34 traces lines of 10 μm wide and spaced 10 μm apart connect the distal electrodes directly to external connectors, for example as shown in FIG. 10.

Probe Fabrication

Figure 11:
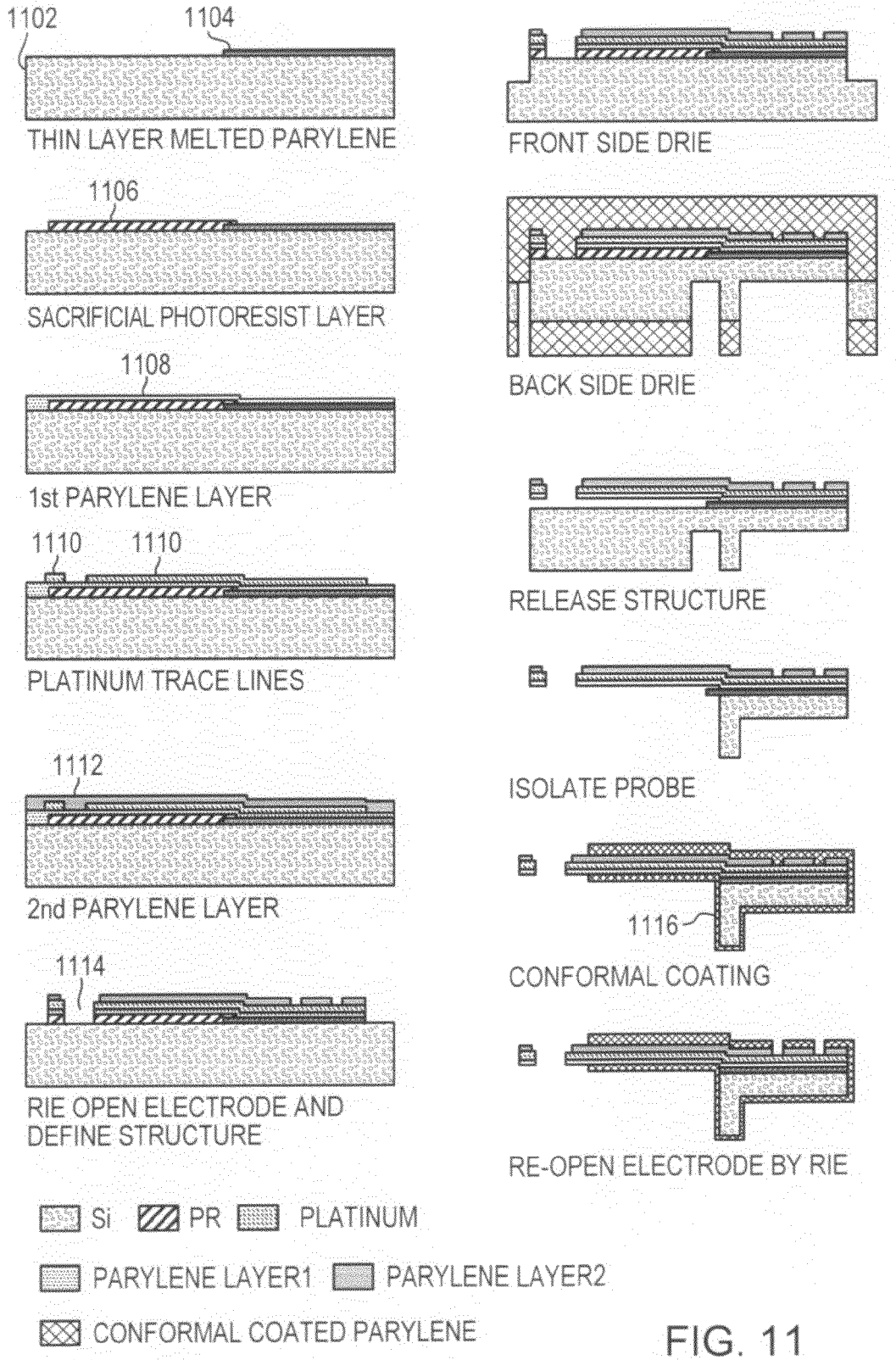
FIG. 11 illustrates probe fabrication process steps
Figure 12:
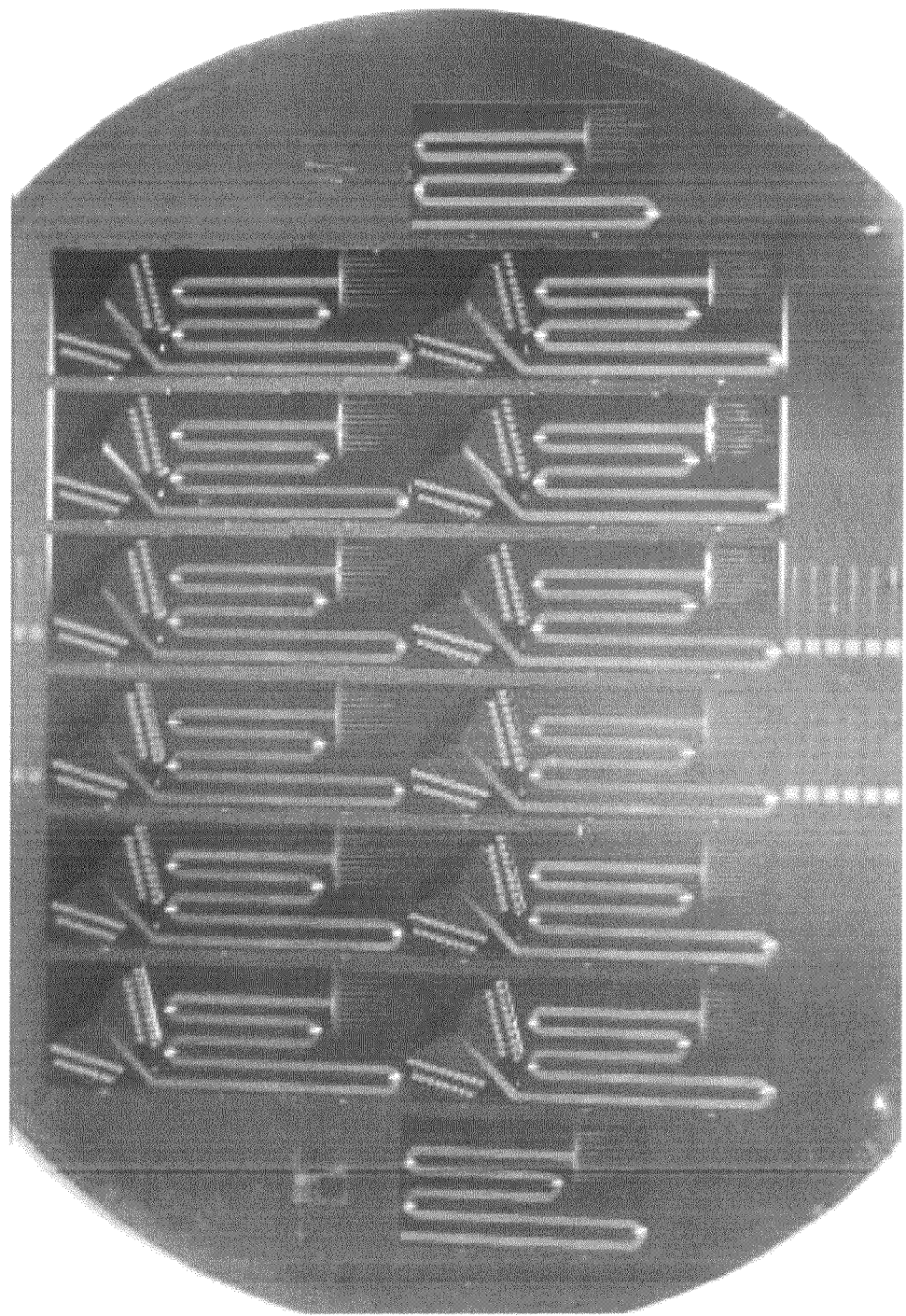
FIG. 12 shows a process wafer after top layer parylene deposition has been performed.

The high density silicon probes are fabricated on double side polished wafers with DRIE (Deep Reactive Ion Etching) technology. FIG. 11 shows the steps performed in carrying out the probe fabrication process. First, a layer 1104 of 0.5 μm of parylene C is deposited on one side of the double side polished wafer 1102 and is melted in an oven at 350° C. The parylene layer 1104 is then patterned by oxygen plasma to leave areas for adhesion enhancement between the parylene/silicon interface. A sacrificial photoresist layer 1106 of 1 μm thickness is then coated to facilitate the final release of the device. A layer 1108 of parylene C (6.5 μm) is then deposited. This is followed by a layer 1110 of lift-off electron-beam evaporated platinum (0.25 μm) to define the trace lines, the electrodes and connector pads. The top layer 1112 of parylene C (6.5 μm) is deposited to complete the parylene-metal-parylene sandwich structure (see FIG. 12). Electrode sites and the device definition are then etched by a two step RIE with $O_2$ Plasma process. Silicon probe shanks (on the right side of each panel of FIG. 11) are subsequently defined and etched by DRIE from both sides of the wafer. The bottom DRIE etching duration defines the thickness of the probe. By depositing and painting protective photoresist die by die, the thickness of every probe on the wafer can be controlled very precisely. The devices are then released in photoresist stripper to provide structures as shown in FIG. 1, and coated on all sides with parylene 1116. Finally, the pads corresponding to the electrodes are opened and the device is annealed at 200° C. for two days to bond the sandwiching parylene layers.

Figure 5:
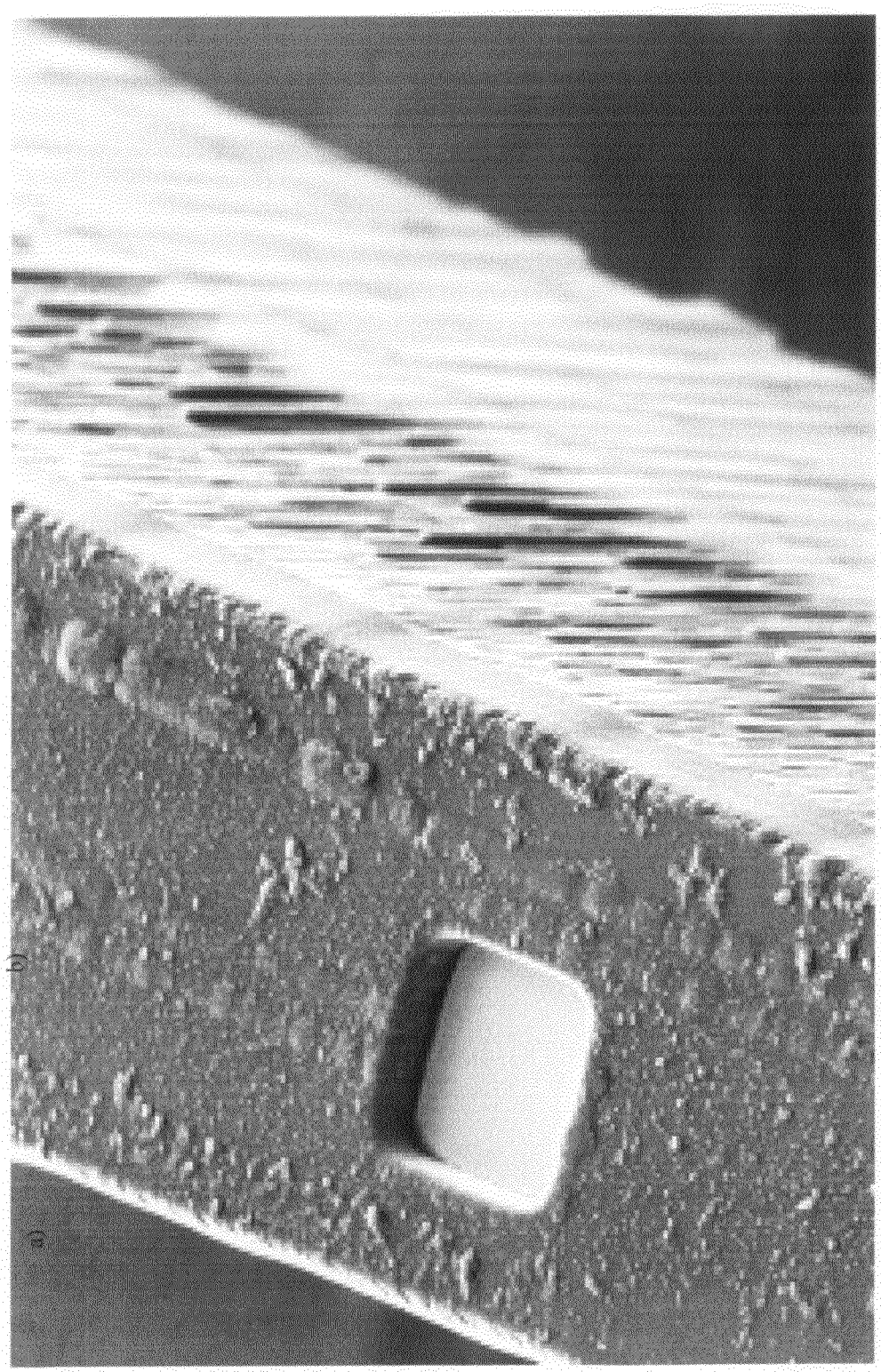
FIG. 5 is an illustrative SEM picture of an electrode.
Figure 6:
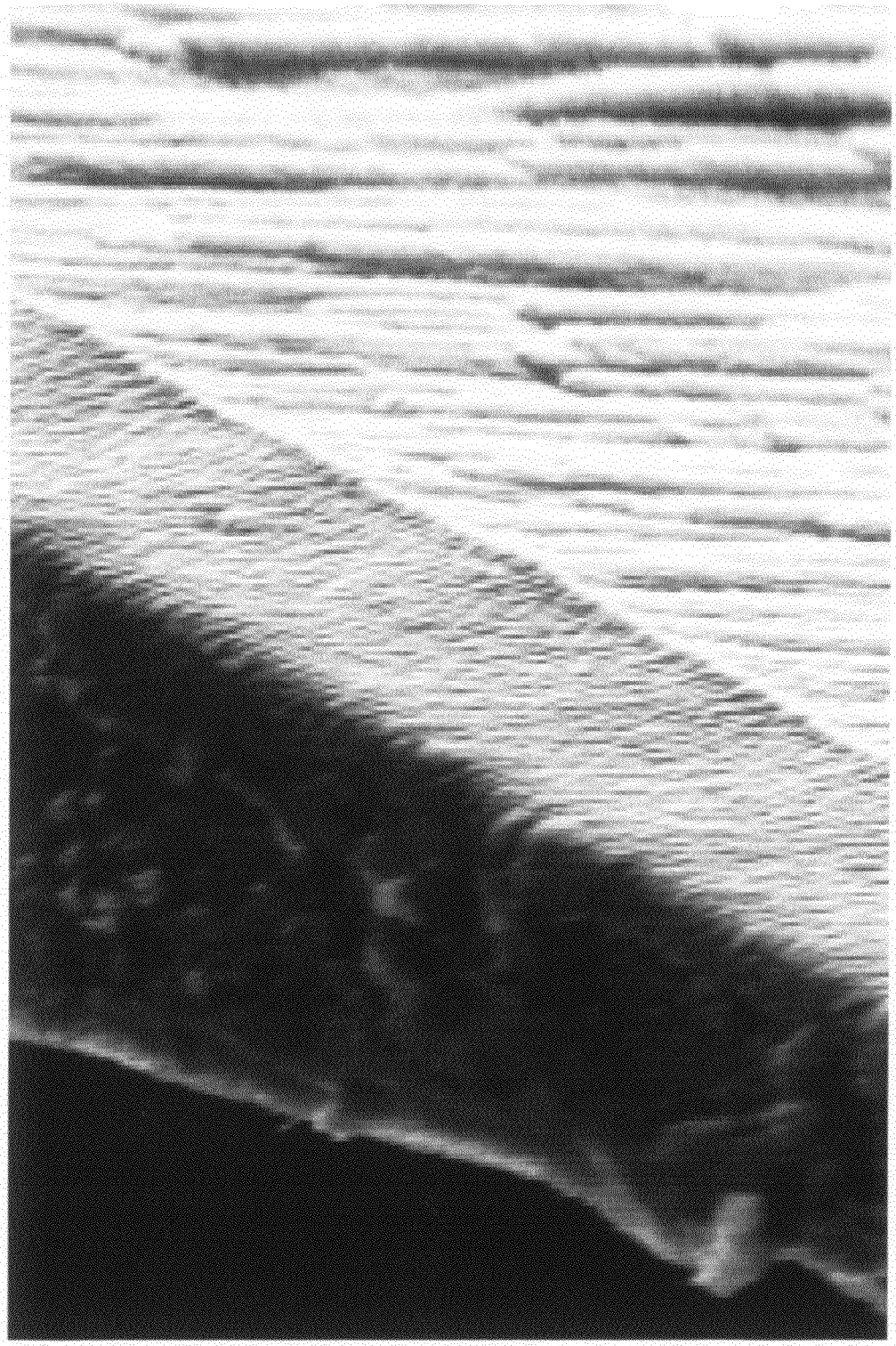
FIG. 6 illustrates sidewall etching after the final opening of the electrodes after total coating.

The total coating of the probe and the cable was done by covering the connector pads with hand-painted photoresist and conformal coating 1 μm of parylene C over the entire device. The device is covered with photoresist again to protect the cables and the rest of the device, leaving the silicon probe section exposed. This structure is then etched directionally with RIE to re-open the parylene coated electrodes, as shown in FIG. 5. This device is later released in acetone and photoresist stripper solution. The silicon probe was dipped into a silicon etchant after the RIE etching to test for total coating. The silicon was not etched after 1 minute of dipping, which validates the coating is still intact and thus full biocompatibility is achieved.

In previous versions of the device, $XeF_2$ was used to roughen the surface of silicon substrate to enhance the mechanical adhesion of the parylene/silicon interface. However, due to the isotropic nature of $XeF_2$ etching of silicon, the depth, undercut and the shape of the resulting surface becomes hard to control. This may result in broken metal lines as well as thermal stress cracks on the border lines during the high temperature electron beam evaporation of platinum. The melted parylene alternative was used to enhance the adhesion of the desired area.

Device Test and Operation

Device testing was performed in three phases: in-vitro measurements in saline solution, in-vivo probe penetration testing and accelerated life testing.

Figure 13:
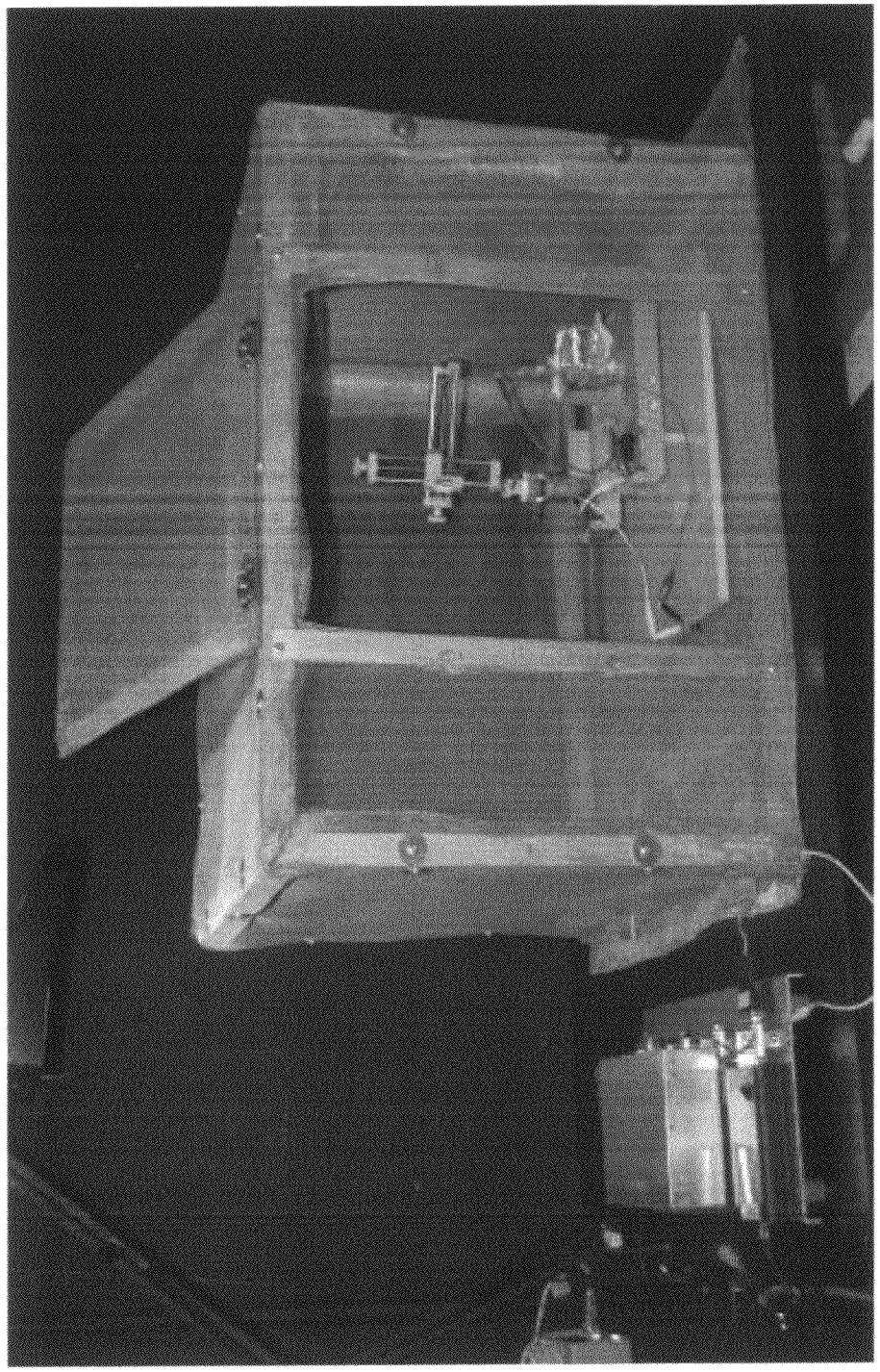
FIG. 13 illustrates an in vitro testing setup. The metal box on the left hand side is a pre-amplifier. The x-y stage in the Faraday cage maneuvers the probe into the saline solution.
Figures 14, 15:
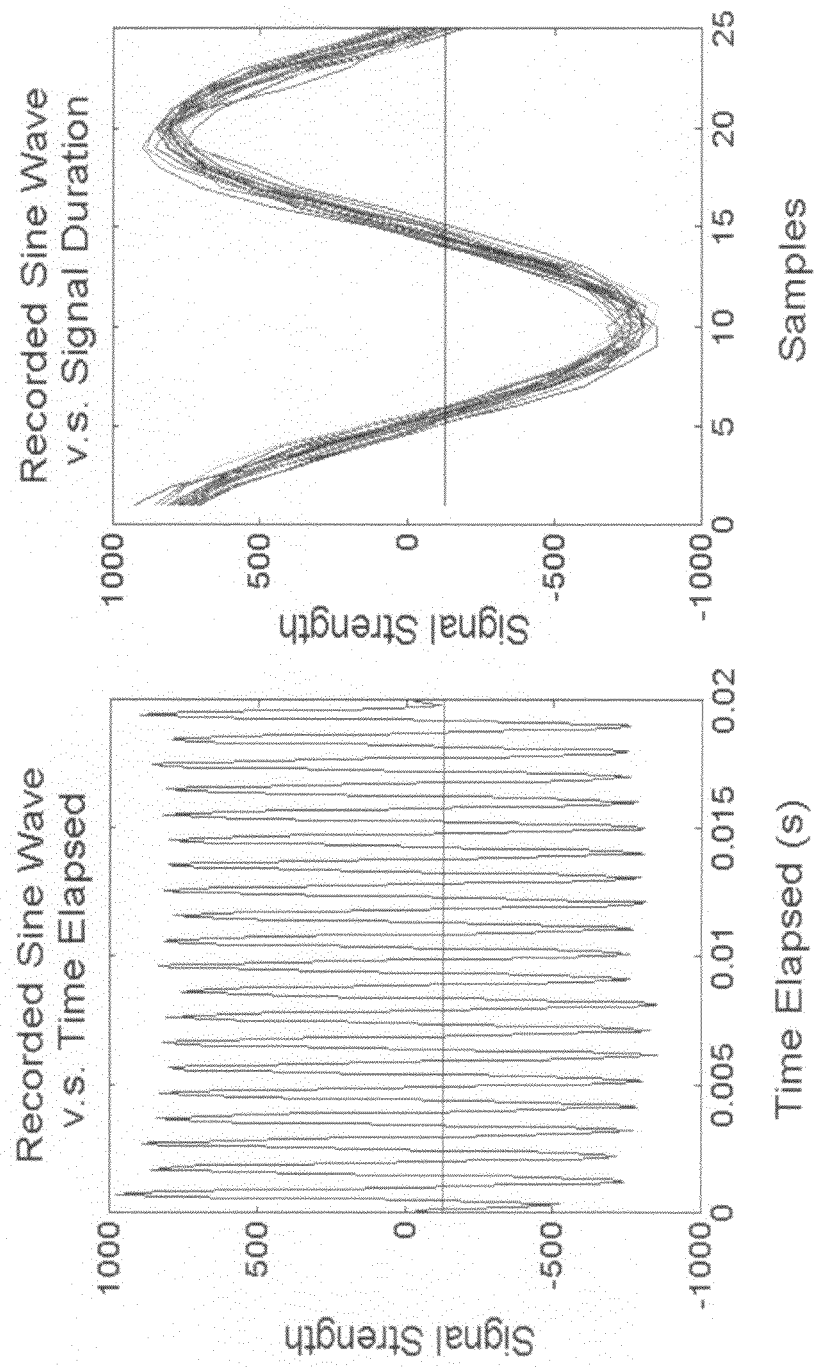
FIG. 14 illustrates a sine wave applied across a saline solution as it is recorded with the silicon probe.
FIG. 15 is a diagram showing threshold aligned waveforms. The horizontal axis is the number of samples taken at the rate of 20,000 samples per second for a duration of 1.2 ms. The vertical axis represents the signal strength corresponding to a sinusoid with amplitude (above baseline) of 400 μV.
Figure 16:
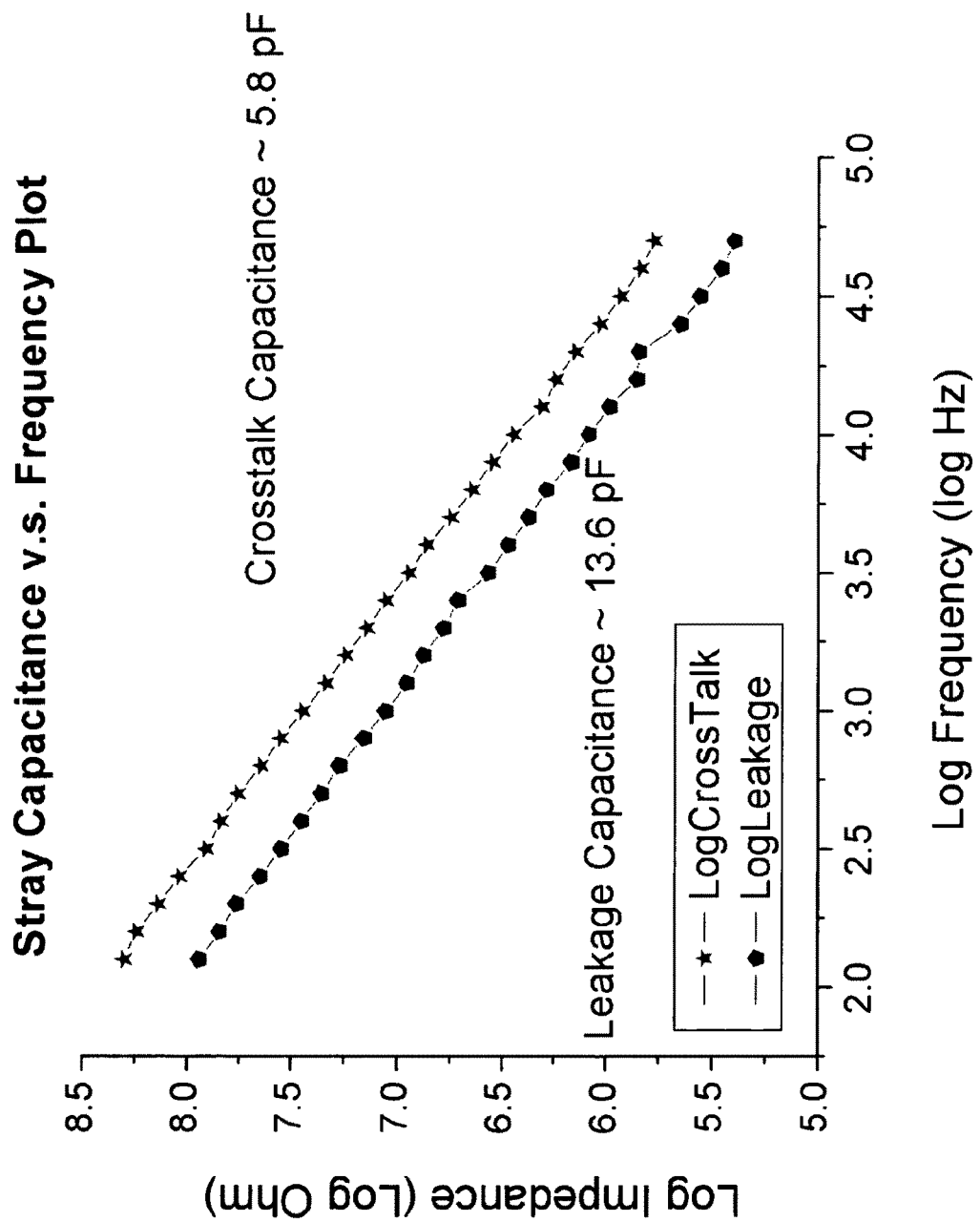
FIG. 16 is a diagram showing stray Capacitance with cross talk (relative to neighboring traces) and leakage capacitance (relative to saline). Only the cable was immersed into the solution.

In the first phase, we used the setup shown in FIG. 13 to conduct in-vitro impedance tests with channel electrodes having mean dimensions 22 μm×22 μm. The measured distribution of areas of these electrodes was determined to lie within ±9.1 μm² of the nominal value under SEM measurements. Impedance measurements of channel electrodes resulted in values of 670 kΩ±33 kΩ at 1 kHz whereas the reference electrodes with areas approximately 25,000 μm² resulted in impedances in the range of 20 kΩ. To test the electrode's ability to pick up signal different signal types, sine waves and pre-recorded action potentials were applied across a saline solution and were successfully recorded with the fabricated electrodes, as illustrated in FIG. 14 and FIG. 15. Impedance tests were also performed on the parylene flexible cable to determine the stray capacitances. Results presented in FIG. 16 show a clear linear relationship on a log-log scale, which allows us to derive the impedance of the cross-talk and the leakage to be approximately 27.4 MΩ and 11.7 MΩ respectively at 1 kΩ

In a second set of operational tests, the devices were inserted through the pia and into the cortex of live rats to test penetration ability. Results show a full insertion of the probe was successful without any bending, buckling or breakage by observing the shanks under a surgical microscope during insertion.

Figure 17:
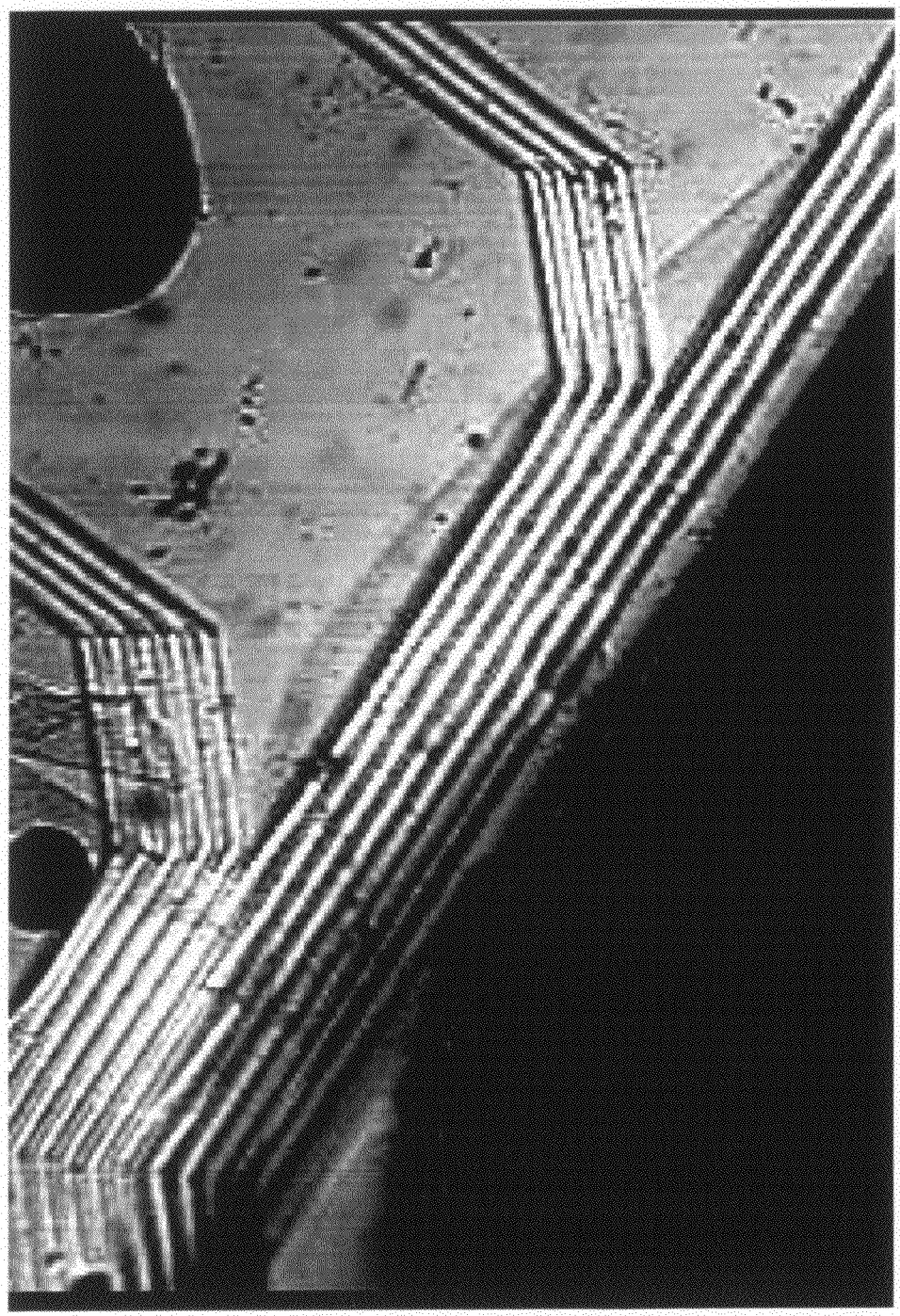
FIG. 17 illustrates delamination that occurred after five weeks of soaking in 90° C. saline solution. The probe was still attached on the parylene cable after eight weeks of soaking.
Figure 18:
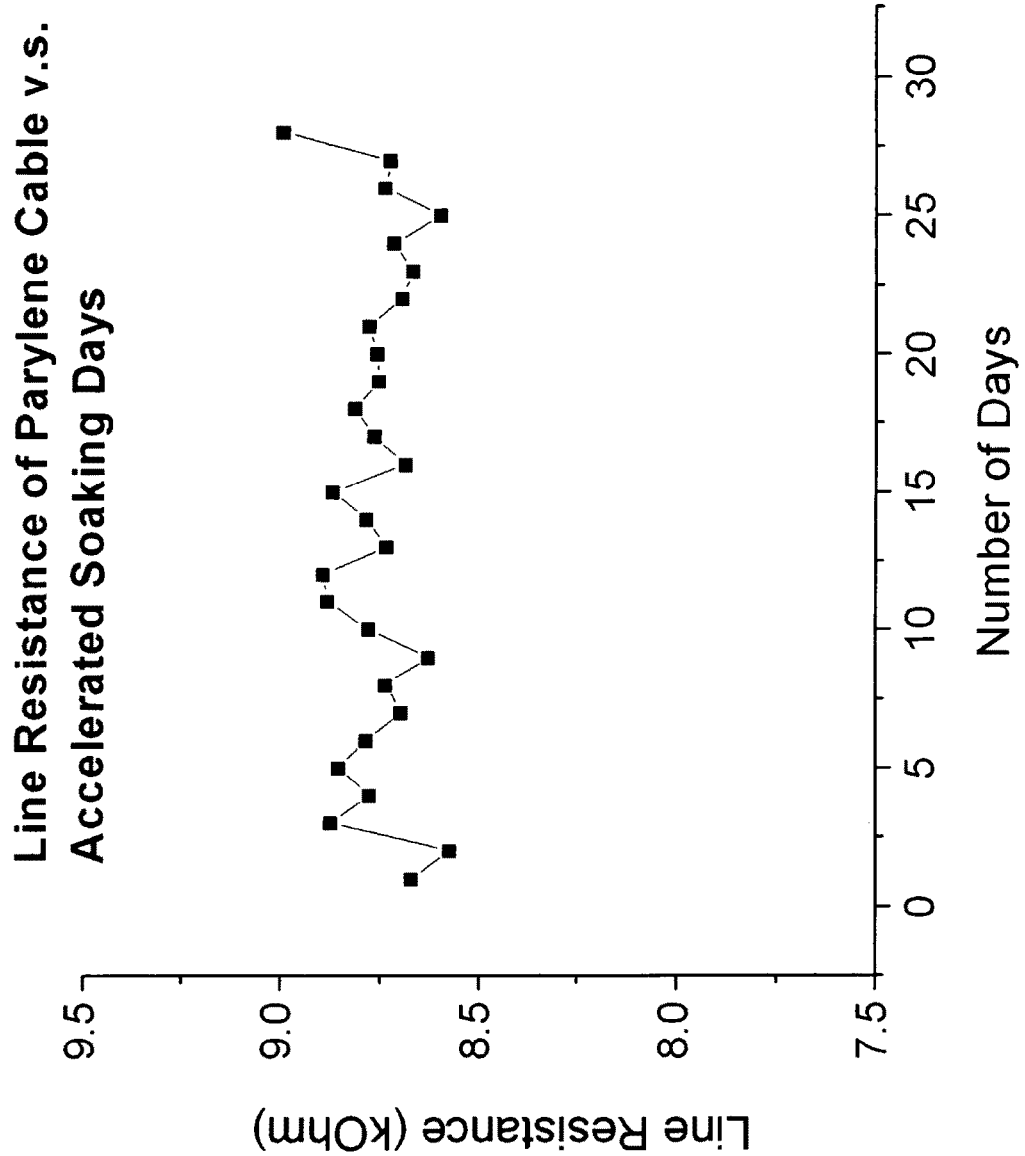
FIG. 18 is a diagram illustrating that a parylene cable had substantially the same line resistance after four weeks of soaking in 90° C. saline.

Finally, the devices underwent accelerated life testing in saline to determine the mean time to failure. Failure modes include the failure of the silicon to parylene adhesion as well as the delamination between the parylene layers. Soaking test results illustrated in FIG. 17 show that the parylene-silicon adhesion is able to withstand more than five weeks in 90° C. saline before delamination occurs. Furthermore, the parylene cable quality is uncompromised for the four weeks of soaking in the same environment with a cable only device, as illustrated in FIG. 18.

We have developed and performance tested a fully parylene C encapsulated, high electrode density silicon based array with an integrated flexible cable. A 3-D packaging scheme with commercial connectors and a percutaneous pedestal is also presented. Electrode impedances were characterized and pre-recorded action potentials were recorded through these devices. In vivo insertion capability of the silicon probes have also been verified. High temperature accelerated life time testing in saline indicates the stability of both the cable and the probe-cable interface for more than four weeks in 90° C. saline. From the testing results, this high density silicon probe is a neural probe that is expected to be useful in chronic cortical prosthetic applications.

We now describe a packaging technique that utilizes a simple, flexible parylene pocket that can accommodate and make connection to a chip, the pocket being supported on a silicon substrate with metal pads. This pocket can house an IC chip or a discrete component inside and provide electrical connections to it. We also demonstrate an 8-shank silicon probe array integrated with a fully functional 16-channel amplifier CMOS chip.

Parylene Pocket Design

Figure 19:
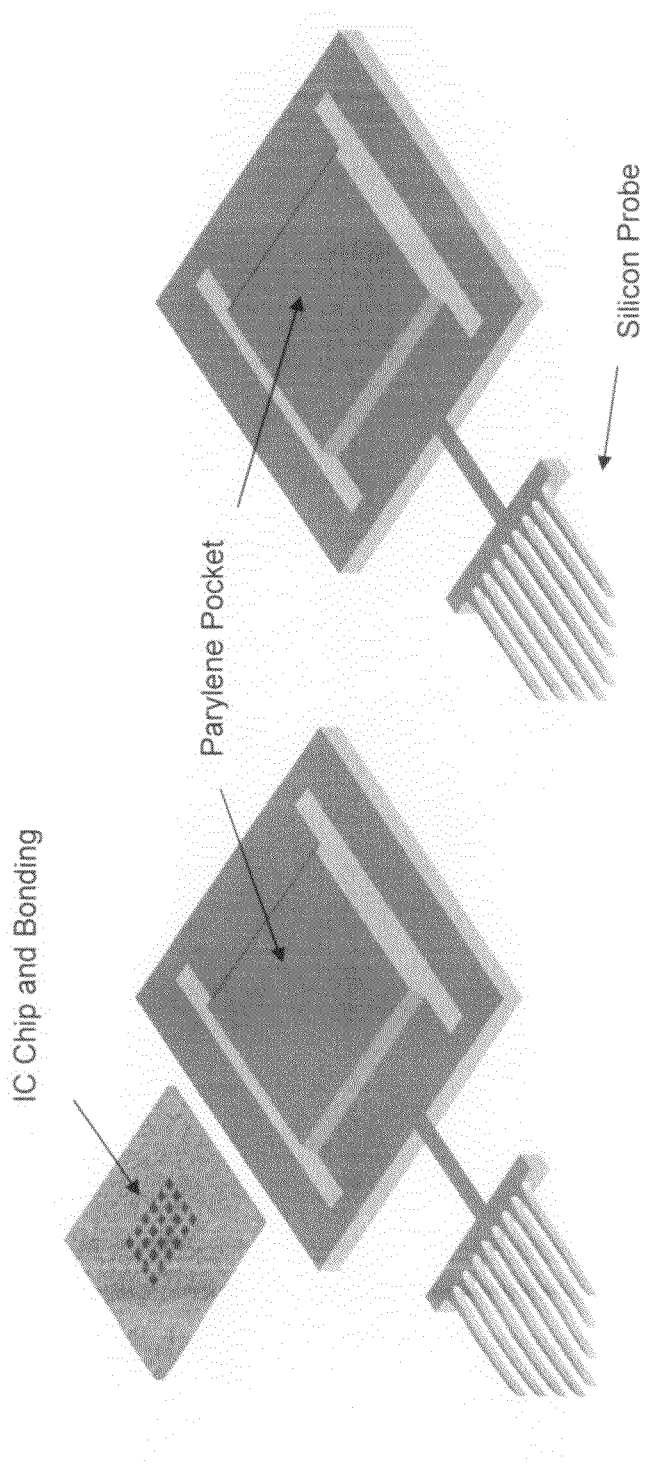
FIG. 19 illustrates a parylene pocket with a signal processing chip, showing on the left an IC chip prior to insertion into the pocket, and on the right a complete packaged pocket structure. In some embodiments, the chip may be powered through an RF coil, as shown hereinbelow.

A totally biocompatible packaging/integration solution to embed amplifiers near the recording sites would be advantageous. Desirable and advantageous criteria for a well-packaged device for implantation would include avoidance of infections and inflammatory responses; the ability to withstand the harsh physiological environment of the human body (or an animal body); ease of fabrication; and as low a cost as possible. We describe a new packaging technique that utilizes a flexible parylene pocket on silicon substrate with metal pads. This pocket can house an IC chip and provide electrical connections to it, and can be totally integrated with silicon probes. By application of this technology, one can make the chips and probes separately and later package them together, which is an advantage in IC/probe integration. The pocket size and the configuration of the electrodes can be modified to suit different chips and applications and is not sensitive to dry etching flatness. FIG. 19 shows the drawing of a wireless parylene pocket integration scheme. The whole bonding structure is conformally coated and sealed with parylene-C (poly-para-xylylene-C), and with medical grade epoxy to achieve total encapsulation for biocompatibility. We are able to fabricate IC-cabled packages that are highly customizable, fully biocompatible, and easy to mass fabricate.

The parylene pockets presented now have been designed to accommodate a 300 μm thick, 0.5 mm×0.5 mm sized commercial IC chip. The parylene C cable and pocket thickness is 12 μm with gold metal connection traces embedded. It is believed that gold electrodeless plating is an alternative pad-to-pad interconnection technique. The two openings on two sides of this pocket were designed to provide stress relief during the insertion. The edge of the pocket has a 1 mm wide melted parylene adhesion layer section to provide the adhesion between the parylene and the silicon substrate.

Figure 20:
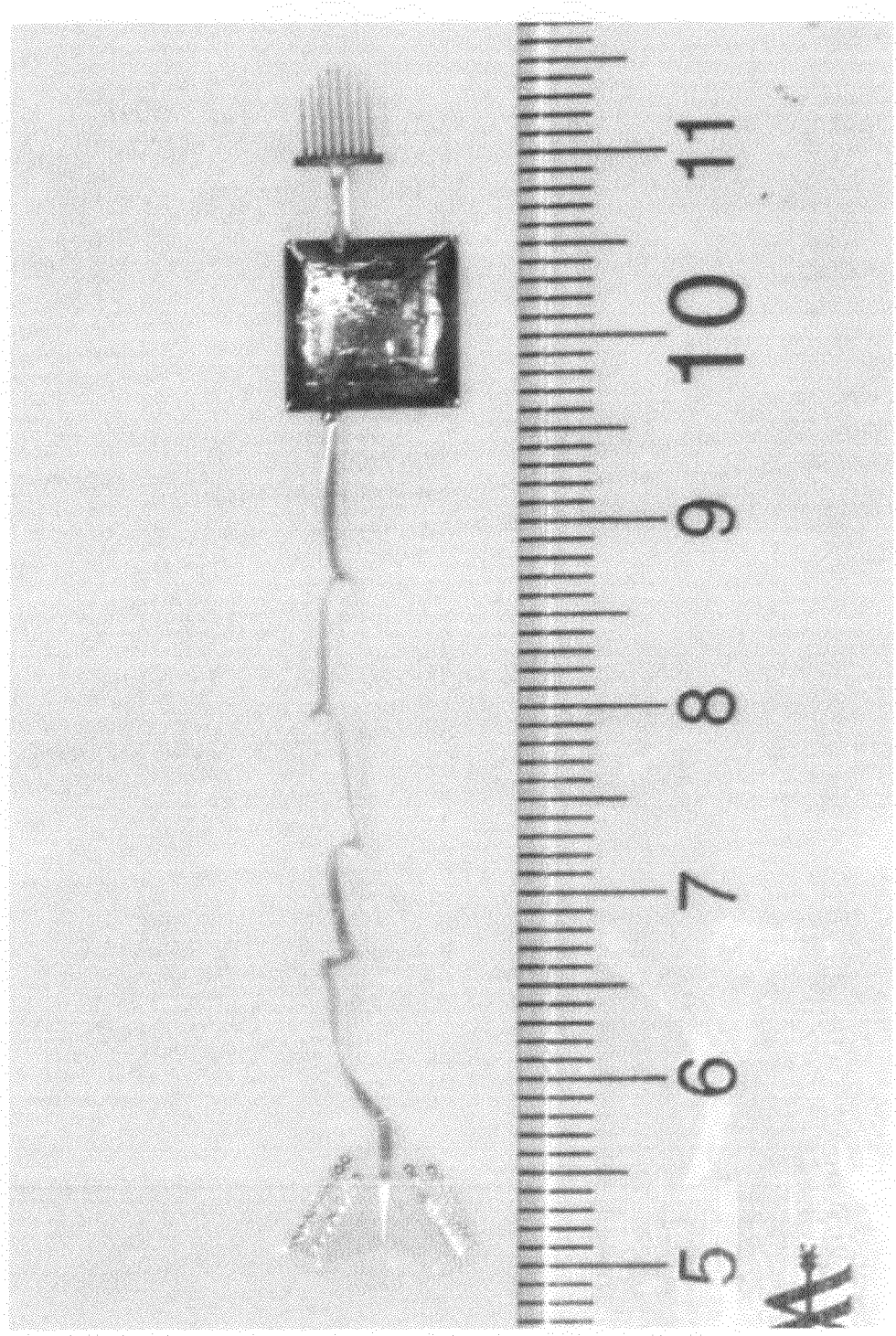
FIG. 20 illustrates a silicon probe integrated with a parylene pocket containing a conduction chip that has been inserted to demonstrate the functionality of the integrated pocket structure. This device has been totally coated with parylene and sealed with epoxy.
Figure 21:
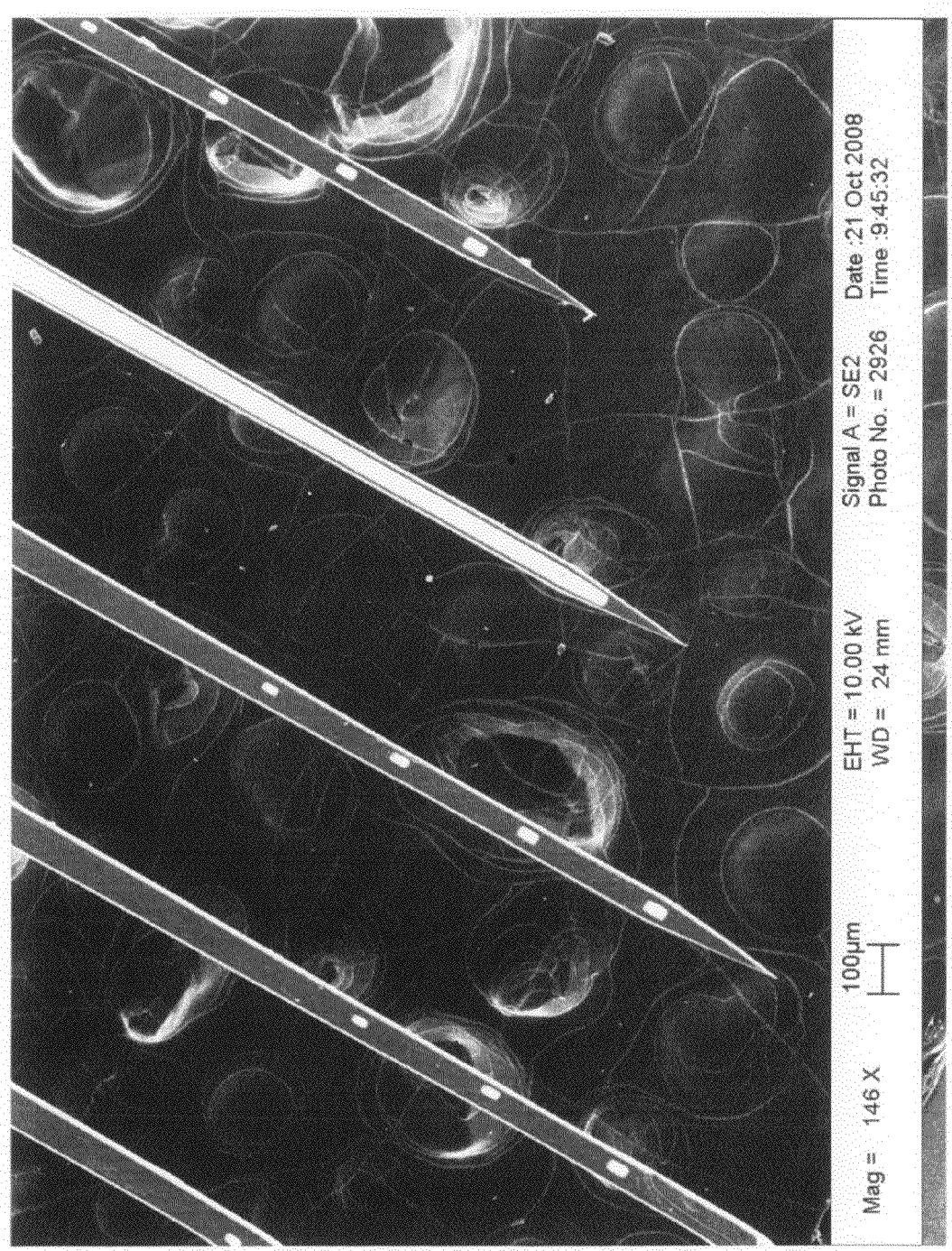
FIG. 21 is an SEM picture of the silicon shank with electrodes.

This structure also comprises a parylene pocket integrated with a 2-D 32 channel flexible cabled electrode array device shown in FIG. 7), which can be expanded to 3-D 32×N channel structures by probe stacking. The silicon base of the pocket is 0.8 mm×0.8 mm in size and is 500 μm thick. In one embodiment, the parylene pocket is connected to a 7 cm cable with a 60 degree Y shape pattern at the end, as illustrated in FIG. 20. These are circular platinum rings arranged to be electrically bonded to commercial available connectors with conductive epoxy on a circular PC board. The silicon shank is 150 μm thick and has length of 5.1 mm, 4.6 mm, 4.1 mm and 3.6 mm from longest to shortest, respectively, as shown in FIG. 21.

Parylene Pocket Fabrication

Figure 22:
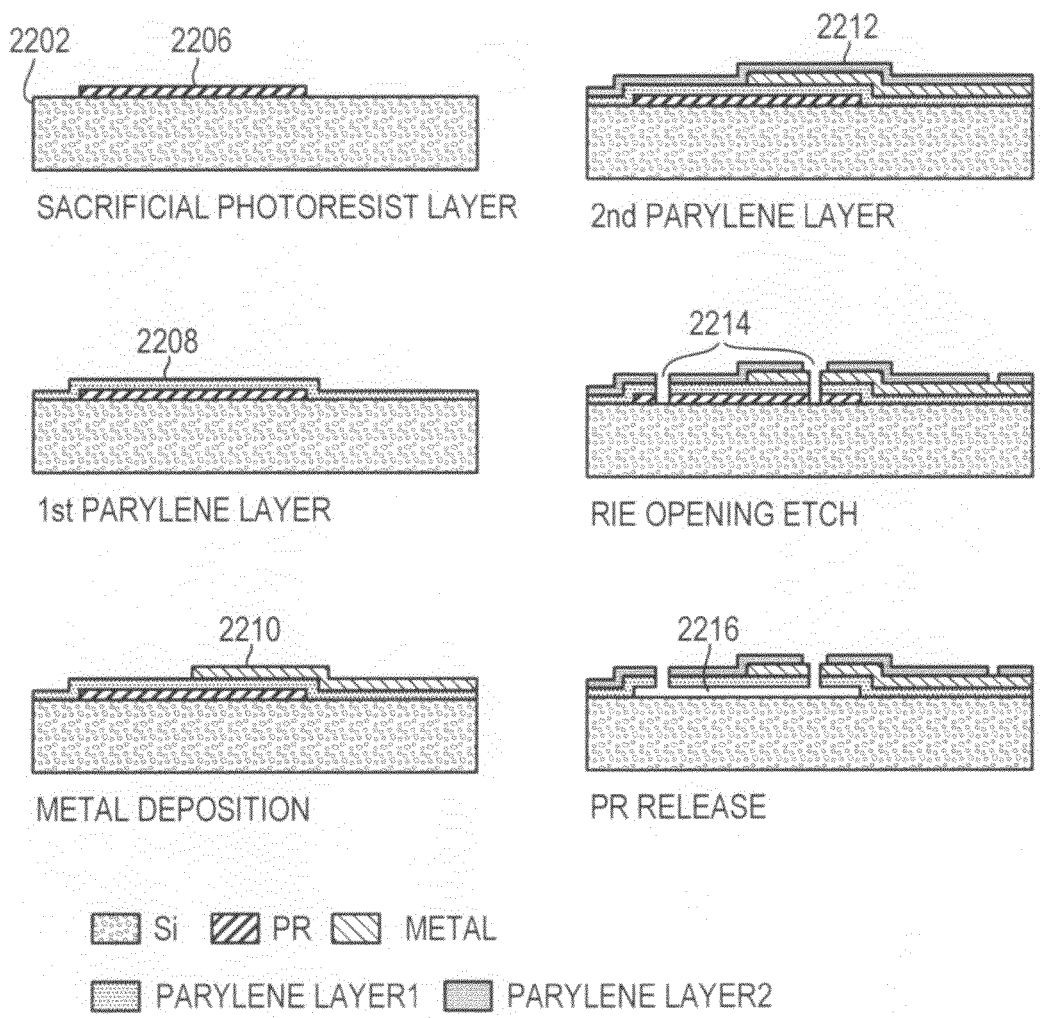
FIG. 22 is a diagram in cross-section illustrating the fabrication process steps used to prepare a parylene pocket. These steps can be integrated with the fabrication of parylene-cabled silicon prosthesis probes.

The parylene pocket structures are fabricated on double side polished wafers with DRIE (Deep Reactive Ion Etching) technology. FIG. 22 shows the fabrication process.

Figure 23:
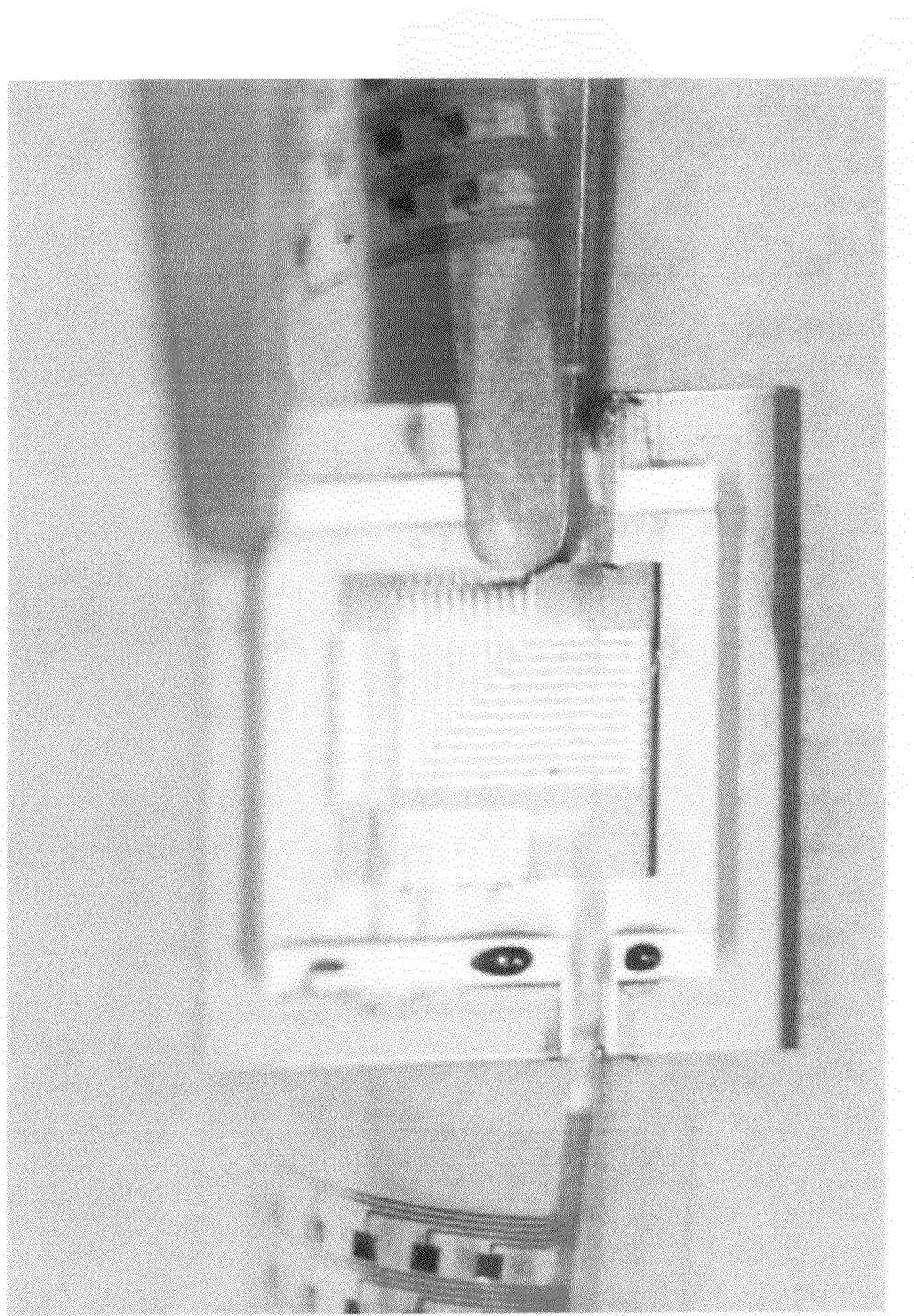
FIG. 23 illustrates the insertion of the IC chip into the parylene pocket. In one embodiment, tweezers are used to align the bonding pads to the metal pads on the chip as they are observed using a microscope.
Figure 24:
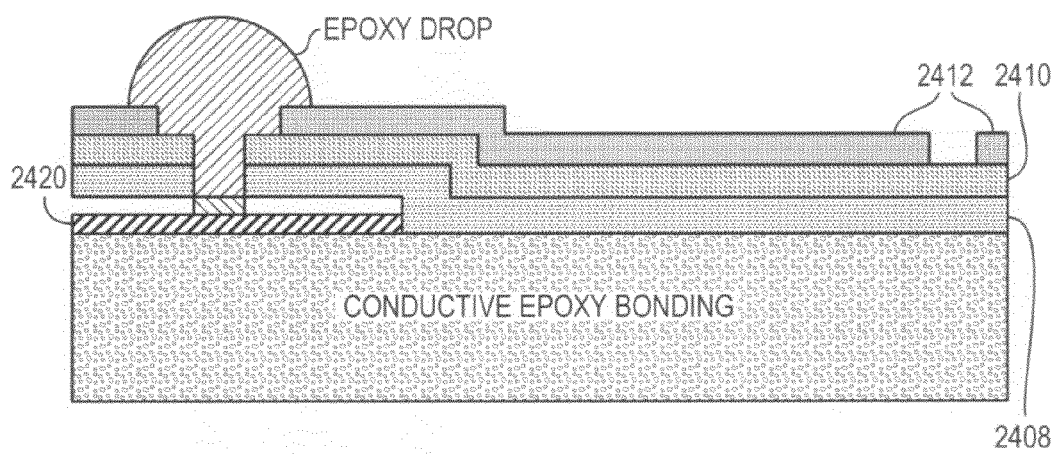
FIG. 24 illustrates a bonding scheme for the parylene pocket. A drop of conductive epoxy is applied through the bonding hole, so that the epoxy contacts the metal pads on the IC chip underneath. The drop of the conductive epoxy can be controlled to 200 μm by hand application.
Figure 25:
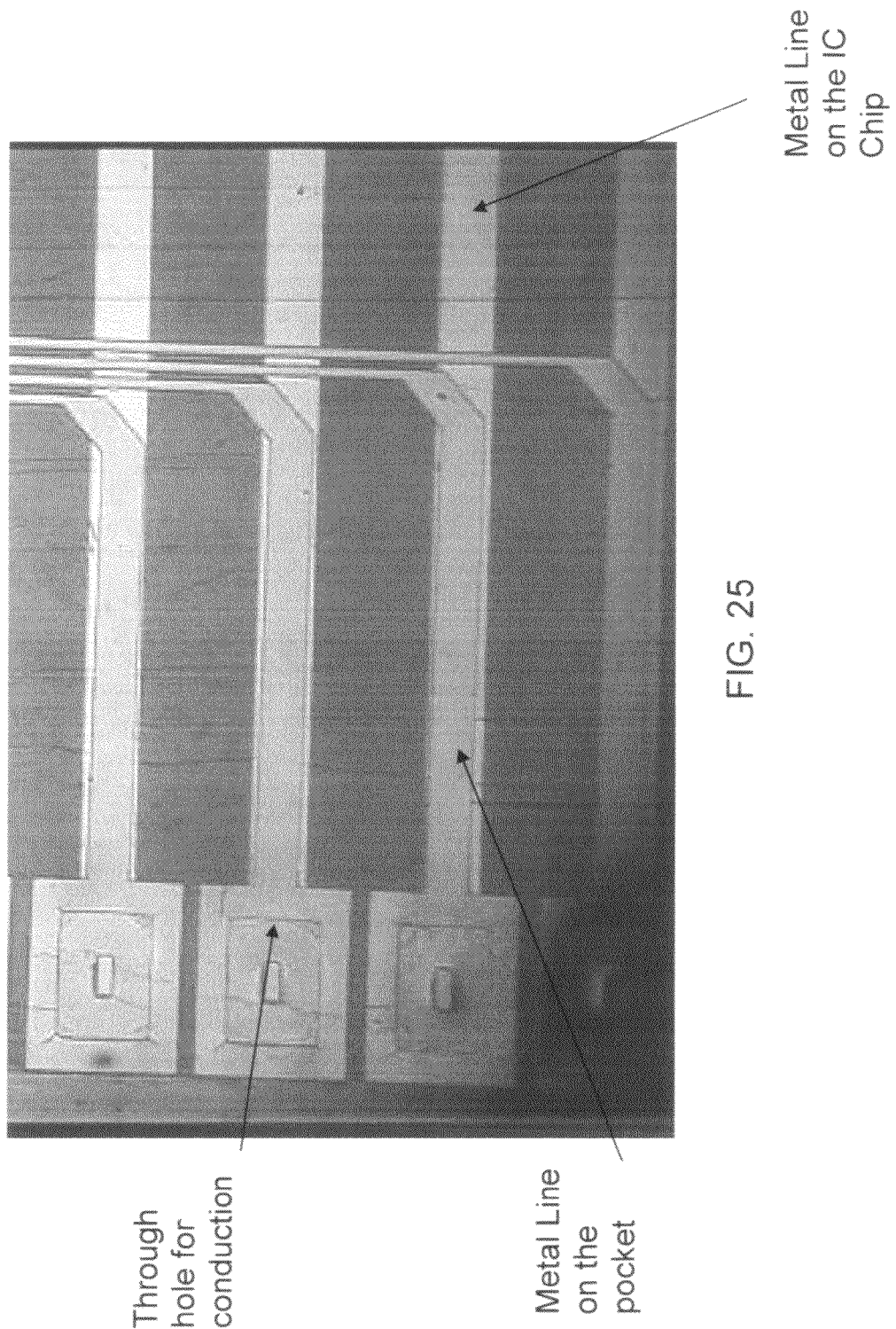
FIG. 25 illustrates the alignment of the pads on the parylene pocket and the metal lines on the inserted chip. The alignment offset was on the order of 10 to 20 μm.
Figure 26:
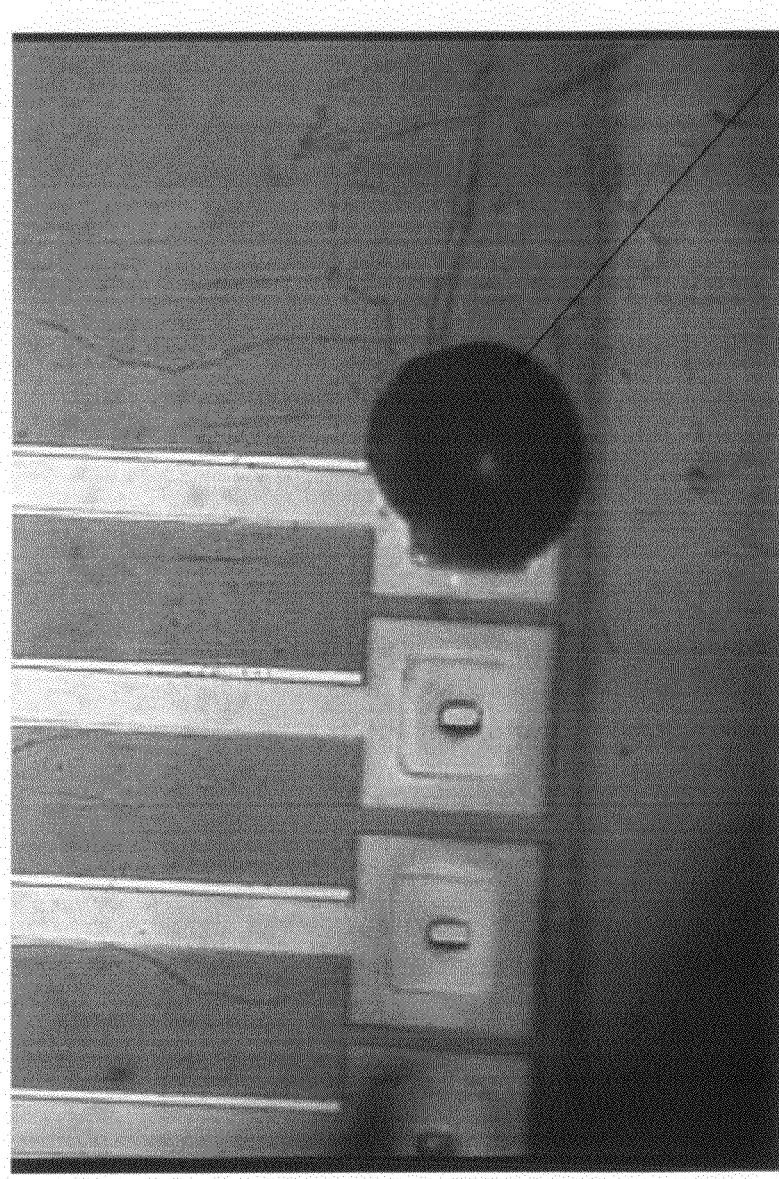
FIG. 26 shows a drop of biocompatible conductive epoxy that was applied over the metal pads to provide electrical conduction. The size of the drop is on the order of 150 to 200 μm.
Figure 35A:
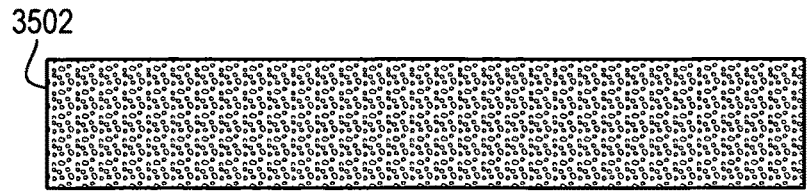
FIG. 35 is a diagram in cross-section showing the steps performed in fabricating a self supporting parylene pocket structure that provides contacts to chips having contact pads on two opposite surfaces.
Figure 35B:
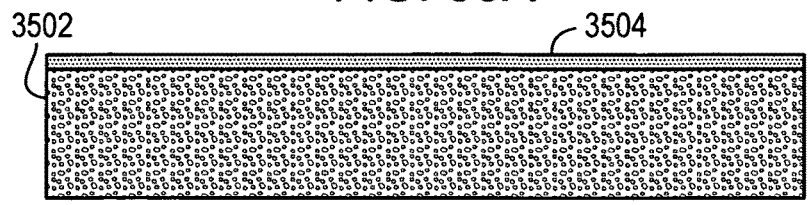
Figure 35C:
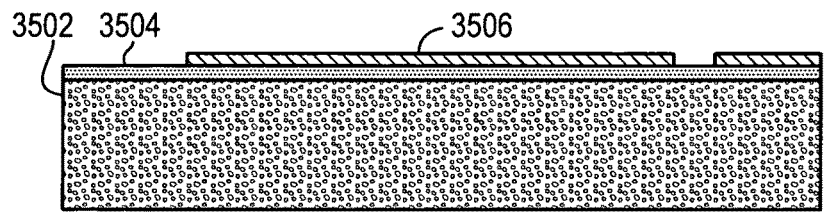
Figure 35D:
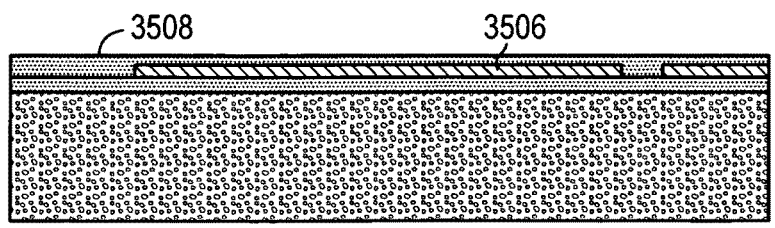
Figure 35E:
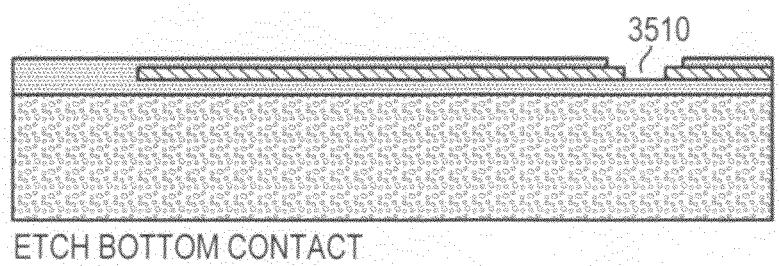
Figure 35F:
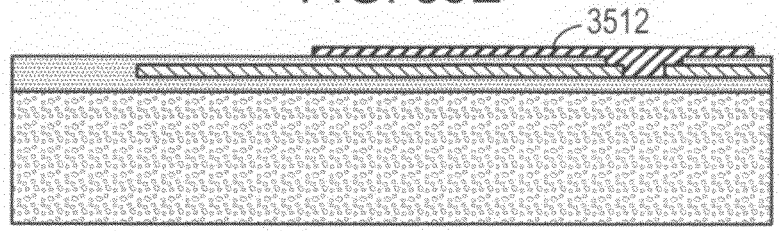
Figure 35G:
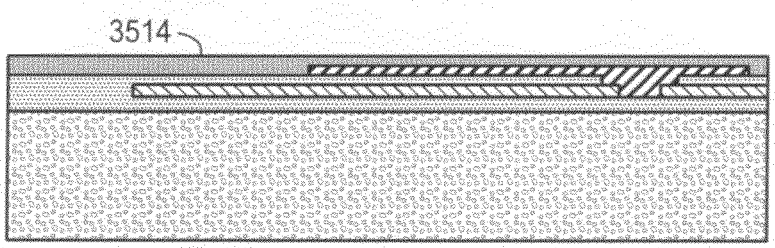
Figure 35H:
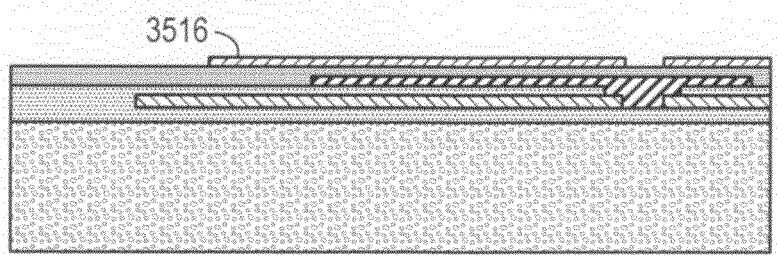
Figure 35I:
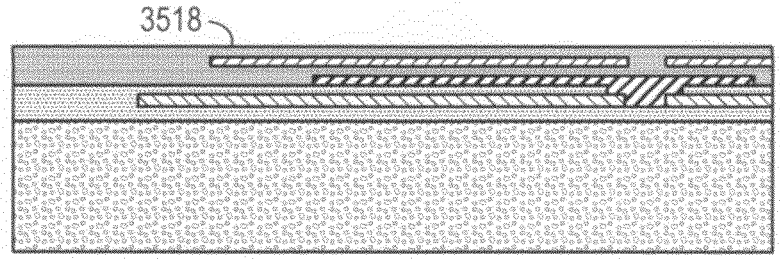
Figure 35J:
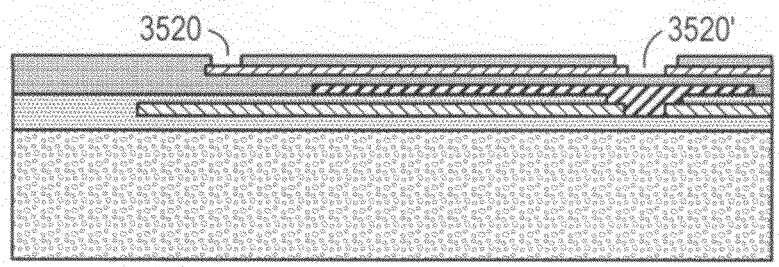
Figure 35K:
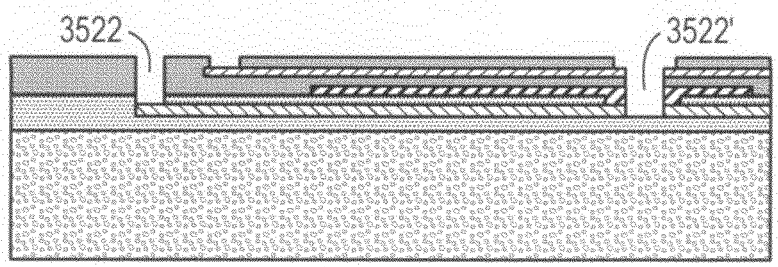
Figure 35L:

On a polished surface 2202 of a silicon wafer, a sacrificial photoresist layer 2206 is spin-coated for pocket releasing. A layer 2208 of parylene-C (6 μm) is then deposited, followed by a layer 2210 of Cr/Au (0.05/0.2 μm) lift-off process with electron beam evaporation to provide electrical connection. The top layer 2212 of parylene-C (6 μm) is deposited to complete the parylene-metal-parylene sandwich structure. Electrode sites 2214, 2214' and the device definition are then opened by a two-step RIE with $O_2$ Plasma (Reactive Ion Etching) process. The outline of the parylene pocket structure 2216 is subsequently etched by DRIE from both sides of the wafer. In the final step, the devices are released in photoresist stripper and dried. The completed open pocket has at least one electrical contact configured to be accessible on an internal surface thereof, as shown in the lowest panel on the right side of FIG. 22, in which open pocket 2216 has opening 2214 on the right through which a conductive epoxy can connect metal layer 2210 to a pad on a chip that is inserted in pocket 2216. As will be seen in other embodiments described hereinbelow (see for example FIG. 32, FIG. 35 and FIG. 47), similar open pockets provided by the invention also have at least one electrical contact configured to be accessible on an internal surface of the pocket. An IC chip is then inserted into the parylene pocket as illustrated in FIG. 23. It is aligned with the traces in the pocket as shown in FIG. 25. The chip 2420 is bonded with conductive epoxy as illustrated in FIG. 24 and FIG. 26 to make electrical connection between a conductor 2410 of the pocket with a selected connection pad or electrical terminal on a surface of the chip 2420. FIG. 24 is an illustrative example that shows a pocket in which a chip 2420 is in contact with a conductive epoxy bonding surface on one side, and situated in a pocket defined by a layer of parylene 2408, a conductive layer 2410, and a second layer parylene 2412. A conductive epoxy drop is placed so as to contact conductive layer 2410 and a conduction pad on the chip 2420. In alternative embodiments, all of the electrical contacts can be made from one side of a chip 2420, or electrical contacts can be made at predefined locations on two sides of a single chip, as illustrated by the pocket structure illustrated in cross-section in FIG. 35L. As appropriate, the structure can be totally coated with parylene-C again for complete encapsulation and to ensure biocompatibility.

Device Testing and Results

Figure 27:
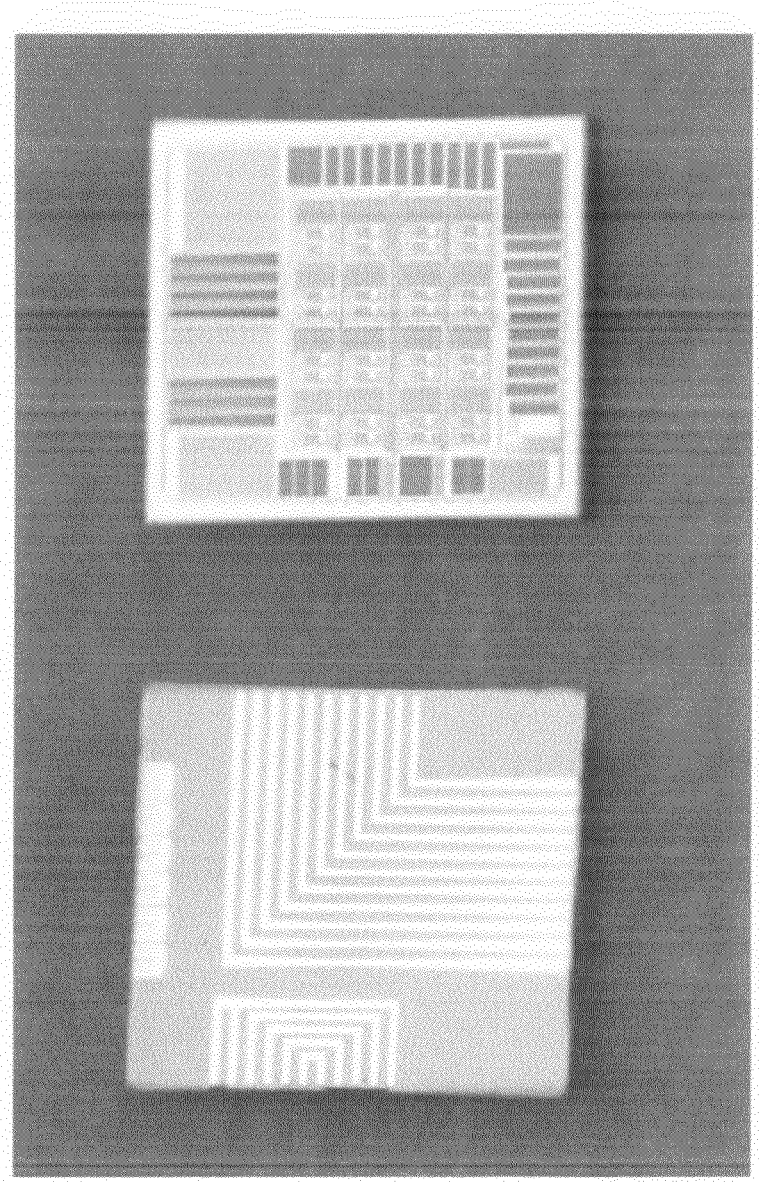
FIG. 27 illustrates a conduction chip on the left and a CMOS amplifier chip (on the right) which are used in the testing of the devices. The metal pads on the conduction chip were made to mimic the metal pads on the amplifier chip.

Device testing was performed in two phases: chip integration testing for both conduction and amplifier chips, which are illustrated in FIG. 27, and accelerated life testing in a saline environment.

Figure 28:
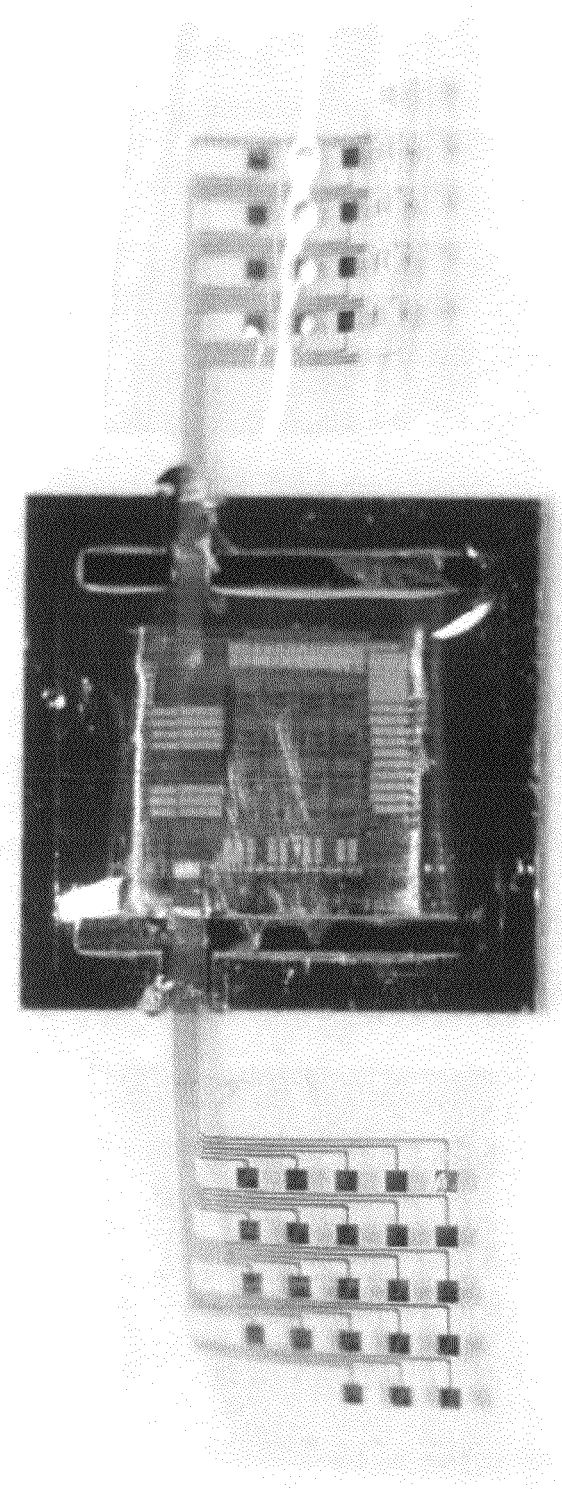
FIG. 28 illustrates a structure having a self-supporting parylene pocket structure. This device is used to test the amplifier chip after bonding.

The embedded CMOS amplifier chip used is a scalable 16-channel pre-amplifier and buffer chip with an in-band gain of 35.5 dB. This chip was tested using a function generator on a pocket only structure, as shown in FIG. 28. Both sine waves and square waves with frequency of 0.5 kHz, 1 kHz, 2 kHz and 5 kHz and amplitude of 5 mV were passed into the chip. The amplified output, shown in FIG. 29, from the oscilloscope concludes a successful functionality testing of our packaging technology. The conduction chip was bonded in a silicon probe integrated pocket and the impedances of the electrodes were measured.

An on-going accelerated soaking life-time test was also performed on the parylene pocket structure to determine the mean time to failure. Testing shows the pocket structure with the embedded amplifier chip sealed by 1.5 mm of biocompatible epoxy is able to function after soaking in 90° C. saline for more than 30 days, which translates to a lifetime of years in saline at 37° C. (normal body temperature), based on the conventional understanding that reaction rates double for every increase in temperature by 10° C.

Figure 30:
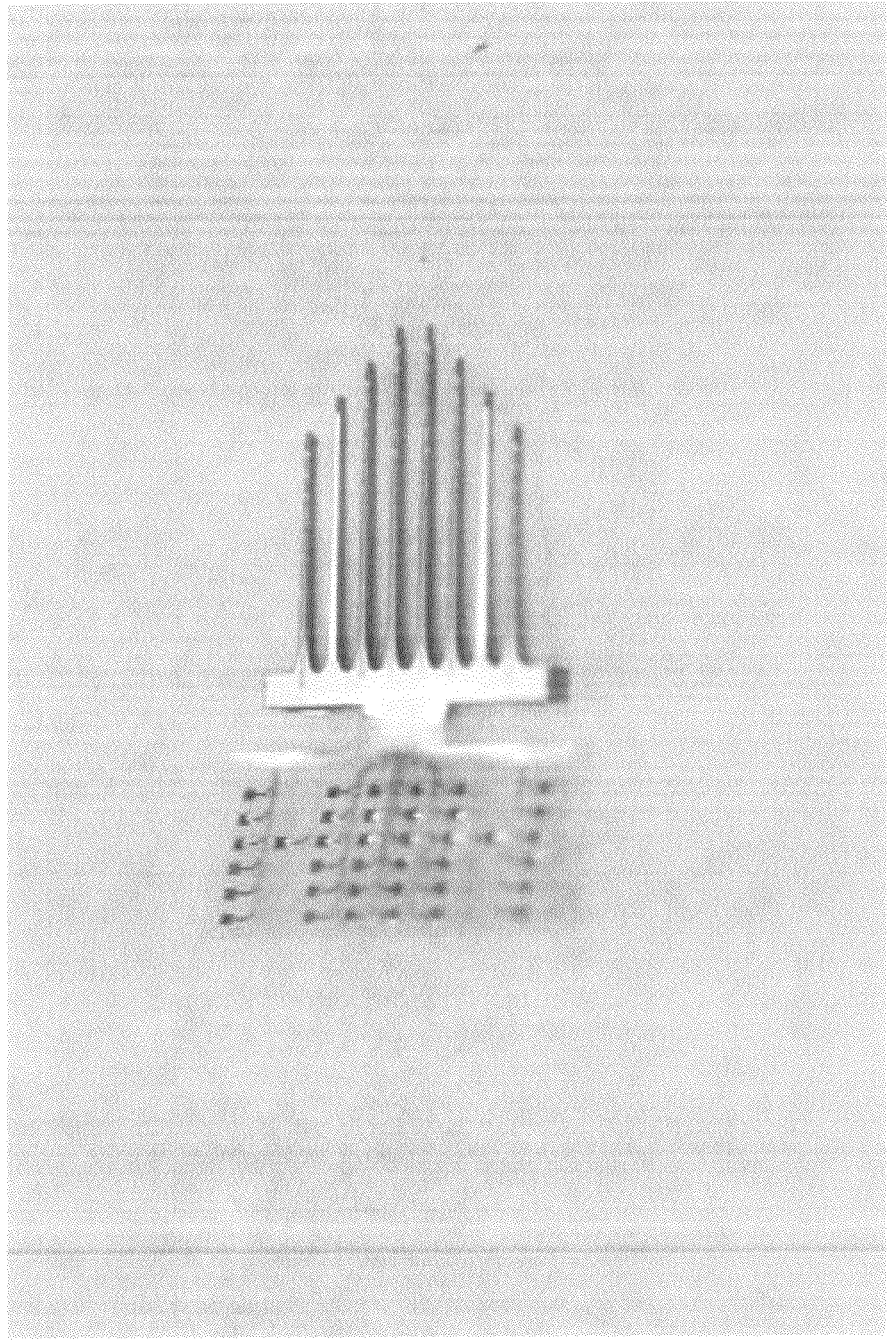
FIG. 30 illustrates a silicon probe structure for testing purpose. The parylene sheet extension provides metal pads for electrical connection of the probe to the parylene pocket structure of FIG. 28.
Figure 31:
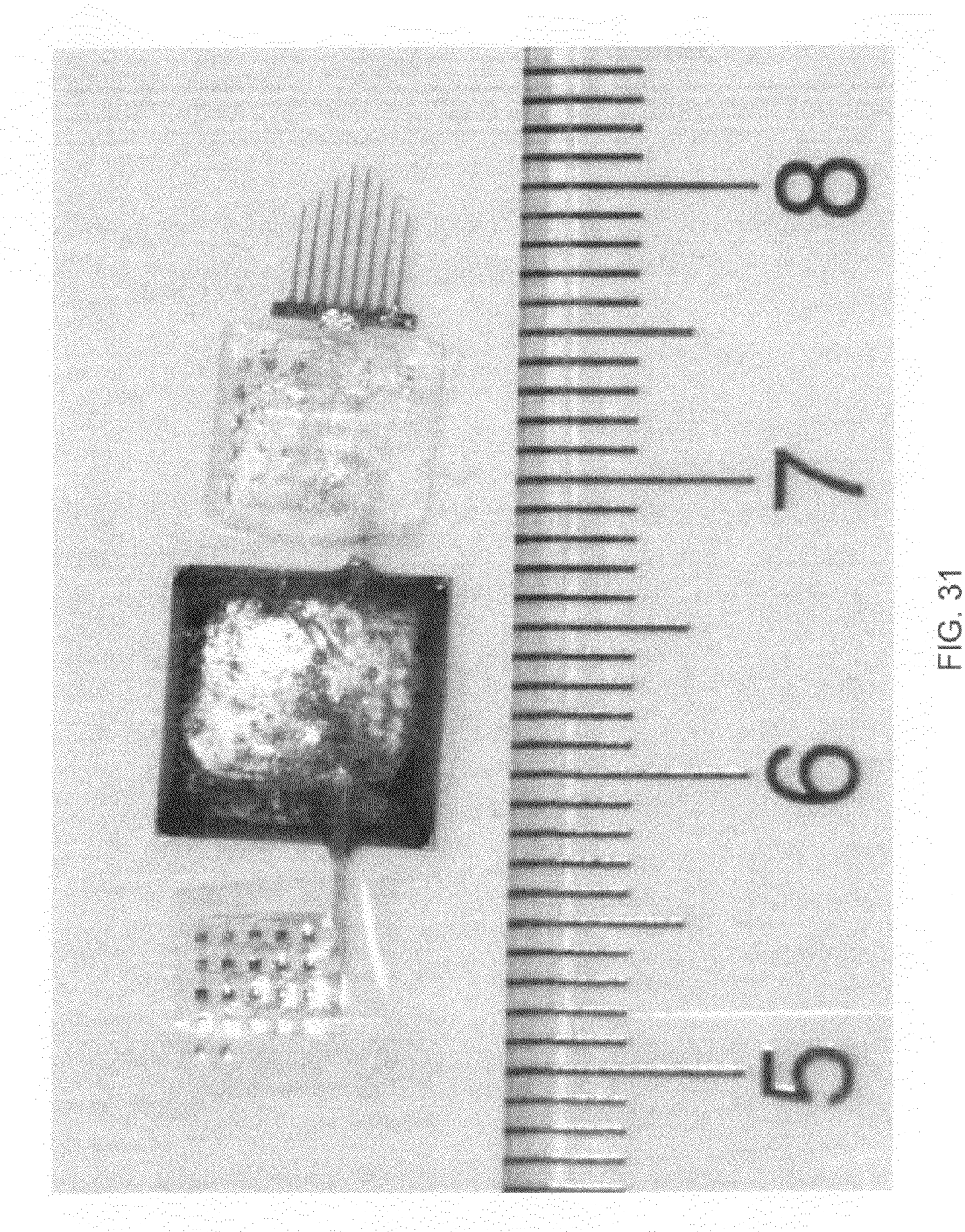
FIG. 31 illustrates a bonded and packaged structure comprising the probe of FIG. 30 connected to the structure of FIG. 28. In this device, the conduction chip was used. The impedance of the electrode was measured to be 600 kΩ.

In addition to the totally integrated silicon probe array, a second design was developed. It comprises a probe device with 36 electrodes and 2 reference electrodes separated from the parylene pocket structure, which is illustrated in FIG. 30. The probe device has identical geometry as that of the totally integrated device previously described. By separating the probe structure from the parylene pocket structure, a user would be able to test the pocket structure with the integrated IC chip before connecting it to the electrodes on the silicon probe, resulting in an advantage in terms of yielding and reliable testing. The assembled device is shown in FIG. 31. We use conductive epoxy as the medium for bonding the probe to the chip encapsulated in the parylene pocket.

We have described, reduced to practice, and tested a new parylene-pocket packaging technology to fabricate a silicon probe array with an IC chip close to its recording sites. The packaging schemes and the fabrication details are presented. A commercial amplifier chip was used and its full functionality after packaging was verified. High-temperature accelerated life-time saline soaking testing shows satisfactory performance in both the pocket structure and the overall system. It is expected that this new packaging technique will be useful for application in complex integrated biomedical implants needed for neural prosthesis research.

Chip Integration with a Flexible Parylene Pocket

We now describe a biocompatible packaging technique that utilizes a complete flexible parylene chip pocket with metal pads. This pocket can both house an IC chip or any discrete components and provide electrical connection to it. As a demonstration, a fully functional 16-channel amplifier CMOS chip has been bonded and tested with this structure. This work also integrates an 8-shank silicon probe array with the pocket, of which the electrode impedance was successfully measured.

An important goal in neural prosthesis is to be able to decode the movement intention in the parietal cortex from neurons by implanting neuroprobes. While 3-D integrated silicon probes have been successfully manufactured, the degradation of the signal to noise ratio (SNR) is still a major challenge because electronics are too far away from the recording site. Thus, a biocompatible packaging/integration solution to embed amplifiers near the recording sites would provide an advantage.

We describe a new packaging technique that utilizes a totally flexible parylene chip pocket with metal pads. This pocket can both house an IC chip inside and provide electrical connections to it, and can be integrated with silicon probes.

By application of the technology we now describe, one can make the chips and probes separately and later package them together, which is an advantage over direct IC/probe integration. The pocket size and the electrodes can be modified to suit different chips and applications as illustrated in FIG. 19 and is not sensitive to dry etching flatness. The whole bonding structure is conformally coated and sealed with parylene-C (poly-para-xylylene-C), and with medical grade epoxy to achieve total encapsulation for biocompatibility. As a successful demonstration, a 16-channel amplifier CMOS chip embedded with parylene pocket is described.

Figure 32:
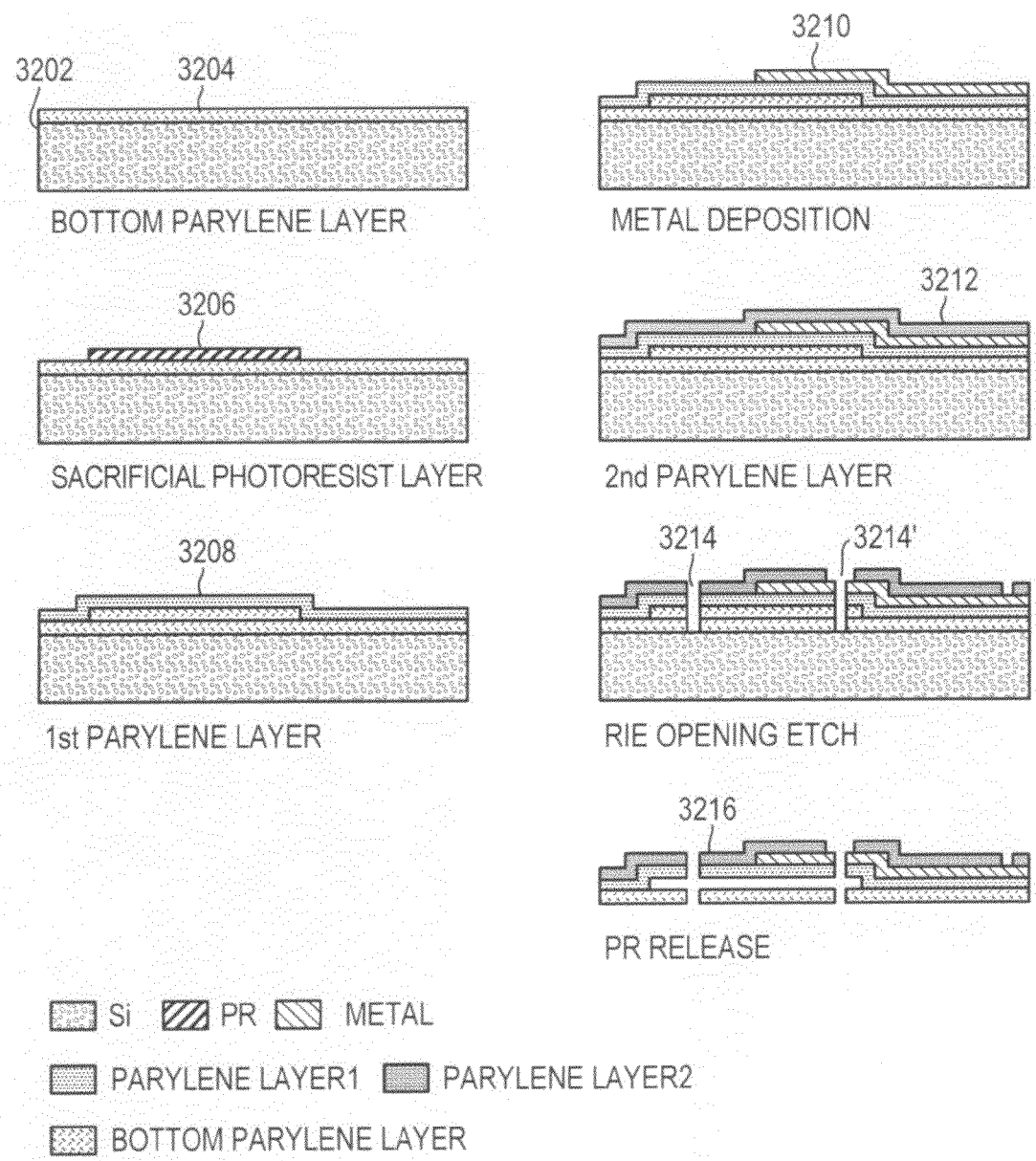
FIG. 32 is a diagram in cross-section illustrating the fabrication steps used in making a self-supporting parylene pocket structure.

The parylene pocket configuration is fabricated with RIE technology (Reactive Ion Etching) as illustrated in the process illustrated in FIG. 32. First, a bottom layer 3204 of 5 μm thick parylene-C is deposited on a silicon wafer 3202. A layer 3206 of sacrificial photoresist of 1 μm is then coated, which when removed will serve to define the parylene pocket structure. Another layer 3208 of parylene-C (5 μm) is deposited. A layer 3210 of Cr/Au (0.05/0.2 μm) is deposited using a lift-off process to provide electrical connection. The top layer 3212 of parylene-C (2 μm) is deposited to complete the structure. Electrode sites 3214, 3214' and the device definition are then created by a two-step RIE with $O_2$ Plasma process. The devices are released in photoresist stripper. An IC chip (see FIG. 27) is then inserted by hand into the parylene pocket, aligned (see FIG. 25), bonded with conductive epoxy (see FIG. 26) and totally coated with 10 μm of parylene.

Figure 33:
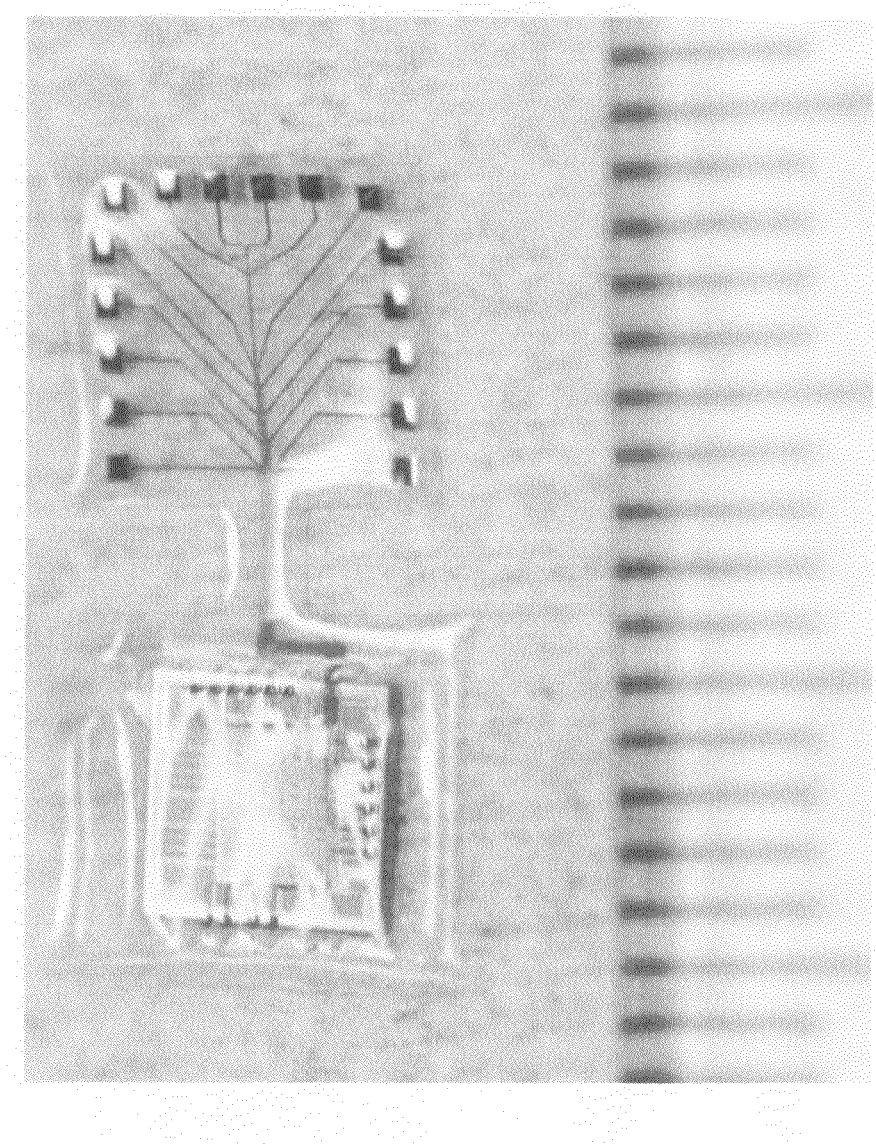
FIG. 33 illustrates an embodiment of a self-supporting parylene pocket structure, which in the embodiment shown is used to test the amplifier chip after bonding.

Device testing was done in several phases. First, the embedded CMOS amplifier chip was tested using a function generator on the pocket only structure, shown in FIG. 33. Sine and square waves of different frequencies were passed into the chip.

Figure 29:
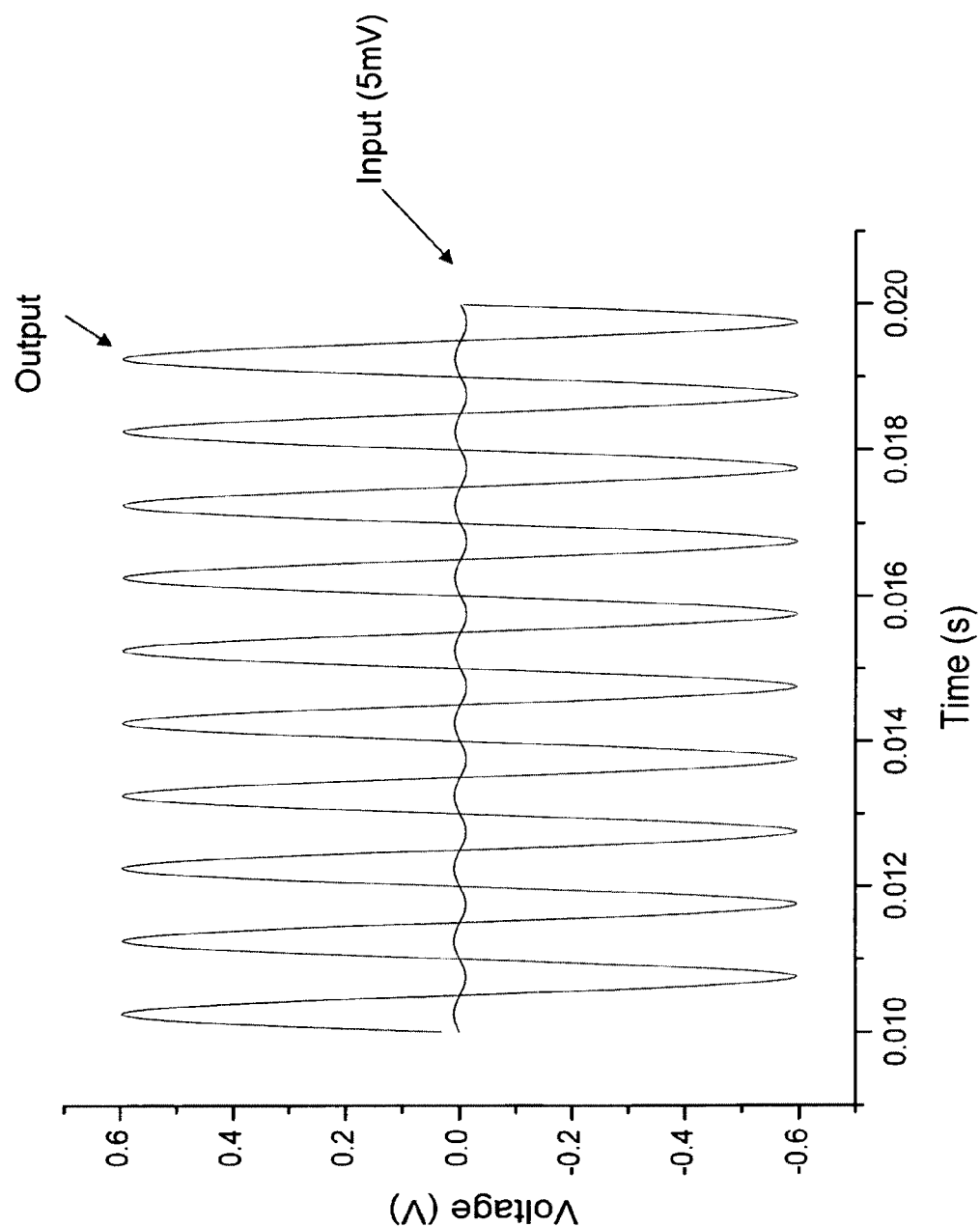
FIG. 29 is a graph illustrating an input comprising a 5 mV (10 mV peak to peak) sine wave of 1 kHz that is passed into the amplifier (gain=60) and its output signal as recorded using an oscilloscope. Signals of 0.5 kHz, 2 kHz, and 5 kHz were also tested with the chip.
Figure 34:
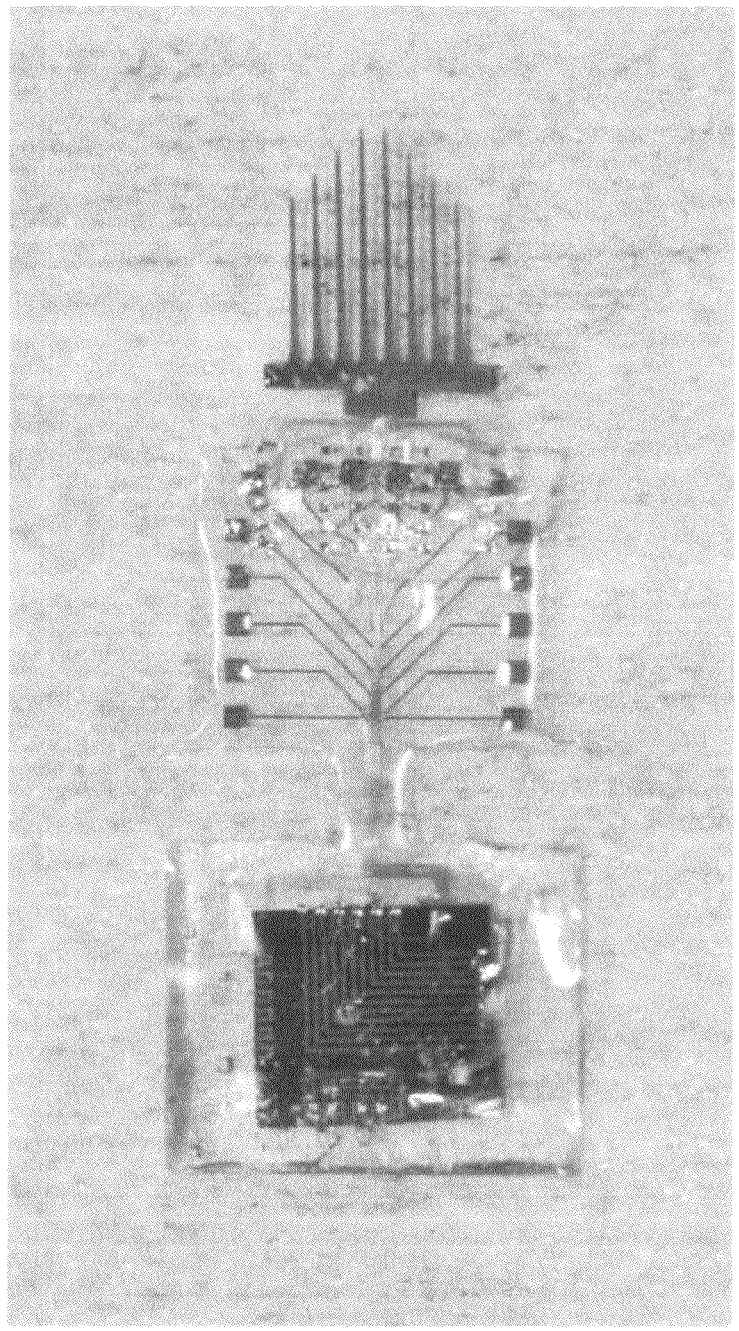
FIG. 34 illustrates a bonded and packaged structure. In this embodiment, the conduction chip was used. The impedance of the electrode was measured to be 600 kΩ.

The amplified output was measured and plotted, as illustrated in FIG. 29. A conduction chip was then bonded with a silicon probe (see FIG. 30) to form an integrated pocket structure, as illustrated in FIG. 34. The impedances of the probe electrodes were successfully measured, which indicates a successful functionality testing of our packaging technique. Finally, an on-going accelerated soaking life-time test was done on the packaged structure to determine the mean-time-to-failure. Testing shows the pocket structure with 1.5 mm of epoxy is able to function after soaking in 90° C. saline for more than 30 days, which should translate to years of lifetime in saline at 37° C.

We believe that the technology provides quick and simple packaging technology for all biological implants that require signal amplification in close proximity to the location where signals are obtained. We expect that the technology will facilitate a totally wireless biocompatible insertion system for neural prosthesis application, as we next describe.

Double Sided Pocket for Chips with Contacts on Both Surfaces

FIG. 35 is a diagram showing the steps performed in fabricating a self supporting parylene pocket structure that provides contacts to chips having contact pads on two opposite surfaces. This capability will allow the use of chips that are expected to have greater functionality as compared to chips having contacts on only one surface. As shown in FIG. 35A, a silicon wafer 3502 having a polished surface is provided as a support structure. As illustrated in FIG. 35B, a first layer of parylene 3504 is applied to the deposited on selected areas of the parylene layer 3504. As required, the first metal layer 3506 may comprise more than one metal structure, such as parallel lines configured to provide conductor traces and/or multiple connector pads. As illustrated in FIG. 35D, a second layer of parylene 3508 is deposited to cover and encapsulate the first metal layer 3506. The second layer of parylene 3508 can extend to a substantially similar extent as the first parylene layer 3504. As illustrated in FIG. 35E, an opening 3510 is created (for example by etching) in the second parylene layer 3508 to provide a path to make contact to a contact pad in the first metal layer 3506. As illustrated in FIG. 35F, a layer of photoresist 3512 is provided that covers the opening 3510 and that represents a sacrificial volume that when opened, provides a space into which a chip may be inserted. As illustrated in FIG. 35G, a third parylene layer 3514 is provided over the photoresist layer 3512. The third parylene layer 3514 can extend to a substantially similar extent as the first parylene layer 3504. As illustrated in FIG. 35H, a second layer of metal 3516 is deposited on selected areas of the third parylene layer 3514. As required, the second metal layer 3514 may comprise more than one metal structure, such as parallel lines configured to provide conductor traces and/or multiple connector pads. As illustrated in FIG. 35I, a fourth parylene layer 3518 is deposited to cover and encapsulate the second metal layer 3516. The fourth parylene layer 3518 can extend to a substantially similar extent as the first parylene layer 3504. As illustrated in FIG. 35J, one or more openings 3520 are provided to allow access to the contact pads in the second metal layer 3516. In one embodiment, the openings are created using reactive ion etching (RIE) methods. As illustrated in FIG. 35K, openings 3522, 3522' are etched through the structure to allow electrical access to all of the contact pads. As illustrated in FIG. 35L, the self supporting parylene pocket structure is released from the silicon wafer 3502 and the sacrificial layer of photoresist 3512 is removed, leaving a free-standing self supporting parylene pocket structure having metal contacts and leads that can be connected to contact pads on two opposite sides of a chip, such as an IC chip or a chip having desired electronic, computational, or other capabilities. The leads in the parylene pocket can be used to make electrical connection to circuitry, probes, or other electrical or electronic devices that allow communication with the encapsulated chip.

Integrated Wireless Neurostimulator

We now describe the design, fabrication and functional testing of a fully implantable, flexible, parylene-enabled neurostimulator that features single channel wireless stimulation capability. The system comprises a CMOS stimulator chip, a fold-and-bond RF coil, two platinum electrodes, and discrete capacitors. The MEMS components are fabricated with a parylene-metal skin technology, and the system assembly is achieved by interconnecting individual components together on a parylene substrate with silver epoxy. The functionality of the integrated system has been verified using a telemetry link setup, and single-phase pulses with amplitudes ranging from 7 to 8.5 V have been detected.

We describe flexible wireless neural implants, employing parylene-based MEMS devices integrated with other discrete components, such as application specific integrated circuits (ASICs) and chip capacitors. A parylene-metal skin technology allows us to microfabricate RF coils and multielectrode arrays in a process compatible way. We describe the integration of such a coil and an electrode array with a single channel stimulator chip to build a fully functional system for neural stimulation. For the first embodiment, MEMS devices are fabricated separately, and assembled with other system components using biocompatible silver epoxy. Parylene-C serves as a substrate and packaging material, and therefore the final system is highly flexible and biocompatible for medical implantation.

System Design

Figures 36A, 36B:
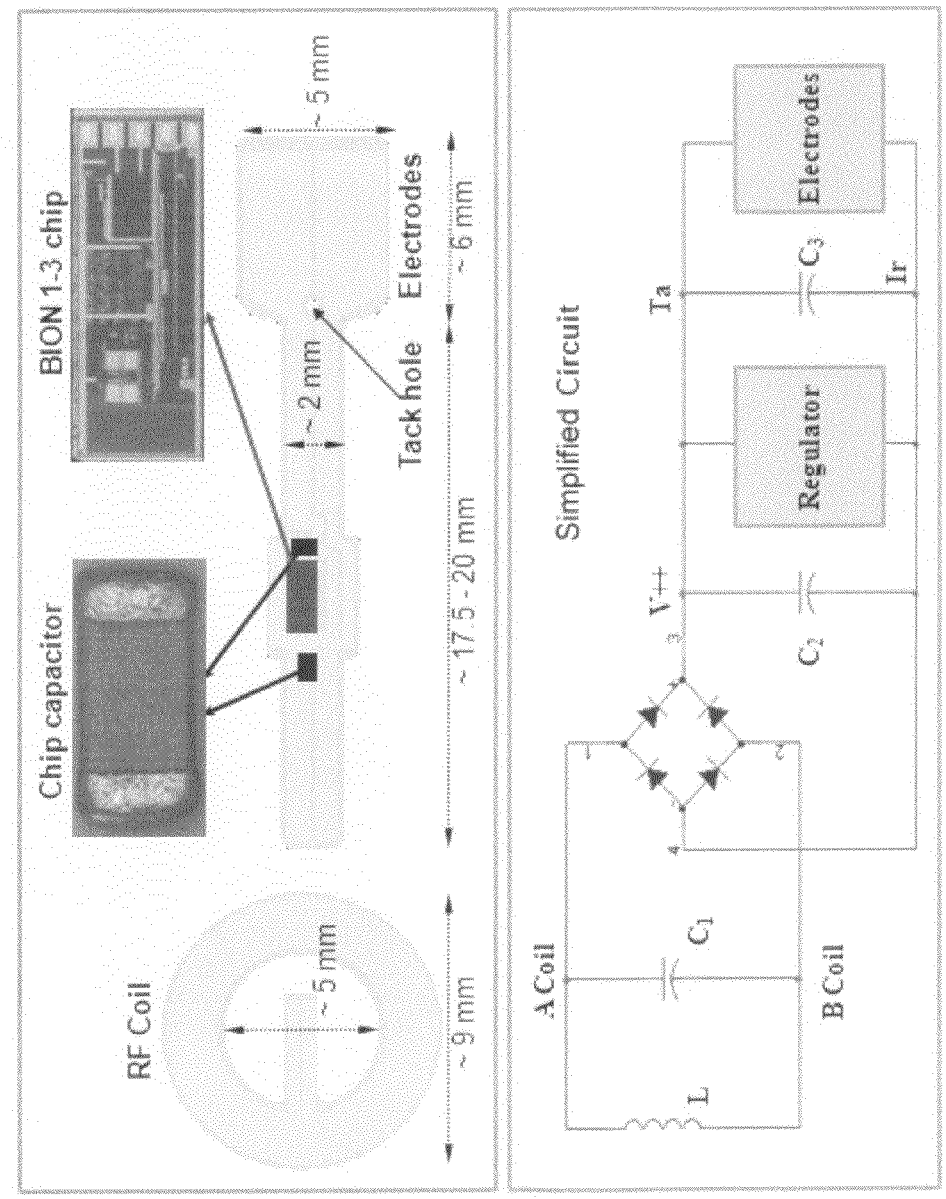
FIG. 36 illustrates a circuit layout of the single channel stimulator, showing the connections between individual components, and the corresponding system schematic.

FIG. 36A depicts the system schematic of a single channel stimulator, which comprises a BION1-3 CMOS chip, two capacitors, a specially designed RF MEMS coil for wireless power and data transmission from an external personal trainer, as well as a carrier substrate. The flexible carrier has interconnection leads and contact pads for system assembly, and two electrodes of which one serves as the stimulating electrode while the other is the floating ground. The overall physical dimensions of the MEMS coil and the carrier substrate are to meet specifications used in retinal implantation, which are determined based on surgical implantation results in canine eyes.

The BION chip is a single-channel stimulator which is initially developed to mimic muscle spindle function, and to treat patients suffering from muscle paralysis. Once implanted into paralyzed muscles, the chip can receive both power and command signals through inductive coupling over a 480 kHz~500 kHz power carrier generated in an external unit, allowing the chip to emit precisely timed stimulation pulses with highly regulated amplitude and pulse-width. The BION chip has physical dimensions of ~1 mm in width, ~2.33 mm in length, and ~257 μm in thickness. There are five pads on the chip with sizes of approximately 120 μm×74 μm. The distance between two adjacent pads is about 110 μm.

Two ceramic chip capacitors (AVX Corporation, Myrtle Beach, S.C., USA) are incorporated in the integration system to tune the circuit. As seen from the circuit layout FIG. 36B, $C_1$ is a frequency tuning capacitor in parallel with the receiving coil to achieve a resonant frequency of ~500 kHz. $C_2$ is a charge storage capacitor which has a capacitance of ~22 nF, provided by Dr. Gerald Loeb's group at the University of Southern California. These capacitors are about 1 mm×0.5 mm×0.56 mm in size.

Fabrication Process

The fabrication is divided into three steps: carrier substrate fabrication, RF MEMS coil fabrication, and final system assembly and packaging. To build the flexible substrate, a 200 nm layer of platinum is e-beam evaporated on a parylene-C coated silicon substrate. Then the metal is patterned using lift-off to form connection pads, interconnection leads, and electrode sites. Platinum is selected as the electrode material for optimal simulation capability. No adhesion metal layer is need in this case because platinum and parylene are known to have good mutual adhesion. After metal patterning, another layer of parylene-C is deposited to seal the entire structure, followed by oxygen plasma etching in a reactive ion etching (RIE) system with a photoresist mask to define the outer geometry of the substrate, as well as to open the electrode sites and the contact vias. Finally, the device is peeled off from the silicon substrate in a water bath. FIG. 37 illustrates the detailed process for making the carrier substrate, where steps 37B through 37D describe the lift-off technology for platinum patterning.

In FIG. 37A, a polished silicon wafer 3702 has a layer of parylene 3704 deposited thereon. In FIG. 37B, layers of a LOR3B resist 3706 and a regular photoresist 3708 are deposited and patterned. In FIG. 37C a metal 3710 is deposited over the patterned resists. In FIG. 37D, the resists are removed, leaving metal 3710 in predefined locations on the parylene layer 3704. In FIG. 37E additional parylene is deposited. In FIG. 37F the separated substrate is illustrated.

Figures 38A, 38B:
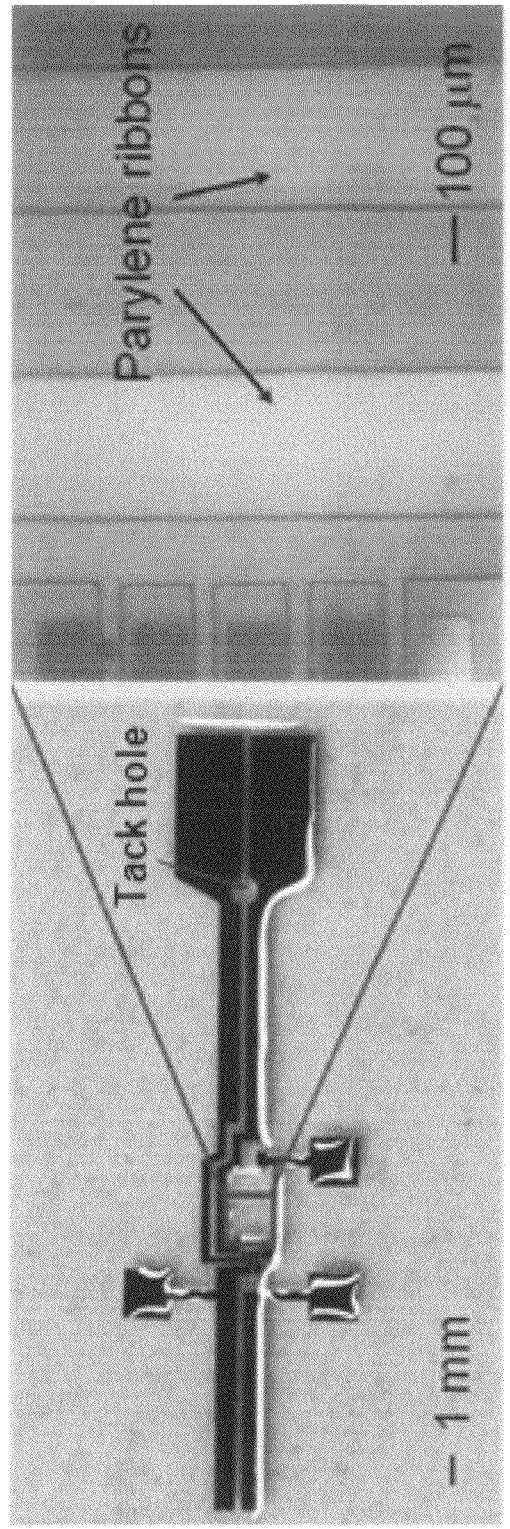
FIG. 38A illustrates a fabricated carrier substrate with electrodes, interconnection leads and contacts.
FIG. 38B is an enlarged image of a region of FIG. 38A that shows the parylene ribbons used to hold the BION chip.

FIG. 38 presents a fabricated carrier substrate. The microscope image shows a special chip site design where parylene ribbons are etched in a way such that the chip can be held in place and self-aligned to the contact vias on the substrate during system assembly. The array site contains a 450 μm diameter tack hole so that the array can be attached to the retina using a retinal tack.

To fabricate the MEMS coil, a fold-and-bond technology is involved, in which two coils are placed in series, and made of a single 3 μm layer of gold to achieve low resistance and high Q factor. Then the device is folded into two layers and stacked together with the assistance of two glass slides. Aluminum sheets are inserted between the parylene surface and the class slides to prevent parylene sticking on the glass. After that, the stacked coil is placed in a vacuum oven with a chamber pressure of ~10 Torr for bonding. The oven temperature ramps from room temperature to 250° C. The device is then soaked at the bonding temperature for 2 days, followed by a slow cool-down to room temperature. Nitrogen backfill is introduced during the thermal bonding process to equalize the chamber temperature.

A fabricated coil is shown in FIG. 39, comprising two layers of metal with 10 turns in each layer. In-and-out leads are connected to the carrier substrate from the center, facilitating the surgical procedure. Through vias are designed to overlap with the contact pads, so that the interconnections to the carrier substrate can be formed from either side. The electrical properties of this coil are measured, showing an inductance of approximately 2.24 µH and a DC resistance of approximately 15.82Ω, which results in a Q factor of 0.45 at 500 kHz.

For hybrid system assembly, individual components (the BION chip, the coil and the capacitors) are aligned to the corresponding interconnection vias on the carrier substrate. A small amount of biocompatible silver epoxy EPO-TEK H20E (Epoxy Technology, Billerica, Mass., USA) is then applied on the contacts and cured at 80° C. for 3 hours in a convection oven. The conductive epoxy serves two purposes: to form the interconnections between the components as well as to bond the components onto the substrate. Finally, parylene-C is coated on the entire system just leaving the electrode sites open in order to protect the circuitry from the corrosive eye fluids and to improve the durability of the epoxy contacts. FIG. 40 illustrates an assembled single channel stimulator system. FIG. 41 shows close-up views on the interconnections for each component.

Because the BION chip has only 5 pads, hand assembly using epoxy interconnection is quick and easy. However, a main problem encountered during the fabrication is the lack of control of the epoxy amount when applied by hand. Short circuits can be created if too much epoxy is applied. Epoxy reflow can also happen during high temperature curing, resulting in short circuits. For chips with high density pad layouts, this hand assembly is no longer applicable, and thus a wafer level integration technology is necessary.

Operation Results

Figure 42:
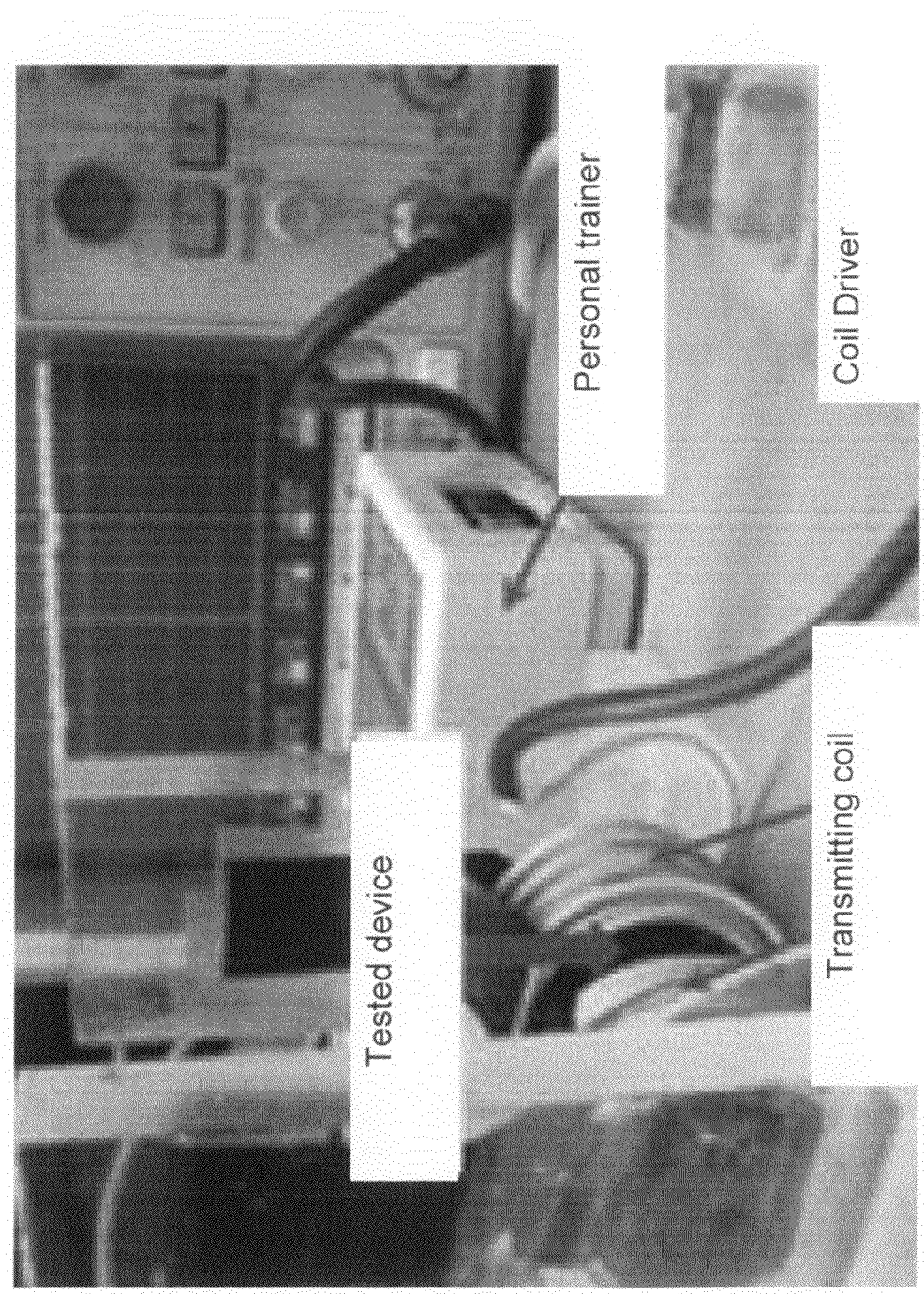
FIG. 42 illustrates a telemetry setup for functionality test of the assembled BION system.
Figure 43:
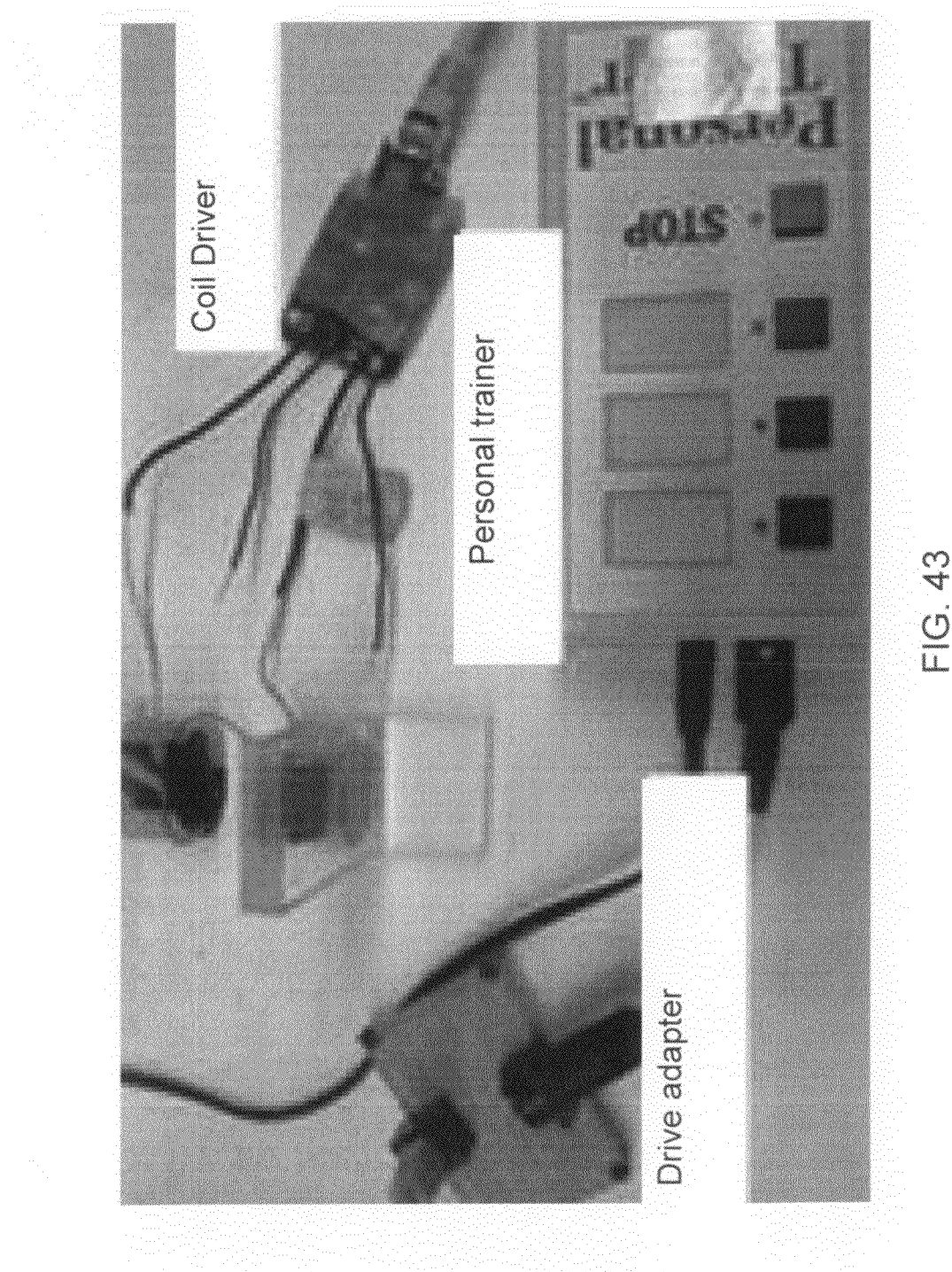
FIG. 43 illustrates a personal trainer and other peripheral accessories of the primary stage.

After the assemble system is made, its functionality is verified using a telemetry link setup, shown in FIG. 42. The primary stage is shown in FIG. 43, which comprises a personal trainer unit, a class-E coil driver and a hand-wound transmitting coil, can generate a power carrier of approximately 500 kHz. The personal trainer stores command programs personalized for individual subjects, records the time and duration of treatment, and transfers this information to an external computer for real time monitoring. Up to three programs can be preloaded into the memory of the personal trainer. The coil driver is connected to the personal trainer through a custom made adapter. The transmitting coil has an inductance of ~46.4 µH and a Q factor of ~118 at 500 kHz. Litz wires 1025-44 SPN are used for winding the primary coil to reduce the skin effect and proximity effect losses. The transmitting coil is built in a solenoid shape to establish a more uniform electromagnetic field inside the coil. Additionally, ferrite cores are inserted in the transmitting coil to magnify the electromagnetic field and therefore to improve voltage transfer efficiency.

Figure 44:
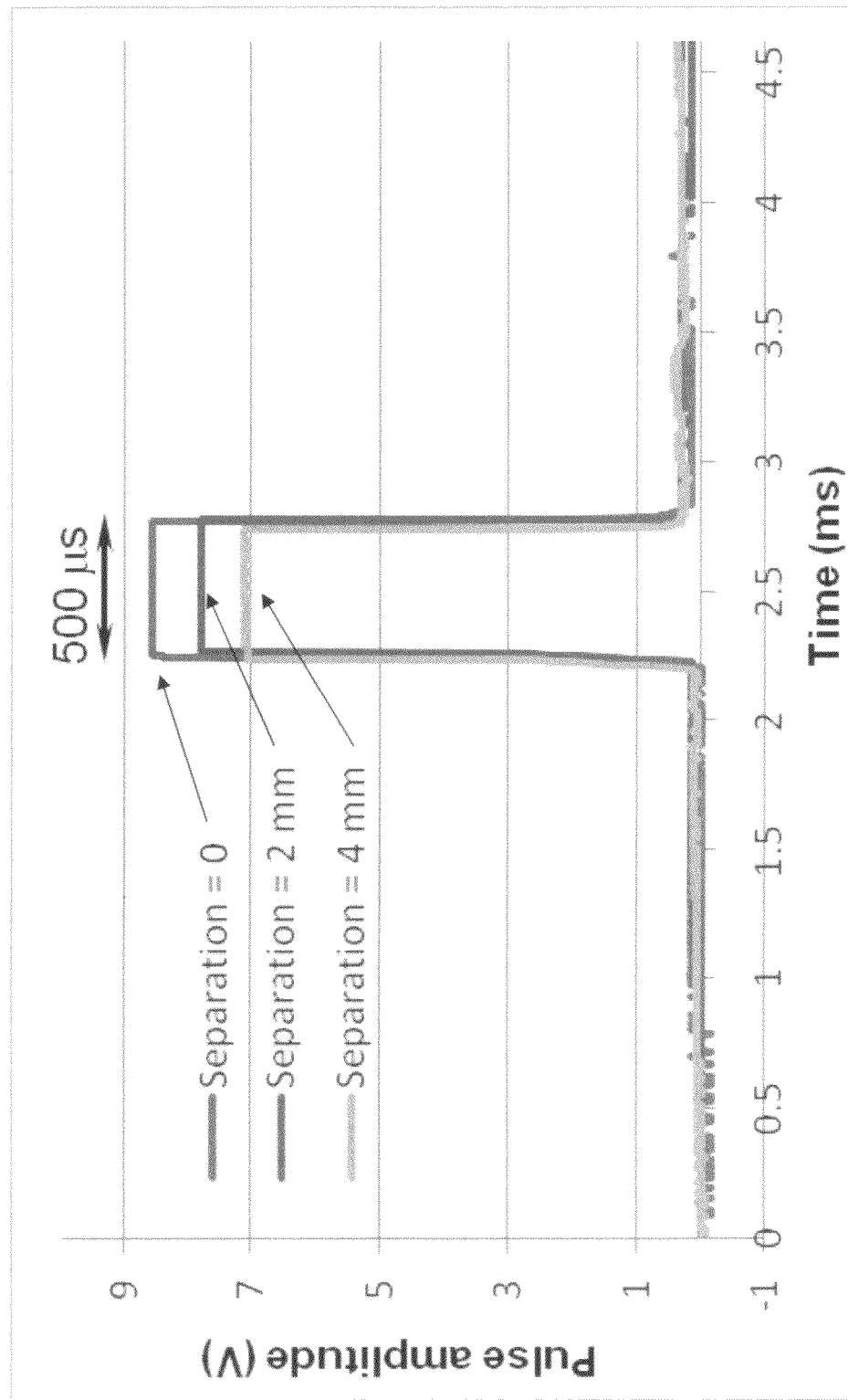
FIG. 44 illustrates three recorded stimulation pulses at different coil separation distances.

In vitro measurements have been conducted using this setup, and output signals of the integrated stimulator are monitored by connecting two electrodes directly to an HP 54645A oscilloscope (HP/Agilent Technologies Inc., Santa Clara, Calif., USA). The distance between the two coils is varied during testing, and a maximum detectable range of ~4 mm is found. The recorded stimulating pulses at the different separation distances are given in FIG. 44, showing a pulse width of approximately 500 µs, and amplitudes varying from 7 to 8.5 V.

Figure 45:
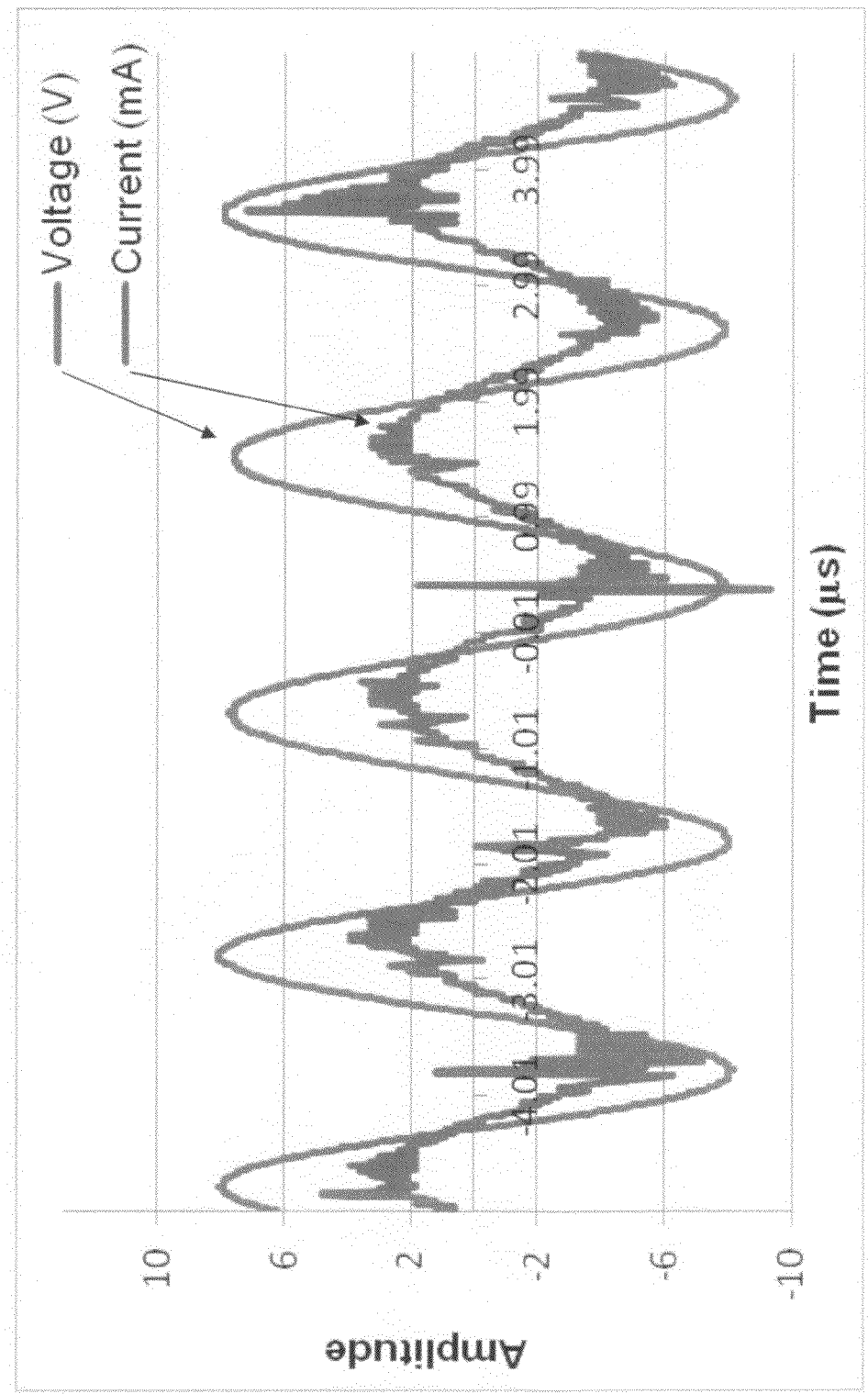
FIG. 45 illustrates typical waveforms of transferred voltage and current to the chip.
Figure 46:
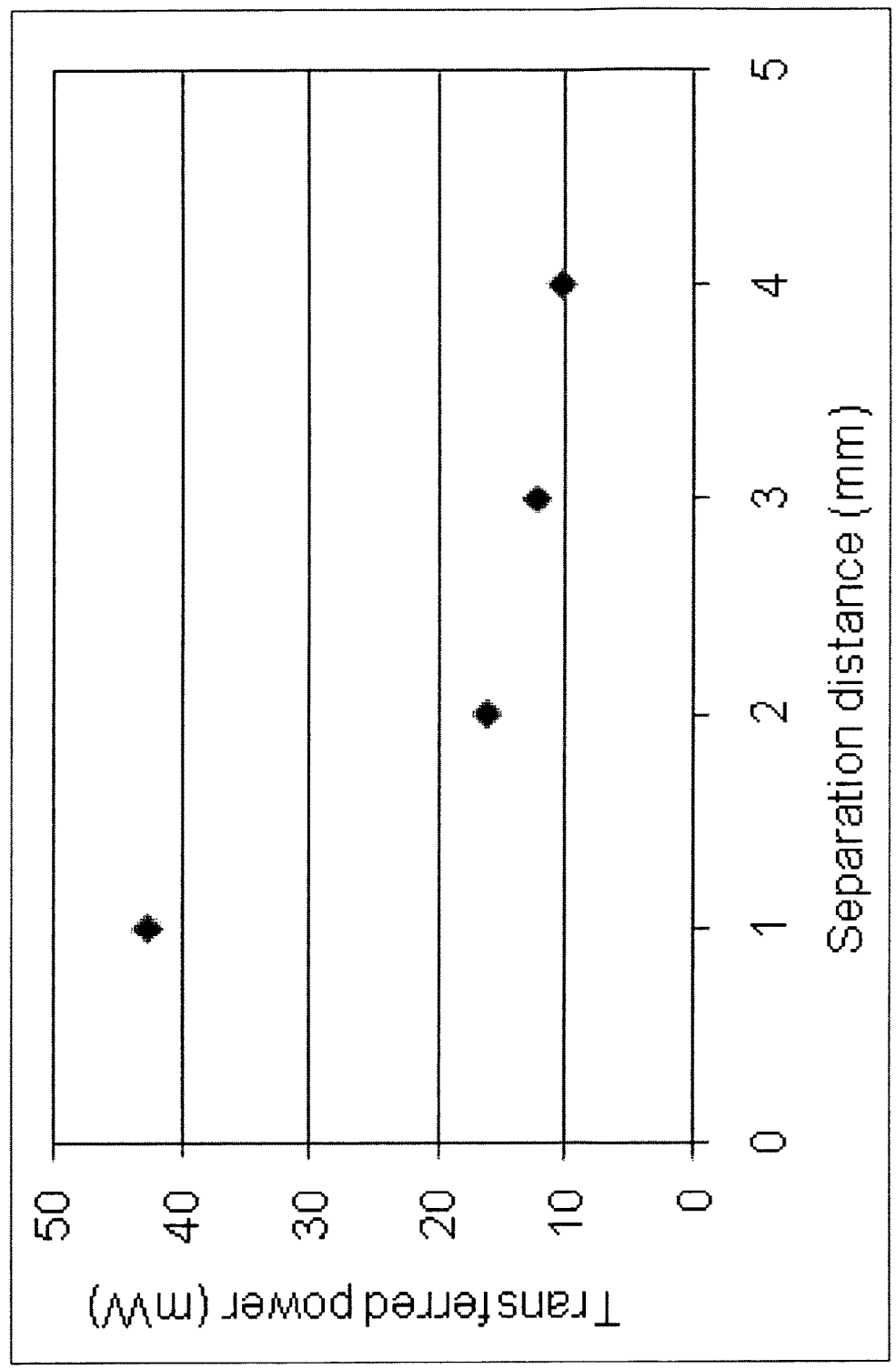
FIG. 46 illustrates transferred power at different separation distances between two coils.

In order to estimate the power transfer capability of the MEMS coil, the voltage across the receiving coil terminals and the current delivered to the chip are measured. FIG. 45 shows typical waveforms of the transferred voltage and current, indicating a resonant frequency of ~505 kHz and a ~25 degree phase drift between voltage and current. As mentioned earlier, the tuning capacitor is a commercially available chip capacitor, which has limited options of capacitance values. Therefore, it is difficult to fine tune the resonant circuit to achieve precise synchronization. The delivered power at the different separation distances are also investigated, as shown in FIG. 46. The MEMS coil can transfer a maximum power of ~43 mW through this inductive link at the separation distance of 1 mm. As the separation distance increases to 2 mm, the power drops by 62%, which is mainly limited by the low Q factor of the receiving coil.

The functionality of the integrated system has been successfully demonstrated in air. However, the short detectable distance would restrict the practicality of this system in actual applications. Further improvement can be achieved by optimizing coil design, such as increasing metal thickness and/or the number of metal layers, in order to enhance the coil Q factor and the power transfer efficiency. The verification of system functionality through implantation in rabbit eyes is underway.

A single channel neural stimulator has been designed, and one embodiment has been successfully fabricated and tested. Test results demonstrate that the BION chip can be driven by the MEMS coil within a 4 mm separation distance. Output pulses with a pulse width of ~500 µs as and amplitudes of more than 7 V are measured from the simulating electrode, indicating that system can be operated in vitro.

High Density 128-Channel Chip Integration with Parylene Pocket

Current state-of-the-art technologies for retinal and cortical prosthetics suffer greatly from complicated IC packaging with high lead count, for example, more than 60 leads. There is also a lack of high density capability. We describe a novel biocompatible packaging technique that utilizes a flexible parylene pocket with metal pads on silicon substrate in order to overcome these challenges and to accommodate the increasing number of prosthetic chips. This pocket can be designed to house any IC chip or discrete component and provide electrical connection to it. As a demonstration, a high density, 128-channel conduction chip along with surface mount capacitors, resistors and inductors have been bonded and tested with this structure. It is believed that this new technique can be further scaled to achieve 10,000 connections in an area of 1 cm$^2$.

Figure 47:
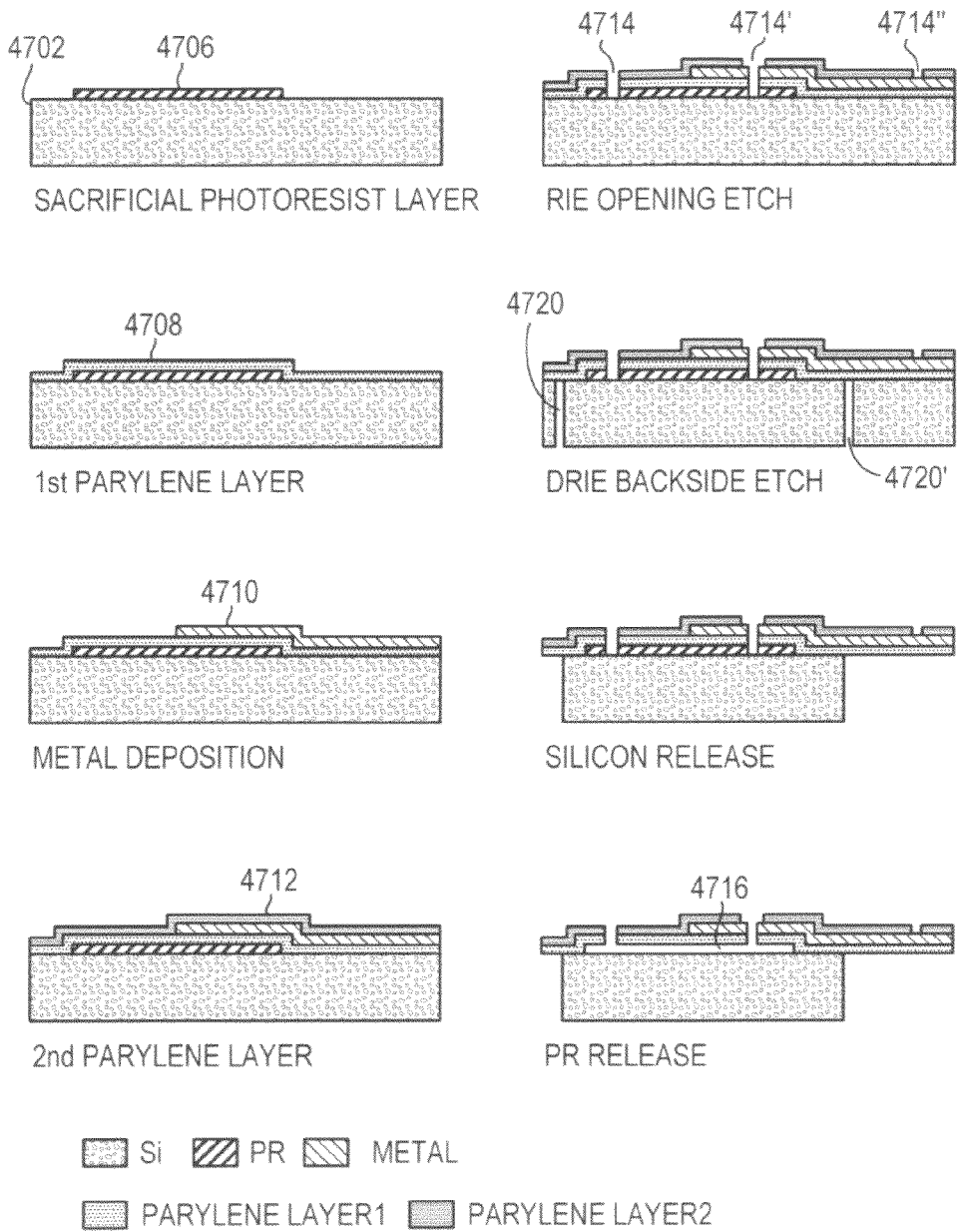
FIG. 47 illustrates in cross-section the fabrication process of a parylene pocket with parylene bonding pads. We use melted parylene as the adhesion layer between the parylene sheet and the silicon support

As illustrated in FIG. 47, the parylene pocket structure is fabricated with a combination of RIE (Reactive Ion Etching) and DRIE (Deep Reactive Ion Etching) processes.

Figure 48:
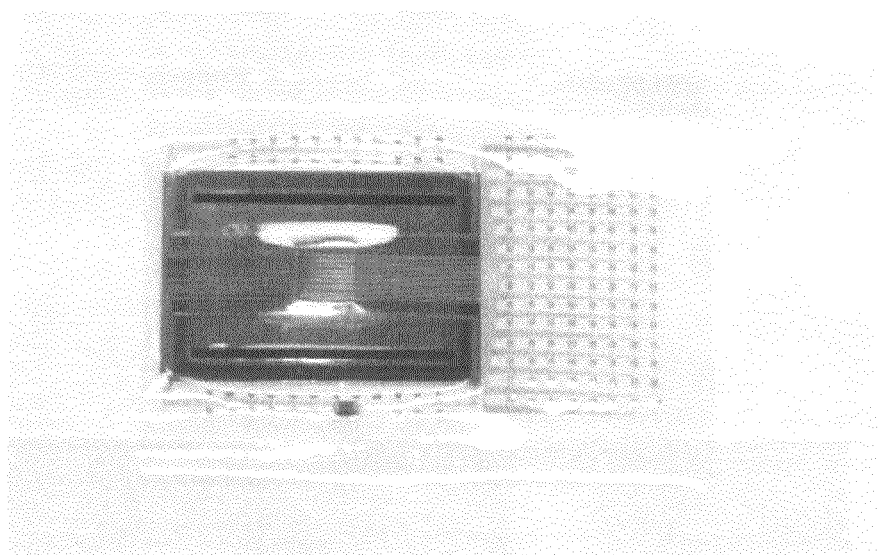
FIG. 48 illustrates a fabricated parylene pocket with metal bonding pads for the high density 128 channel IC chip integration. In the figure, the chip is already inserted into the pocket.
Figure 49:
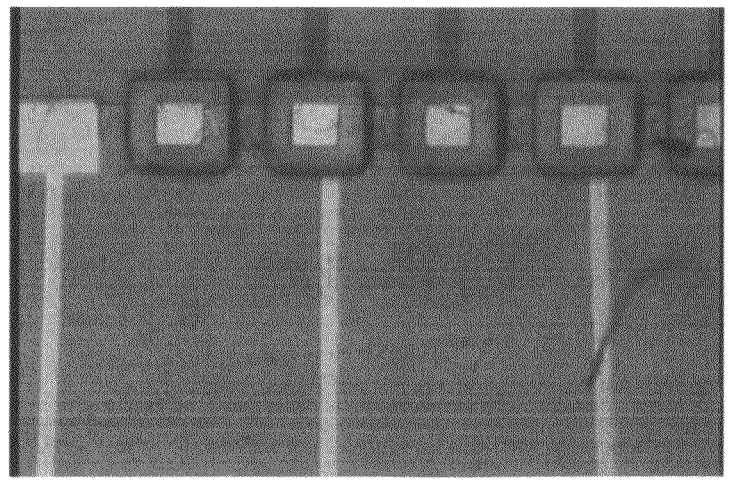
FIG. 49 illustrates the alignment of the bonding pads of the 128 channel chip and the bonding pads on the parylene pocket.
Figure 50:
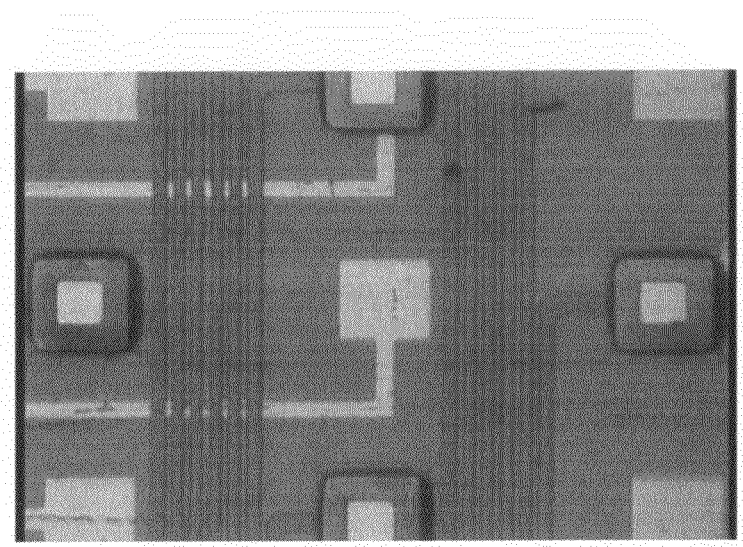
FIG. 50 is another figure that illustrates the alignment of the bonding pads of the 128 channel chip and the bonding pads on the parylene pocket.
Figure 51:
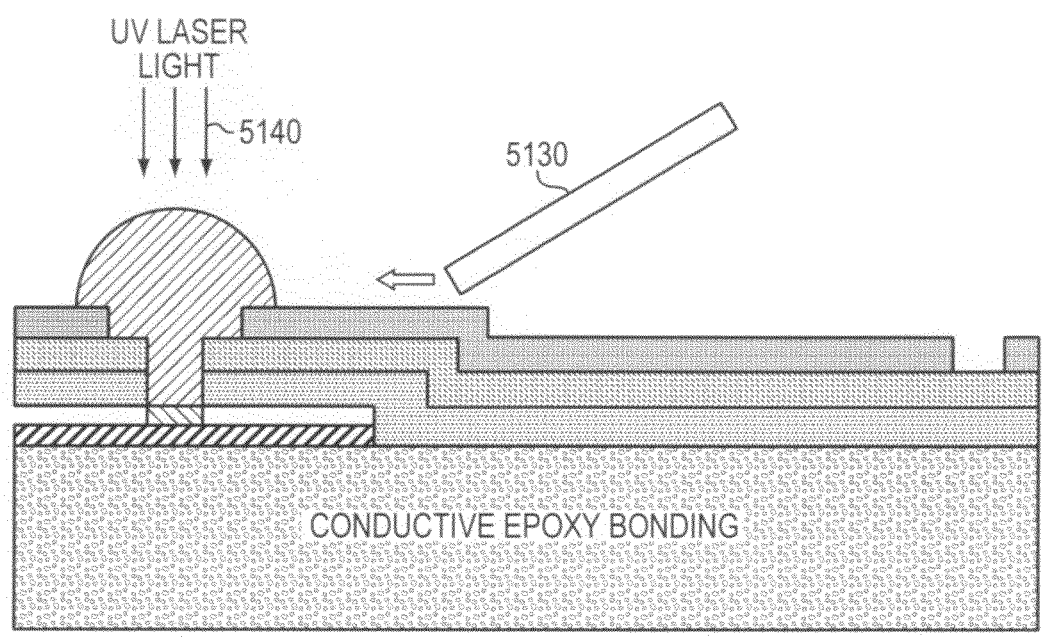
FIG. 51 illustrates steps in laser curing of the epoxy. The squeegee is used to push the excess conductive epoxy away from the surface. A UV laser is then used to cure the epoxy that remains in the trench to make the connection between the pads of the parylene and the IC chip.

On a polished surface 4702 of a silicon wafer, a sacrificial photoresist layer 4706 is spin-coated for pocket releasing. A layer 4708 of parylene-C (6 µm) is then deposited, followed by a layer 4710 of Cr/Au (0.05/0.2 µm) lift-off process with electron beam evaporation to provide electrical connection. The top layer 4712 of parylene-C (6 µm) is deposited to complete the parylene-metal-parylene sandwich structure. Electrode sites 4714, 4714' and the device definition are then opened by a two-step RIE with O$_2$ Plasma (Reactive Ion Etching) process. A DRIE backside etch is used to define the back surface dimensions as defined by etched trenches 4720 and 4720'. After the excess silicon is released, the parylene pocket structure 4716 is opened in photoresist stripper and the structure is dried. An IC chip is then inserted into the parylene pocket as illustrated in FIG. 48. It is aligned with the traces in the pocket as shown in FIG. 49 and FIG. 50. The chip is bonded with conductive epoxy as illustrated in FIG. 51. As appropriate, the structure can be totally coated with parylene-C again for complete encapsulation and to ensure biocompatibility.

Figure 52:
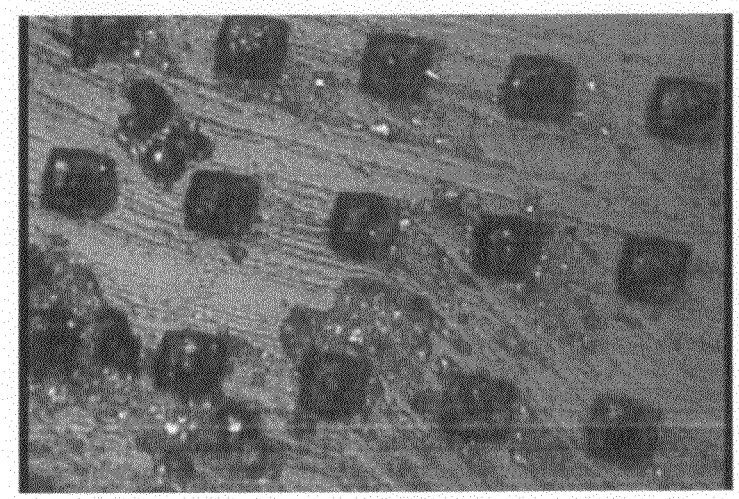
FIG. 52 illustrates the surface of the bonding pads after the squeegee has moved away excess epoxy. There is a significant amount of residue left.
Figure 53:
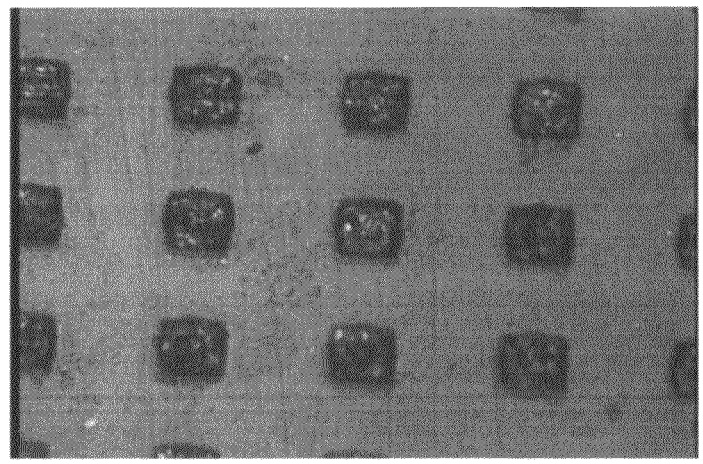
FIG. 53 illustrates the surface of the bonding pads after the UV laser treatment and an acetone rinse. The surface is much cleaner, and no short circuits are found.
Figure 54:
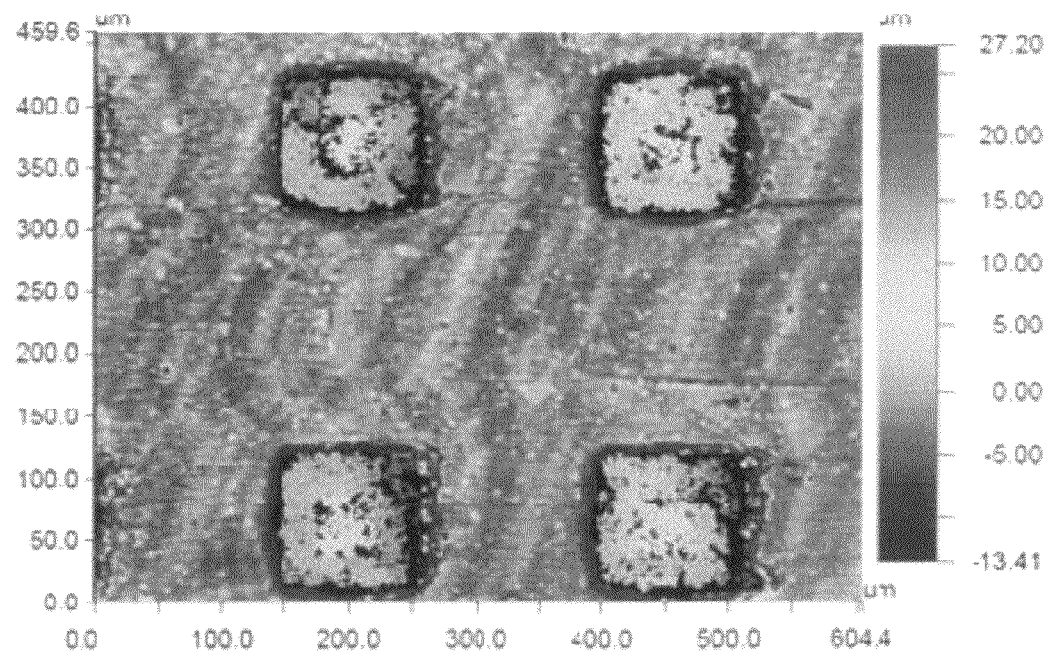
FIG. 54 is a diagram that illustrates the surface profile of the bonded surface. The maximum height of the conductive epoxy bump is about 25 µm.
Figure 55:
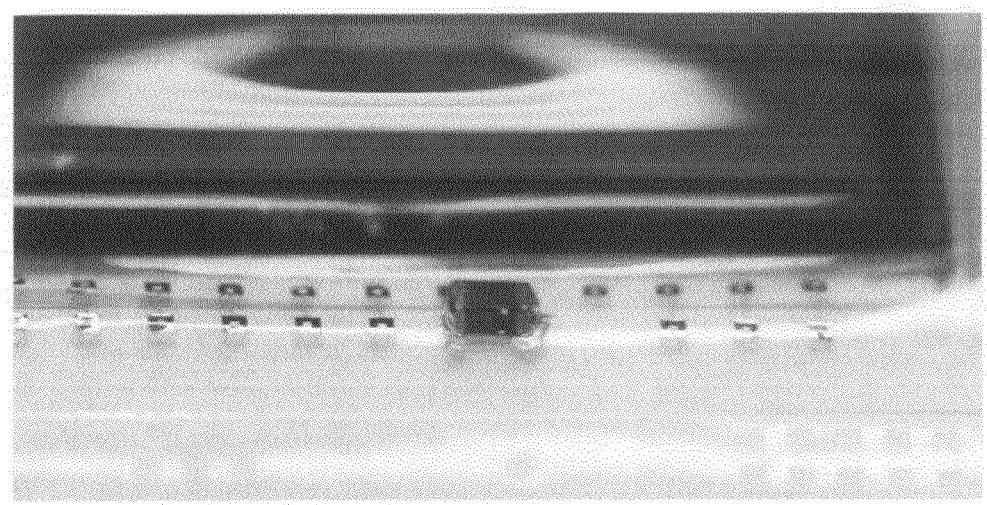
FIG. 55 illustrates a surface mounted resistor bonded on two of the metal pads on the parylene sheet. All discrete components, including MEMS Inductive Coils, can potentially be integrated with this structure.

After the fabrication process, the devices are released from the wafer. An IC chip is then inserted into the parylene pocket, in some embodiments by hand, aligned as shown in FIG. 49 and FIG. 50, and bonded with a conductive epoxy squeegee process, as shown in FIG. 51. It is then totally coated with parylene for overall biocompatibility. In the epoxy squeegee process, a commercially available conductive epoxy is mixed and applied globally on the surface of the chip. A rubber squeegee is then used to push excess epoxy off the target surface of the chip pad bonding area. Pulsed laser annealing with an ultra-violet laser is then utilized to cure the epoxy connections locally, which enhances the physical strength and stiffness of the bond. Finally, acetone is used to wash away the uncured conductive epoxy, which leaves the surface of the bonding pad relatively clean and the space between pads free of unwanted short circuit conductions, as shown in FIG. 52 and FIG. 53. The profile of the bonding epoxy bumps has been examined. The result illustrated in FIG. 54 shows that the maximum height is ~25 µm. As illustrated in FIG. 55, discrete components such as diodes and capacitors can be connected to this parylene-pocket structure.

Figure 56:
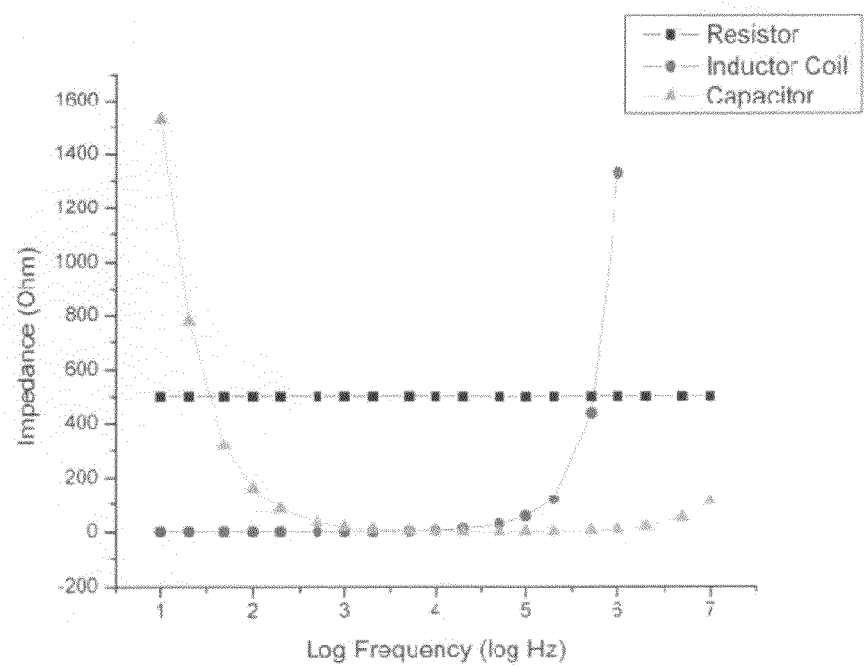
FIG. 56 is a diagram showing a frequency vs. impedance plot of the discrete components that were bonded and tested with the parylene structure. Surface mount resistors and regular inductors and capacitors are used for the integration, which shows its potential to be used in a fully integrated system.

Device testing is performed in two stages. The first stage is chip integration testing and the second stage accelerated life testing. A dummy chip with dimensions of 5 mm×5 mm×500 µm is inserted into the pocket and bonded with the laser annealing technique to test the functionality of the structure. The pads on the dummy chip have minimum distances of 140 µm and maximum distances of 500 µm. Commercial discrete components such as capacitors, resistors and inductors (coils) are connected to the pads on the parylene layer and are tested with a function generator. Sine waves of different frequency were passed into the chip and the components. FIG. 56 illustrates the successful functionality testing of the packaging technology. Finally, accelerated life-time soaking test is conducted to determine the mean-time-to-failure of the devices. Testing shows the pocket structure with 1.5 mm of biocompatible silicone is able to function after soaking in 90° C. saline for more than 30 days, which should translate to years of lifetime in saline at 37° C.

It is expected that one will be able to integrate data and power coils on this platform to provide a total integrated system that will be implanted in vivo. It is expected that the rapid, inexpensive and efficient method of bonding a high density chip as described herein will provide a totally wireless biocompatible system for various applications, one of which is expected to be a retinal prosthesis application.

Many different pocket architectures are possible, and different forms of pockets may be most suitable for different applications. Examples include a pocket on a silicon substrate; an all-parylene pocket; pockets designed to encapsulate specific commercially available chips; pockets designed to encapsulate discrete components; pockets designed to encapsulate PCBs; a single layer pocket; a double layer pocket; a multi layer pocket; pocket stacking to achieve a 3D structure; a pocket with parylene cable connected thereto; a pocket with a MEMS coil; a pocket with MEMS capacitors and pockets comprising materials other than parylene. Interconnection has been demonstrated using several procedures, including the squeegee method; the hand paint method; methods involving use of conductive epoxy; and a laser annealing method, in which laser-assisted annealing and curing of the conductive epoxy/polymer has been successfully demonstrated.

Many different materials can be used in fabricating pockets as described herein. While parylene has been described as a material that is well suited to pocket architectures that are intended for implantation in living organisms, it is believed that many thin-film polymers, such as PMMA, teflon, silicone and polyimide, can be used to make pockets for the same or similar applications. In fact, any thin-film polymer that can have metals provided as internal metal surfaces can be used to make pockets for applications involving packaged chips and/or electronic and electrical circuit components.

Definitions

Recording the results from a data collection operation, e.g., obtaining and recording a signal representing data or information, or obtaining and recording an image, such as for example, recording results in one or more dimensions, using one or more colors or hues, or at a particular frequency or wavelength, is understood to mean and is defined herein as writing output data to a storage element, to a machine-readable storage medium, or to a storage device. The recorded information can be analog information and/or digital information, as a particular embodiment may suggest or require. Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer. The term "image" can be understood to mean either a "picture," whether visible to a human observer or to an instrument (e.g., a visible image, an infrared image, or a digital representation of such an image, whether in black and white or in color), or alternatively, a "copy", as in "an image of a hard disk," whether a duplicate copy, a compressed copy, or an encrypted copy.

"Microcomputer" is defined herein as synonymous with microprocessor, microcontroller, and digital signal processor ("DSP"). It is understood that memory used by the microcomputer, including for example an imaging or image processing algorithm coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A biocompatible sealable pocket, comprising;
a biocompatible substrate having a first surface; and
a layer of a biocompatible material connected to said first surface of said biocompatible substrate, said layer of said biocompatible material defining an open pocket between said biocompatible substrate and said layer of said biocompatible material, said open pocket having at least one electrical contact accessible on an internal surface thereof, said open pocket configured to accept at least one electrical circuit component and to provide electrical communication between said at least one electrical contact and said at least one electrical circuit component, said biocompatible sealable pocket configured to be sealed and to be implanted within a living organism after accepting said at least one electrical circuit component, said biocompatible sealable pocket configured to provide a biocompatible object capable of biologically significant electrical communication with said living organism within which said biocompatible sealable pocket is implanted;
said biocompatible sealable pocket having no electrical circuit component present therein.

2. The biocompatible sealable pocket of claim 1, wherein said biocompatible substrate having a first surface comprises parylene.

3. The biocompatible sealable pocket of claim 1, wherein said biocompatible substrate having a first surface comprises silicon.

4. The biocompatible sealable pocket of claim 1, wherein said layer of biocompatible material comprises parylene.

5. The biocompatible sealable pocket of claim 1, wherein said open pocket having at least one electrical contact configured to be accessible on an internal surface thereof has electrical contacts on at least two internal surfaces thereof.

6. The biocompatible sealable pocket of claim 1, further comprising an electrical cable having electrical conductors therein configured to make electrical connection between at least one probe element and at least one electrical circuit component situated with said pocket, said probe element configured to make electrical connection to said living organism within which said biocompatible sealable pocket is implanted.

7. The biocompatible sealable pocket of claim 1, further comprising an electrical signal communication device configured to communicate an electrical signal between said at least one electrical circuit component and an electrical circuit external to said living organism.

8. The biocompatible sealable pocket of claim 1, wherein said electrical signal communication device comprises a coil configured to make electromagnetic connection between said at least one electrical circuit component and an electrical circuit external to said living organism.

9. The biocompatible sealable pocket of claim 1, wherein said electrical signal communication device comprises a cable configured to make electromagnetic connection between said at least one electrical circuit component and an electrical circuit external to said living organism.

10. The biocompatible sealable pocket of claim 1, in combination with:
   at least one electrical circuit component situated with said pocket and electrically connected to said at least one electrical connector;
   at least one probe configured to make electrical connection to a living organism and connected to said at least one electrical circuit component; and
   an electrical communication device configured to communicate an electrical signal between said at least one electrical circuit component and an electrical circuit external to said living organism.

11. The biocompatible sealable pocket of claim 1, wherein said layer of biocompatible material comprises a material selected from the group consisting of PMMA, teflon, silicone and polyimide.

12. The biocompatible sealable pocket of claim 8, further comprising a tuning circuit configured to allow operation with an electromagnetic communication signal having predefined electrical parameters.

13. A method of making a biocompatible sealable pocket, comprising the steps of:
   a. providing a substrate having a first surface;
   b. depositing a layer of a sacrificial material having a predefined length, a predefined width, and a predefined thickness on a portion of said surface of said substrate;
   c. depositing a layer of a biocompatible material over said layer of said sacrificial material, said layer of said biocompatible material extending beyond said sacrificial material;
   d. depositing a layer of a conductive material over at least a portion of said layer of said biocompatible material;
   e. depositing a second layer of a biocompatible material over said layer of said conductive material, said layer of said biocompatible material extending beyond said conductive material;
   f. providing openings in said second layer of said biocompatible material to provide electrical access to said conductive material through said second layer of said biocompatible material; and
   g. removing said sacrificial material to define a free volume having said predefined length, said predefined width, and said predefined thickness, said free volume configured to accept at least one electrical circuit component;
   whereby said free volume represents an open pocket having at least one electrical contact configured to be accessible on an internal surface thereof, said open pocket configured to accept at least one electrical circuit component and to provide electrical communication between said at least one electrical contact and said at least one electrical circuit component, said biocompatible sealable pocket configured to be sealed and to be implanted within a living organism after accepting said at least one electrical circuit component, said biocompatible sealable pocket configured to provide a biocompatible object capable of biologically significant electrical communication with said living organism within which said biocompatible sealable pocket is implanted.

14. The method of making a biocompatible sealable pocket of claim 13, further comprising the steps of;
   after the step 12a. of providing substrate, and before the step 12b. of depositing a layer of a sacrificial material,
      13(i) depositing on said surface of said substrate a layer of a biocompatible material, said layer of said biocompatible material having a length greater than said predefined length of said sacrificial material, said layer of said biocompatible material having a width greater than said predefined width of said sacrificial material;
   whereby said free volume represents an open pocket having a biocompatible material as each of its defining surfaces.

15. The method of making a biocompatible sealable pocket of claim 13, wherein said layer of biocompatible material comprises parylene.

16. The method of making a biocompatible sealable pocket of claim 13, wherein said layer of biocompatible material comprises a material selected from the group consisting of PMMA, teflon, silicone and polyimide.

17. The method of making a biocompatible sealable pocket of claim 14, further comprising the step of;
   releasing said biocompatible sealable pocket from said substrate, to provide a self-supporting free standing biocompatible sealable pocket.

18. The method of making a biocompatible sealable pocket of claim 14, further comprising the steps of;
   after the step 13(i) of depositing on said surface of said substrate a layer of a biocompatible material, and before the step 12b. of depositing a layer of a sacrificial material,
      15(ii) depositing a layer of a conductive material over at least a portion of said layer of said biocompatible material;
      15(iii) depositing a layer of a biocompatible material over said layer of said conductive material, said layer of said biocompatible material extending beyond said conductive material; and
      15(iv) providing openings in said layer of said biocompatible material deposited in step 15(iii) to provide electrical access to said conductive material through said layer of said biocompatible material deposited in step 15(iii); and
   after the step 12f. of providing openings, and before the step 12g. of removing said sacrificial material,
      15(v) providing openings in said layers deposited in steps 15(iii), and 12b, 12c, 12d and 12e, to provide electrical access to said conductive material deposited in step 15(ii) through said layer of said biocompatible material deposited in step 15(iii);
   whereby there is provided a biocompatible sealable pocket having electrical contacts on two interior surfaces thereof.

19. The method of making a biocompatible sealable pocket of claim 18, further comprising the steps of;
   releasing said biocompatible sealable pocket from said substrate, to provide a self-supporting free standing biocompatible sealable pocket.

* * * * *